US008188141B2

(12) United States Patent  
Danishefsky et al.

(10) Patent No.: US 8,188,141 B2
(45) Date of Patent: May 29, 2012

(54) ISOMIGRASTATIN ANALOGS IN THE TREATMENT OF CANCER

(75) Inventors: Samuel J. Danishefsky, Englewood, NJ (US); Mihirbaran Mandal, New York, NY (US); David C. Dorn, New York, NY (US); Malcolm A. S. Moore, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 863 days.

(21) Appl. No.: 11/663,580

(22) PCT Filed: Sep. 23, 2005

(86) PCT No.: PCT/US2005/034305
§ 371 (c)(1),
(2), (4) Date: May 28, 2008

(87) PCT Pub. No.: WO2006/034478
PCT Pub. Date: Mar. 30, 2006

(65) Prior Publication Data
US 2009/0054488 A1 Feb. 26, 2009

Related U.S. Application Data

(60) Provisional application No. 60/612,415, filed on Sep. 23, 2004.

(30) Foreign Application Priority Data

May 25, 2005 (WO) ................ PCT/US2005/018603

(51) Int. Cl.
*A61K 31/38* (2006.01)
*A61K 31/335* (2006.01)
*C07D 337/00* (2006.01)
*C07D 309/00* (2006.01)
*C07C 49/00* (2006.01)

(52) U.S. Cl. ............ 514/431; 514/450; 549/9; 549/356; 568/375

(58) Field of Classification Search .................. None
See application file for complete search history.

(56) References Cited

U.S. PATENT DOCUMENTS

| | | | |
|---|---|---|---|
| 2,529,825 | A | 11/1950 | Stoll |
| 3,227,742 | A | 1/1966 | Lafont et al. |
| 4,472,435 | A | 9/1984 | Branca et al. |
| 4,938,949 | A | 7/1990 | Borch et al. |
| 6,326,349 | B1 | 12/2001 | Helmlinger et al. |
| 7,943,800 | B2 | 5/2011 | Danishefsky et al. |
| 2002/0119937 | A1 | 8/2002 | Khosla et al. |
| 2002/0128480 | A1 | 9/2002 | Haneda et al. |
| 2004/0062817 | A1 | 4/2004 | Peshoff |
| 2006/0173205 | A1 | 8/2006 | Fukuda et al. |
| 2007/0037783 | A1 | 2/2007 | Huang et al. |
| 2009/0054488 | A1 | 2/2009 | Danishefsky et al. |
| 2009/0124662 | A1 | 5/2009 | Danishefsky et al. |

FOREIGN PATENT DOCUMENTS

| | | |
|---|---|---|
| EP | 374445 | 6/1990 |
| EP | 1264594 | 12/2002 |
| EP | 1380579 | 1/2004 |
| GB | 989476 | 4/1965 |
| GB | 1036084 | 7/1966 |
| JP | 56-34655 | 4/1981 |
| JP | 56-34656 | 4/1981 |
| JP | 61-56146 | 3/1986 |
| JP | 7-138257 | 5/1995 |
| JP | 2000-178223 | 6/2000 |
| JP | 2001 078793 | 3/2001 |
| JP | 2001 078793 A | 3/2001 |
| JP | 2001 081088 | 3/2001 |
| JP | 2001 081088 A | 3/2001 |
| JP | 2002-519396 | 7/2002 |
| JP | 2003-171335 | 6/2003 |
| WO | WO99/22722 | 5/1999 |
| WO | WO00/01648 | 1/2000 |
| WO | WO01/46451 | 6/2001 |
| WO | WO02/088176 | 11/2002 |
| WO | WO2004/009380 | 1/2004 |
| WO | WO2004/052359 | 6/2004 |
| WO | WO2004/083164 | 9/2004 |
| WO | WO2004/087672 | 10/2004 |
| WO | WO2004/087673 | 10/2004 |
| WO | WO2005/019181 | 3/2005 |
| WO | WO2006/001967 | 1/2006 |
| WO | WO2006/034478 | 3/2006 |
| WO | WO2009/070244 | 6/2009 |

OTHER PUBLICATIONS

Jantzen and Robinson. Modern Pharmaceutics, 1996, p. 596.*
"Metabolite-Encyclopedia.com", http://www.encyclopedia.com/doc/1E1-metabolit.html, accessed Jan. 25, 2008.*
Shin et al. Journal of Biological Chemistry, 2005, 280(10), 41439-41448.*
Geho et al. Physiology, 2005, 20, 194-200.*
Woo et al. Journal of Antibiotics, 2002, 55(2), 141-146.*
Shi. Journal of Natural Products, 1998, 61, 1427-1440.*
U.S. Appl. No. 13/106,625, Danishefsky, et al.
U.S. Appl. No. 13/053,161, Danishefsky, et al.
Abiko, A.; Liu, J. F.; Masamune, S. *J. Am. Chem. Soc.* 1997, 119, 2586.
Ahmar, M.; Duyck, C.; Fleming I. *J. Chem. Soc., Perkin Trans. 1* 1998, 2721.
Asami, Y.; Kakeya, H.; Onose, R.; Yoshida, A.; Matsuzaki, H.; Osada, H. *Org. Lett.* 2002, 4, 2845.
Aslakson, C. J., and Miller, F. R. 1992. Selective events in the metastatic process defined by analysis of the sequential dissemination of subpopulations of a mouse mammary tumor. Cancer Research 52: 1399-1405.
Berge, et al., J. Pharmaceutical Sciences, 1977, 66: 1-19.
Biswas, K.; Lin, H.; Njardarson, J. T.; Chappell, M. D.; Chou, T. C.; Guan, Y.; Tong, W. P.; He, L.; Horwitz, S. B.; Danishefsky, S. J. *J. Am. Chem. Soc.* 2002, 124, 9825.
Blanchette et al., *Tet. Lett.*, 1984, 25, 2183.

(Continued)

*Primary Examiner* — Noble Jarrell
(74) *Attorney, Agent, or Firm* — Choate Hall & Stewart LLP; Brenda Herschbach Jarrell; John P. Rearick

(57) ABSTRACT

The present invention provides compounds having formula (I): (I) wherein n, $R_1$-$R_5$, $R_a$-$R_b$, Q, $Y_1$ and $Y_2$ are as defined herein; and additionally provides methods for the synthesis thereof, compositions thereof, and methods for the use thereof in the treatment of various disorders including cancer, metastasis and disorders involving increased angiogenesis.

59 Claims, 9 Drawing Sheets

OTHER PUBLICATIONS

Boden, E. P.; Keck, G. E. *J. Org. Chem.* 1985, 50, 2394.
Brower, V. *Nat. Biotechnol.* 1999, 17, 963.
Bundgaard, Design and application of prodrugs, In *A textbook of Drug Design and Development* 1991, 113-191.
Capitosti, S. M.; Hansen, T. P.; Brown, M. L. *Bioorg. Med. Chem.* 2004, 12, 327.
Carmeliet, P. *Nat. Med.* 2003, 9, 653.
Chan, J.; Jamison, T. F. *J. Am. Chem. Soc.* 2003, 125, 11514.
Chaomin, L.; Bardhan, S.; Pace, E. A.; Liang, M. C.; Gilmore, T. D.; Porco Jr., J. A. *Org. Lett.* 2002, 4, 3267.
Chun, J.; Li, G.; Byun, H. S.; Bittman, R. *J. Org. Chem.* 2002, 67, 2600.
Cristofanilli, et al. *Nat. Rev. Drug Discovery* 2002, 1, 415.
Crystallographic data (excluding structural data) for compound 24 have been deposited with the Cambridge Crystallographic Data Centre (CCDC) as Deposition No. CCDC 230121.
D'Amato, R. J.; Loughnan, M. S.; Flynn, E.; Folkman, J. *Proc. Natl. Acad. Sci.* 1994, 91, 4082.
Danishefsky, S. J. *Aldrichimica Acta* 1986, 19, 59.
Danishefsky, S.J. *Chemtracts* 1989, 2, 273 (Part I).
Danishefsky, S.J. *Chemtracts* 1989, 2, 273 (Part II).
Danishefsky, S. J.; Kitahara, T. *J. Am. Chem. Soc.* 1974, 96, 7807.
Danishefsky, S. J. et al.; *J. Am. Chem. Soc.* 1979, 101, 7001.
Danishefsky, S. J.; Kato, N.; Askin, D.; Kerwin Jr., J. F. *J. Am. Chem. Soc.* 1982, 104, 360.
Danishefsky et al., *J. Am. Chem. Soc.*, 1985, 107, 1256.
Danishefsky et al., *J. Am. Chem. Soc.* 1996, 118, 2843.
Deplanque, G.; Harris, A. L. *Eur. J Cancer* 2000, 36, 1713.
Dermer, *Bio/Technology* 1994, 12, 320.
Dess, D. B.; Martin, J. C. *J. Am. Chem. Soc.* 1991, 113, 7277.
Dixon, D. J.; Krause, L.; Ley, S. V. *J. Chem. Soc., Perkin Trans. 1*, 2001, 2516.
Dredge, K.; Dalgleish, A. G.; Marriott, J. B. *Anti-Cancer Drugs* 2003, 14, 331.
Duffey, M. O.; LeTiran, A.; Morken, J. P. *J. Am. Chem. Soc.* 2003, 125, 1458.
Edmonds, M. K.; Abell, A. D. *J. Org. Chem.* 2001, 66, 3747.
Egawa, Y. et al.; *Chem. Pharm. Bull.* 1963, 11, 589.
Eng, H. M.; Myles, D. C. *Tetrahedron Lett.* 1999, 40, 2279.
Evans, D.A., *Aldrichimica Acta*, 1982, 15, 23-32.
Evans et al., *J. Am. Chem. Soc.*, 2002, 124, 392.
Fenteany, G.; Zhu, S. *Curr. Top. Med. Chem.* 2003, 3, 593.
Ferrier, *J Chem. Soc.*, 1964, 5443.
Freshney, Culture of Animal Cells: A manual of basic technique. Alan R. Liss, 1983, New York, p. 4.
Garbaccio, R. M.; Stachel, S. J.; Baeschlin, D. K.; Danishefsky, S. J. *J. Am. Chem. Soc.* 2001, 123, 10903.
Gaul, C. et al.; *J. Am. Chem. Soc.* 2003, 125, 6042.
Gaul et al.; *J. Amer. Chem. Soc.* 2002, 126(36):11326-11337.
Gaul, C., et al., Tetrahedron Lett., 2002, 43, 9039-9042.
Geho et al, *Physiology*, 2005, 20, 194-200.
Gura, *Science* 1997, 278, 1041-1042.
Harris, C. R.; Danishefsky, S. J. *J. Org. Chem.* 1999, 64, 8434.
Hayashi, Y.; Shoji, M.; Yamaguchi, J.; Sato, K.; Yamaguchi, S.; Mukaiyama, T.; Sakai, K.; Asami, Y.; Kakeya, H.; Osada, H. *J. Am. Chem. Soc.* 2002, 124, 12078.
Hirai, K.; Ooi, H.; Esumi, T.; Iwabuchi, Y.; Hatakeyama, S. *Org. Lett.* 2003, 5, 857.
Hochlowski, J. E.; Whittern, D. N.; Hill, P.; McAlpine, J. B. *J. Antibiot.* 1994, 47, 870.
Inanaga et al., *Bull. Chem. Soc. Jpn.*, 1979, 52, 1989.
International Search Report for PCT/US2004/009380, mailed Sep. 21, 2004.
International Search Report for PCT/US2004/009571, mailed Sep. 22, 2004.
International Search Report for PCT/US2005/018603, mailed Apr. 10, 2006.
International Search Report for PCT/US2005/034305, mailed Sep. 5, 2006.
Jantzen and Robinson, *Modern Pharmaceutics* 1996, 596.
Jorgensen et al., *J. Org. Chem.*, 2001, 66, 4630.
Jung, H. J.; Lee, H. B.; Kim, C. J.; Rho, J. R.; Shin, J.; Kwon, H. J. *J. Antibiot.* 2003, 56, 492.
Kadam, S.; McAlpine, J.B. *J. Antibiot.* 1994, 47, 875.
Kakeya, H.; Onose, R.; Koshino, H.; Yoshida, A.; Kobayashi, K.; Kageyama, S. I.; Osada, H. *J. Am. Chem. Soc.* 2002, 124, 3496.
Kakeya, H.; Onose, R.; Yoshida, A.; Koshino, H.; Osada, H. *J. Antibiot.* 2002, 55, 829.
Karwowski, J. P.; Jackson, M.; Sunga, G.; Sheldon, P.; Poddig, J. B.; Kohl, W. L.; Adam, S. *J. Antibiot.* 1994, 47, 862.
Katzenellenbogen, J.A., et al., *J. Am. Chem. Soc.*, 1976, 98, 4925.
Kerbel, R.; Folkman, *J. Nat. Rev. Cancer* 2003, 2, 727.
Kitaori, K., Furukawa, Y., Yoshimoto, H.; Otera, J. *Tetrahedron* 1999, 55, 14381.
Klohs, W. D.; Hamby, J. M. *Curr. Opin. Biotechnol.* 1999, 10, 544.
Kondo, H.; Oritani, T.; Kiyota, H. *Eur. J. Org. Chem.* 2000, 3459.
Lauffenburger, D. A.; Horwitz, A. F. *Cell* 1996, 84, 359.
Lee, W. W.; Chang, S. *Tetrahedron: Asymmetry* 1999, 10, 4473.
Li, D. R.; Xia, W. J.; Shi, L.; Tu, Y. Q. *Synthesis* 2003, 41.
Lin, S.; Danishefsky, S.J. *Angew. Chem. Int. Ed.* 2002, 41(3), 512-5.
Lin, S.; Danishefsky, S. J. *Angew. Chem. Int. Ed.* 2001, 40(10), 1967-1970.
Luche et al., *J. Am. Chem. Soc.*, 1979, 101, 5848.
Mahoney et al., *J. Am. Chem. Soc.*, 1988, 110, 291.
Mattson, M. P.; Furukawa, K. *Apoptosis* 1997, 2, 257.
Mehta, G.; Islam, K. *Tetrahedron Lett.* 2003, 44, 3569.
Miller, F. R., Miller, B. E., and Heppner, G. H. 1983. Invasion Metastasis 3: 22-31.
Mukaiyama, T. *Agnew. Chem. Int. Ed.* 1979, 18, 707.
Mukaiyama, T., Usui, M.; Shimada, E.; Saigo, K. *Chem. Lett.* 1975, 1045.
Myers, A. G.; Siu, M.; Ren, F. *J. Am. Chem. Soc.* 2002, 124, 4230.
Nakae et al., J. Antibiot., 2000, 53, 1228-1230.
Nakae K.; Yoshimoto, Y.; Sawa, T.; Homma, Y.; Hamada, M.; Takeuchi, T.; Imoto, M. *J Antibiotics* 2000, 53,1130-1136.
Nakamura, H., et al., J. Antibiot., 2002, 55, 442-444.
Njardarson, J.T., et al., J. Am. Chem. Soc., 2004, 126, 1038-1040.
Ogasawara, M.; Matsubara, T.; Suzuki, H. *Biol. Pharm. Bull.* 2001, 24, 720.
Ogasawara, M.; Matsubara, T.; Suzuki, H. *Biol. Pharm. Bull.* 2001, 24, 917.
Ogasawara, M.; Matsunaga, T.; Takahashi, S.; Saiki, I.; Suzuki, H. *Biol. Pharm. Bull.* 2002, 25, 1491.
Prakash, G. K. S.; Krishnamurti, R.; Olah, G. A. *J. Am. Chem. Soc.* 1989, 111, 393.
Pulaski, B. A., and Ostrand-Rosenberg, S. 1998. Cancer Res 58: 1486-1493.
Raje, N.; Anderson, K. C. *Curr. Opin. Oncol.* 2002, 14, 635.
Reetz, M. T.; Kessler, K. *J. Org. Chem.* 1985, 50, 5434.
Rice, et al., Anal. Biochem. 1996, 241: 254-259.
Rivkin, A.; Yoshimura, F.; Gabarda, A. E.; Chou, T. C.; Dong, H.; Tong, W. P.; Danishefsky, S. J. *J. Am. Chem. Soc.* 2003, 125, 2899.
Roskelley, C. D.; Williams, D. E.; McHardy, L. M.; Leong, K. G.; Troussard, A.; Karsan, A.; Andersen, R. J.; Dedhar, S.; Roberge, M. *Cancer Res.* 2001, 61, 6788.
Scappaticci, F. A. *J Clin. Oncol.* 2002, 20, 3906.
Scholl et al., *Org. Lett.*, 1999, 1, 953.
Scholl, M.; Trnka, T. M.; Morgan, J. P.; Grubbs, R. H *Tetrahedron Lett.* 1999, 40, 2247.
Seco, J. M.; Latypov, S. K.; Quinoa, E.; Riguera, R. *Tetrahedron* 1997, 53, 8541.
Seco, J. M.; Quinoa, E.; Riguera, R. *Tetrahedron: Asymmetry* 2000, 11, 2781.
Shan et al.; *PNAS* 2005, 102(10):3772-3776.
Shin et al, *Journal of Biological Chemistry* 2005, 280(50), 41439-41448.
Shiozawa, H.; Takahashi, M.; Takatsu, T.; Kinoshita, T.; Tanzawa, K.; Hosoya, T.; Furuya, K.; Furihata, K.; Seto, H. *J. Antibiot.* 1995, 48, 357.
Shoji, M.; Yamaguchi, J.; Kakeya, H.; Osada, H.; Hayashi, Y. *Angew. Chem. Int. Ed.* 2002, 41, 3192.
Singh et al.; *Indian Journal of Chemistry* 2002, 41 B:423-426.
Smith III, A. B.; Frohn, M. *Org. Lett.* 2001, 3, 3979.
Song et al., *Org. Lett.*, 2002, 4, 647.

Stachel, S. J. ; Biswas, K.; Danishefsky, S. J. *Curr. Pharm. Des.* 2001, 7, 1277.
Stachel, S.J.; Lee, C.B.; Spassova, M.; Chappell, M.D.; Bornmann, W.G.; Danishefsky, S.J. *J. Org. Chem.* 2001, 66, 4369.
Stella et al.; *Advanced Drug Delivery Reviews*, 2007, 677-694.
Sugawara, K.; Nishiyama, Y.; Toda, S.; Komiyama, N.; Hatori, M.; Moriyama, T.; Sawada, Y.; Kamei, H. ; Konishi, M.; Oki, T. *J. Antibiot.* 1992, 45, 1433.
Takayasu, Y.; Tsuchiya, K.; Aoyama, T.; Sukenaga, Y. *J. Antibiot.* 2001, 54, 1111.
Takayasu, Y.; Tsuchiya, K.; Sukenaga, Y. *J. Antibiot.* 2002, 55, 337.
Takemoto, Y., et al., J. Antibiot., 2001, 54, 1104-1107.
Tatsuta, K.; Masuda, N. *J. Antibiot.* 1998, 51, 602.
Tebbe, F. N.; Parshall, G. W.; Reddy, G. S. *J. Am. Chem. Soc.* 1978, 100, 3611.
Thomas et al., *Curr. Opin. Oncol.* 2000, 12(6), 564-573.
Trost, B. M.; Bunt, R. C.; Pulley, S. R. *J. Org. Chem.* 1994, 59, 4202.
Van't Veer et al.; *Nature Medicine* 2003, 9(8):999-1000.
Wakabayashi, T.; Kageyama, R.; Naruse, N.; Tsukahara, N.; Funahashi, Y.; Kitoh, K.; Watanabe, Y. *J. Antibiot.* 1997, 50, 671.
Williams, D. E.; Craig, K. S.; Patrick, B.; McHardy, L. M.; van Soest, R.; Roberge, M.; Andersen, R. J. *J. Org. Chem.* 2002, 67, 245.
Williams, D. E.; Lassota, P.; Andersen, R. J. *J. Org. Chem.* 1998, 63, 4838.
Woo et al., J. Antibiot., 2002, 55, 141-146.
Woodhouse, E. C.; Chuaqui, R. F.; Liotta, L. A. *Cancer* 1997, 80 (S8), 1529.
Xiang, G.; McLaughlin, L. W. *Tetrahedron* 1998, 54, 375.
Yamamoto, K. ; Garbaccio, R. M. ; Stachel, S. J.; Solit, D. B.; Chiosis, G. ; Rosen, N.; Danishefsky, S. J. *Angew. Chem. Int. Ed.* 2003, 42, 1280.
Yamamoto, K.; Biswas, K.; Gaul, C.; Danishefsky, S. J. *Tetrahedron Lett.* 2003, 44, 3297.
Yang, Z. Q.; Kwok, B. Ho ; Lin, S.; Koldobskiy, M. A.; Crews, C. M.; Danishefsky, S. J. *Chembiochem* 2003, 4, 508.
Yang, Z. Q.; Danishefsky, S. J. *J. Am. Chem. Soc.* 2003, 125, 9602.
Yoshimura, F.; Rivkin, A.; Gabarda, A. E.; Chou, T. C.; Dong, H.; Sukenick, G.; Morel, F. F.; Taylor, R. E.; Danishefsky, S. J. *Angew. Chem. Int. Ed.* 2003, 42, 2518.
U.S. Appl. No. 13/106,625, mailed May 12, 2011, Danishefsky et al.
U.S. Appl. No. 13/053,161, mailed Mar. 21, 2011, Danishefsky et al.

* cited by examiner

Bioluminescence imaging (BLI) of intraperitoneally injected Ovcar3 ovarian cancer cell. (A) whole mouse ventral image. (B) preparation of mouse organs (spleen liver and lung) to measure individual tumor burden.

Histological sections of Liver lung and spleen, demonstrating the infiltration of Ovcar3 ovarian cancer cells into the tissue. Left panel (A, B, C): healthy mice; right panel (D, E, F): intraperitoneally injected ovarian metastatic mice.

ISOMIGRASTATIN ANALOGS IN THE TREATMENT OF CANCER

PRIORITY

The present application claims priority to U.S. Provisional Application No. 60/612,415, filed Sep. 23, 2004 and International Application No.: PCT/US2005/18603 filed May 25, 2005. In addition, the present application is related to International Application Nos.: PCT/US04/09380 and PCT/US04/09571, each filed Mar. 26, 2004; and U.S. Provisional Application Nos. 60/574,114, filed May 25, 2004; 60/458,827, filed Mar. 28, 2003; and 60/496,165, filed Aug. 19, 2003. The entire contents of each of the above-referenced applications are hereby incorporated herein by reference.

GOVERNMENT SUPPORT

This invention was supported by grant 08748 from the National Cancer Institute, grant AI-16943 from the National Institutes of Health, and grant DAMD17-03-1-0444 from the U.S. Army. The U.S. government has certain rights in this invention.

BACKGROUND OF THE INVENTION

Migrastatin (1) is a 14-membered ring macrolide natural product, that was first isolated from a cultured broth of *Steptomyces* sp. MK929-43F1 by Imoto et al. (see, Nakae et al., *J. Antibiot.*, 2000, 53, 1130-1136; and Nakae et al., *J. Antibiot.*, 2000, 53, 1228-1230). It was recently reported that cultures of *Steptomyces platensis* also produce Migrastatin (1a) and a related 12-membered ring macrolide compound, isomigrastatin (1b) (see, Woo et al., *J. Antibiot.*, 2002, 55, 141-146).

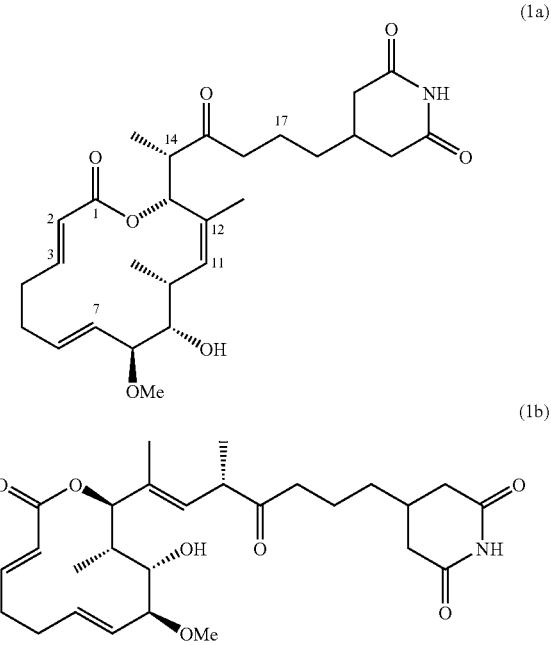

Migrastatin has been shown to inhibit both migration and anchorage-independent growth of human tumor cells (see, Nakae et al., *J. Antibiot.*, 2001, 54, 1104-1107), and has sparked interest in the area of cancer research. Specifically, migration of tumor cells is part of the complex process of metastasis, which is the leading cause of death in cancer patients. Therefore, Migrastatin and analogs thereof, including 12-membered ring macrolide isomigrastatin analogs, hold great potential as therapeutic agents for the treatment of cancer.

To date, access to isomigrastatin has only been possible by fermentation techniques. Clearly, there remains a need for isomigrastatin analogs. Therefore, there is a need to develop synthetic methodologies to access a variety of novel analogues of isomigrastatin, particularly those that are inaccessible by making modifications to the natural product. It would also be of particular interest to develop novel compounds that exhibit a favorable therapeutic profile in vivo (e.g., are safe and effective).

SUMMARY OF THE INVENTION

As discussed above, there remains a need for the development of novel isomigrastatin analogs. In one aspect, isomigrastatin analogs of formula (I) are provided:

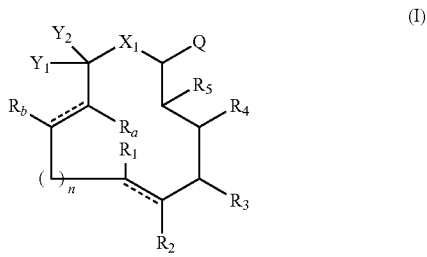

wherein n, $R_1$-$R_5$, $R_a$-$R_b$, Q, $Y_1$ and $Y_2$ are as defined herein. Also provided are pharmaceutical compositions of these compounds, as described generally and in subclasses herein.

The inventive compounds are useful as inhibitors of cell migration, exhibit antiangiogenic activity, and/or have an anti-proliferative effect. Thus these compounds are useful, for example, for the treatment of various disorders including disorders involving malignancy or increased angiogenesis.

In another aspect, the present invention provides methods for treating or lessening the severity of metastasis of tumor cells in a subject. In a further aspect, the present invention provides methods for inhibiting angiogenesis in a subject. In yet another aspect, the present invention provides methods for treating cancer comprising administering to a subject in need thereof a therapeutically effective amount of the compound of the invention. In yet another aspect, the present invention provides methods for treating a non-tumor blood condition associated with angiogenesis in a subject. In yet another aspect, the present invention provides methods for treating an immune disease associated with angiogenesis in a subject. In yet another aspect, the present invention provides methods for treating an infection associated with angiogenesis in a subject. In yet another aspect, the present invention provides methods for treating or lessening the severity of ascites in a subject.

In yet another aspect, the present invention provides a method for treating ovarian tumor metastasis in a subject comprising administering to a subject in need thereof a pharmaceutically acceptable carrier, adjuvant or vehicle and a therapeutically effective amount of a pharmaceutical composition comprising a therapeutically effective amount of a compound of general formula (I):

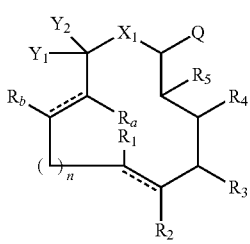

(I)

wherein n, $R_1$-$R_5$, $R_a$-$R_b$, Q, $X_1$, $Y_1$ and $Y_2$ are as defined herein.

DEFINITIONS

It is understood that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic, carbon and heteroatom substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment and prevention, for example of disorders, as described generally above. Examples of substituents include, but are not limited to aliphatic; heteroaliphatic; alicyclic; heterocyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; — or -$GR^{G1}$ wherein G is —O—, —S—, —$NR^{G2}$—, —C(=O)—, —S(=O)—, —$SO_2$—, —C(=O)O—, —C(=O)$NR^{G2}$—, —OC(=O)—, —$NR^{G2}$C(=O)—, —OC(=O)O—, —OC(=O)$NR^{G2}$—, —$NR^{G2}$C(=O)O—, —$NR^{G2}$C(=O)$NR^{G2}$—, —C(=S)—, —C(=S)S—, —SC(=S)—, —SC(=S)S—, —C(=$NR^{G2}$)—, —C(=$NR^2$)O—, C(=$NR^{G2}$)$NR^{G3}$, —OC(=$NR^{G2}$)—, $NR^{G2}$C(=$NR^{G3}$)—, —$NR^{G2}SO_2$—, —$NR^{G2}SO_2NR^{G3}$—, or —$SO_2NR^{G2}$—, wherein each occurrence of $R^{G1}$, $R^{G2}$ and $R^{G3}$ independently includes, but is not limited to, hydrogen, halogen, or an optionally substituted aliphatic, heteroaliphatic, alicyclic, heterocyclic, aromatic, heteroaromatic, aryl, heteroaryl, alkylaryl, or alkylheteroaryl moiety. Additional examples of generally applicable substituents are illustrated by the specific embodiments shown in the Examples that are described herein.

The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic", as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (substituted, unsubstituted, branched or unbranched) having about 1-6 carbon atoms.

In certain embodiments, the alkyl, alkenyl and alkynyl groups employed in the invention contain about 1-20 aliphatic carbon atoms. In certain other embodiments, the alkyl, alkenyl, and alkynyl groups employed in the invention contain about 1-10 aliphatic carbon atoms. In yet other embodiments, the alkyl, alkenyl, and alkynyl groups employed in the invention contain about 1-8 aliphatic carbon atoms. In still other embodiments, the alkyl, alkenyl, and alkynyl groups employed in the invention contain about 1-6 aliphatic carbon atoms. In yet other embodiments, the alkyl, alkenyl, and alkynyl groups employed in the invention contain about 1-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alicyclic", as used herein, refers to compounds which combine the properties of aliphatic and cyclic compounds and include but are not limited to cyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —$CH_2$-cyclopropyl, cyclobutyl, —$CH_2$-cyclobutyl, cyclopentyl, —$CH_2$-cyclopentyl-n, cyclohexyl, —$CH_2$-cyclohexyl, cyclohexenylethyl, cyclohexanylethyl, norborbyl moieties and the like, which again, may bear one or more substituents.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of aliphatic, heteroaliphatic or heterocyclic moieties, may optionally be substituted. An analogous convention applies to other generic terms such as "cycloalkenyl", "cycloalkynyl" and the like.

The term "heteroaliphatic", as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, e.g., in place of carbon atoms. Heteroaliphatic moieties may be branched or linear unbranched. In certain embodiments, heteroaliphatic moieties are substituted by independent replacement of one or more of the hydrogen atoms thereon with one or more moieties including, but not limited to aliphatic; heteroaliphatic; alicyclic; heterocyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; — or -GR$^{G1}$ wherein G is —O—, —S—, —NR$^{G2}$—, —C(=O)—, —S(=O)—, —SO$_2$—, —C(=O)O—, —C(=O)NR$^{G2}$—, —OC(=O)—, —NR$^{G2}$C(=O)—, —OC(=O)O—, —OC(=O)NR$^{G2}$—, —NR$^{G2}$C(=O)O—, —NR$^{G2}$C(=O)NR$^{G2}$, —C(=S)—, —C(=S)S—, —SC(=S)—, —SC(=S)S—, —C(=NR$^{G2}$)—, —C(=NR$^{G2}$)O—, —C(=NR$^{G2}$) NR$^{G3}$—, —OC(=NR$^{G2}$), —NR$^{G2}$C(=NR$^{G3}$)—, —NR$^{G2}$SO$_2$—, —NR$^{G2}$SO$_2$NR$^{G3}$, or —SO$_2$NR$^{G2}$, wherein each occurrence of R$^{G1}$, R$^{G2}$ and R$^{G3}$ independently includes, but is not limited to, hydrogen, halogen, or an optionally substituted aliphatic, heteroaliphatic, alicyclic, heterocyclic, aromatic, heteroaromatic, aryl, heteroaryl, alkylaryl, or alkylheteroaryl moiety. Additional examples of generally applicable substituents are illustrated by the specific embodiments shown in the Examples that are described herein.

The term "heteroalicyclic", "heterocycloalkyl" or "heterocyclic", as used herein, refers to compounds which combine the properties of heteroaliphatic and cyclic compounds and include but are not limited to saturated and unsaturated mono- or polycyclic heterocycles such as morpholino, pyrrolidinyl, furanyl, thiofuranyl, pyrrolyl etc., which are optionally substituted with one or more functional groups, as defined herein. In certain embodiments, the term "heterocyclic" refers to a non-aromatic 5-, 6- or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 2 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to an aryl or heteroaryl ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one, two or three of the hydrogen atoms thereon with but are not limited to aliphatic; heteroaliphatic; alicyclic; heterocyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; — or -GR$^{G1}$ wherein G is —O—, —S—, —NR$^{G2}$—, —C(=O)—, —S(=O)—, —SO$_2$—, —C(=O)O—, —C(=O)NR$^{G2}$—, —OC(=O)—, —NR$^{G2}$C(=O)—, —OC(=O)O—, —OC(=O)NR$^{G2}$—, —NR$^{G2}$C(=O)O—, —NR$^{G2}$C(=O) NR$^{G2}$—, —C(=S)—, —C(=S)S—, —SC(=S)—, —SC(=S)S—, —C(=NR$^{G2}$), —C(=NR$^{G2}$)O—, —C(=NR$^{G2}$) NR$^{G3}$—, —OC(=NR$^{G2}$)—, —NR$^{G2}$C(=NR$^{G3}$)—, —NR$^{G2}$SO$_2$—, —NR$^{G2}$SO$_2$NR$^{G3}$—, or —SO$_2$NR$^{G2}$—, wherein each occurrence of R$^{G1}$, R$^{G2}$ and R$^{G3}$ independently includes, but is not limited to, hydrogen, halogen, or an optionally substituted aliphatic, heteroaliphatic, alicyclic, heterocyclic, aromatic, heteroaromatic, aryl, heteroaryl, alkylaryl, or alkylheteroaryl moiety. Additional examples or generally applicable substituents are illustrated by the specific embodiments shown in the Examples, which are described herein.

Additionally, it will be appreciated that any of the alicyclic or heterocyclic moieties described above and herein may comprise an aryl or heteroaryl moiety fused thereto. Additional examples of generally applicable substituents are illustrated by the specific embodiments shown in the Examples that are described herein.

In general, the term "aromatic moiety", as used herein, refers to stable substituted or unsubstituted unsaturated mono- or polycyclic hydrocarbon moieties having preferably 3-14 carbon atoms, comprising at least one ring satisfying the Huckel rule for aromaticity. Examples of aromatic moieties include, but are not limited to, phenyl, indanyl, indenyl, naphthyl, phenanthryl and anthracyl.

In general, the term "heteroaromatic moiety", as used herein, refers to stable substituted or unsubstituted unsaturated mono-heterocyclic or polyheterocyclic moieties having preferably 3-14 carbon atoms, comprising at least one ring satisfying the Huckel rule for aromaticity. Examples of heteroaromatic moieties include, but are not limited to, pyridyl, quinolinyl, dihydroquinolinyl, isoquinolinyl, quinazolinyl, dihydroquinazolyl, and tetrahydroquinazolyl.

It will also be appreciated that aromatic and heteroaromatic moieties, as defined herein, may be attached via an aliphatic (e.g., alkyl) or heteroaliphatic (e.g., heteroalkyl) moiety and thus also include moieties such as -(aliphatic)aromatic, -(heteroaliphatic)aromatic, -(aliphatic)heteroaromatic, (heteroaliphatic)heteroaromatic, -(alkyl)aromatic, -(heteroalkyl) aromatic, (alkyl)heteroaromatic, and -(heteroalkyl)heteroaromatic moieties. Thus, as used herein, the phrases "aromatic or heteroaromatic moieties" and "aromatic, heteroaromatic, -(alkyl)aromatic, -(heteroalkyl)aromatic, (heteroalkyl)heteroaromatic, and -(heteroalkyl)heteroaromatic" are interchangeable. Substituents include, but are not limited to, any of the previously mentioned substituents, i.e., the substituents recited for aliphatic moieties, or for other moieties as disclosed herein, resulting in the formation of a stable compound.

In general, the term "aryl" refers to aromatic moieties, as described above, excluding those attached via an aliphatic (e.g., alkyl) or heteroaliphatic (e.g., heteroalkyl) moiety. In certain embodiments of the present invention, "aryl" refers to a mono- or bicyclic carbocyclic ring system having one or two rings satisfying the Huckel rule for aromaticity, including, but not limited to, phenyl, naphthyl, tetrahydronaphthyl, indanyl, indenyl and the like.

Similarly, the term "heteroaryl" refers to heteroaromatic moieties, as described above, excluding those attached via an aliphatic (e.g., alkyl) or heteroaliphatic (e.g., heteroalkyl) moiety. In certain embodiments of the present invention, the term "heteroaryl", as used herein, refers to a cyclic unsaturated radical having from about five to about ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

Substituents for aryl and heteroaryl moieties include, but are not limited to, any of the previously mentioned substitutents, i.e., the substituents recited for aliphatic moieties, or for other moieties as disclosed herein, resulting in the formation of a stable compound. For example, aryl and heteroaryl groups (including bicyclic aryl groups) can be unsubstituted or substituted, wherein substitution includes replacement of one, two or three of the hydrogen atoms thereon independently with any one or more of the following moieties including, but not limited to: aliphatic; heteroaliphatic; alicyclic; heterocyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; — or -GR$^{G1}$ wherein G is —O—, —S—, —NR$^{G2}$—, —C(=O)—, —S(=O)—, —SO$_2$—, —C(=O)O—, —C(=O)NR$^{G2}$—, —OC(=O)—, —NR$^{G2}$C(=O)—, —OC(=O)O—, —OC(=O)NR$^{G2}$—, —NR$^{G2}$C(=O)O—, NR$^{G2}$C(=O)NR$^{G2}$—, —C(=S)—, —C(=S)S—, —SC(=S)—, —SC(=S)S—, —C(=NR$^{G2}$)—, —C(=NR$^{G2}$)O—, —C(=NR$^{G2}$)NR$^{G3}$—, —OC(=NR$^{G2}$)—, —NR$^{G2}$C(=NR$^{G3}$)—, —NR$^{G2}$SO$_2$—, —NR$^{G2}$SO$_2$NR$^{G3}$—, or —SO$_2$NR$^{G2}$—, wherein each occurrence of R$^{G1}$, R$^{G2}$ and R$^{G3}$ independently includes, but is not limited to, hydrogen, halogen, or an optionally substituted aliphatic, heteroaliphatic, alicyclic, heterocyclic, aromatic, heteroaromatic, aryl, heteroaryl, alkylaryl, or alkylheteroaryl moiety. Additional examples of generally applicable substituents are illustrated by the specific embodiments shown in the Examples that are described herein.

The terms "alkoxy" (or "alkyloxy"), and "thioalkyl" as used herein refers to an alkyl group, as previously defined, attached to the parent molecular moiety through an oxygen atom ("alkoxy") or through a sulfur atom ("thioalkyl"). In certain embodiments, the alkyl group contains about 1-20 aliphatic carbon atoms. In certain other embodiments, the alkyl group contains about 1-10 aliphatic carbon atoms. In yet other embodiments, the alkyl group contains about 1-8 aliphatic carbon atoms. In still other embodiments, the alkyl group contains about 1-6 aliphatic carbon atoms. In yet other embodiments, the alkyl group contains about 1-4 aliphatic carbon atoms. Examples of alkoxy groups, include but are not limited to, methoxy, ethoxy, propoxy, isopropoxy, n-butoxy, tert-butoxy, neopentoxy and n-hexoxy. Examples of thioalkyl groups include, but are not limited to, methylthio, ethylthio, propylthio, isopropylthio, n-butylthio, and the like.

The term "amine" refers to a group having the structure —N(R)$_2$ wherein each occurrence of R is independently hydrogen, or an aliphatic, heteroaliphatic, aromatic or heteroaromatic moiety, or the R groups, taken together, may form a heterocyclic moiety.

The term "alkylamino" refers to a group having the structure —NHR' wherein R' is alkyl, as defined herein. The term "aminoalkyl" refers to a group having the structure NH$_2$R'—, wherein R' is alkyl, as defined herein. In certain embodiments, the alkyl group contains about 1-20 aliphatic carbon atoms. In certain other embodiments, the alkyl group contains about 1-10 aliphatic carbon atoms. In yet other embodiments, the alkyl, alkenyl, and alkynyl groups employed in the invention contain about 1-8 aliphatic carbon atoms. In still other embodiments, the alkyl group contains about 1-6 aliphatic carbon atoms. In yet other embodiments, the alkyl group contains about 1-4 aliphatic carbon atoms. Examples of alkylamino include, but are not limited to, methylamino, ethylamino, iso-propylamino and the like.

The terms "halo" and "halogen" as used herein refer to an atom selected from fluorine, chlorine, bromine and iodine.

The term "halogenated" denotes a moiety having one, two, or three halogen atoms attached thereto.

The term "haloalkyl" denotes an alkyl group, as defined above, having one, two, or three halogen atoms attached thereto and is exemplified by such groups as chloromethyl, bromoethyl, trifluoromethyl, and the like.

The term "acyloxy", as used herein, does not substantially differ from the common meaning of this term in the art, and refers to a moiety of structure —OC(O)R$_X$, wherein R$_X$ is a substituted or unsubstituted aliphatic, alicyclic, heteroaliphatic, heterocyclic, aryl or heteroaryl moiety.

The term "acyl", as used herein, does not substantially differ from the common meaning of this term in the art, and refers to a moiety of structure —C(O)R$_X$, wherein R$_X$ is a substituted or unsubstituted, aliphatic, alicyclic, heteroaliphatic, heterocyclic, aryl or heteroaryl moiety.

The term "imino", as used herein, does not substantially differ from the common meaning of this term in the art, and refers to a moiety of structure —C(=NR$_X$)R$_Y$, wherein R$_X$ is hydrogen or an optionally substituted aliphatic, alicyclic, heteroaliphatic, heterocyclic, aryl or heteroaryl moiety; and R$_Y$ is an optionally substituted aliphatic, alicyclic, heteroaliphatic, heterocyclic, aryl or heteroaryl moiety.

The term "C$_{1-6}$alkylene", as used herein, refers to a substituted or unsubstituted, linear or branched saturated divalent radical consisting solely of carbon and hydrogen atoms, having from one to six carbon atoms, having a free valence "-" at both ends of the radical.

The term "C$_{2-6}$alkenylene", as used herein, refers to a substituted or unsubstituted, linear or branched unsaturated divalent radical consisting solely of carbon and hydrogen atoms, having from two to six carbon atoms, having a free valence "-" at both ends of the radical, and wherein the unsaturation is present only as double bonds and wherein a double bond can exist between the first carbon of the chain and the rest of the molecule.

As used herein, the terms "aliphatic", "heteroaliphatic", "alkyl", "alkenyl", "alkynyl", "heteroalkyl", "heteroalkenyl", "heteroalkynyl", and the like encompass substituted and unsubstituted, saturated and unsaturated, and linear and branched groups. Similarly, the terms "alicyclic", "heteroalicyclic", "heterocycloalkyl", "heterocycle" and the like encompass substituted and unsubstituted, and saturated and unsaturated groups. Additionally, the terms "cycloalkyl", "cycloalkenyl", "cycloalkynyl", "heterocycloalkyl", "heterocycloalkenyl", "heterocycloalkynyl", "aryl", "heteroaryl" and the like encompass both substituted and unsubstituted groups.

As used herein, the term "isolated", when applied to the compounds of the present invention, refers to such compounds that are (i) separated from at least some components with which they are associated in nature or when they are made and/or (ii) produced, prepared or manufactured by the hand of man.

The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety, which is susceptible to removal in vivo yielding the parent molecule as the pharmacologically active species. An example of a pro-drug is an ester, which is cleaved in vivo to yield a compound of interest. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail herein below.

By the term "protecting group", has used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably non-toxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. For example, in certain embodiments, as detailed herein, certain exemplary oxygen protecting groups are utilized. These oxygen protecting groups include, but are not limited to methyl ethers, substituted methyl ethers (e.g., MOM (methoxymethyl ether), MTM (methylthiomethyl ether), BOM (benzyloxymethyl ether), PMBM or MPM (p-methoxybenzyloxymethyl ether), to name a few), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether), to name a few), esters (e.g., formate, acetate, benzoate (Bz), trifluoroacetate, dichloroacetate, to name a few), carbonates, cyclic acetals and ketals. In certain other exemplary embodiments, nitrogen protecting groups are utilized. These nitrogen protecting groups include, but are not limited to, carbamates (including methyl, ethyl and substituted ethyl carbamates (e.g., Troc), to name a few) amides, cyclic imide derivatives, N-Alkyl and N-Aryl amines, imine derivatives, and enamine derivatives, to name a few. Certain other exemplary protecting groups are detailed herein, however, it will be appreciated that the present invention is not intended to be limited to these protecting groups; rather, a variety of additional equivalent protecting groups can be readily identified using the above criteria and utilized in the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

As used herein, the term "reaction vessel" denotes any container that can contain a reacting solution. For example, test tubes, petri dishes, and wells can all constitute reaction vessels. Preferably, a reaction vessel is a well in a multiwell plate or other multivessel format.

DESCRIPTION OF CERTAIN PREFERRED EMBODIMENTS OF THE INVENTION

Figure 1:
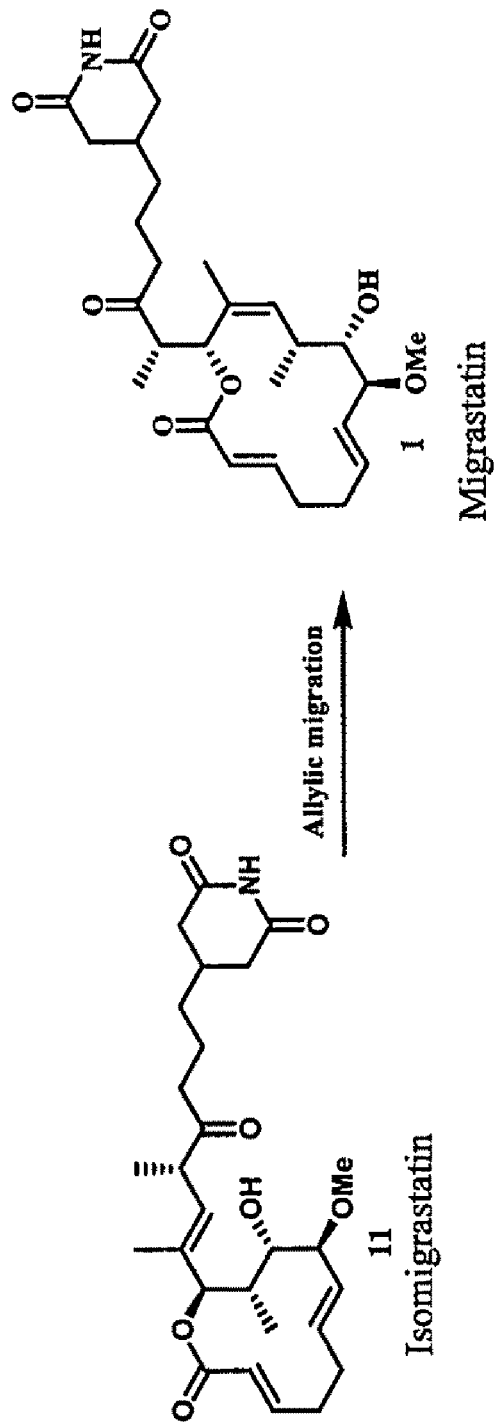
FIG. 1 depicts a proposed biosynthetic route to migrastatin via allylic shift of isomigrastatin.

In recognition of the need to access isomigrastatin analogs, and this class of macrocycles in general, the present invention provides novel 11- to 14-membered macrocyclic compounds, as described in more detail herein, which exhibit the ability to inhibit cell migration. Therefore, the compounds may be useful as angiogenesis inhibitors. The invention also provides information regarding structural elements that participate in or contribute to this activity, and therefore provides insight into the biological activity of this class of compounds. Thus, the compounds of the invention, and pharmaceutical compositions thereof, are useful as antiangiogenesis agents for the treatment of cancer and/or abnormal cell proliferation. In certain embodiments, the compounds of the present invention can be used for the treatment of diseases and disorders including, but not limited to solid tumor cancers, metastasis, ocular angiogenic diseases, diabetic retinopathy, retinopathy of prematurity, corneal graft rejection, neovascular glaucoma, retrolental fibroplasias, rubeosis, solid tumors, blood born tumors, leukemias, tumor metastases, benign tumors, acoustic neuromas, neurofibromas, trachomas, pyogenic granulomas, rheumatoid arthritis, psoriasis, Osler-Webber Syndrome, myocardial angiogenesis, plaque neovascularization, telangiectasia, hemophiliac joints, angiofibroma, or wound granulation, to name a few.

1) General Description of Compounds of the Invention

In certain embodiments, the compounds of the invention include compounds of the general formula (I) as further defined below:

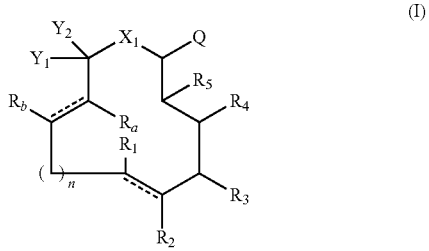

or pharmaceutically acceptable derivatives thereof;
wherein n is an integer from 1 to 4;

R$_1$ and R$_2$ are each independently hydrogen, halogen, —CN, —S(O)$_{1-2}$R$^{1A}$, —NO$_2$, —COR$^{1A}$, —CO$_2$R$^{1A}$, NR$^{1A}$C(=O)R$^{1B}$, NR$^{1A}$C(=O)OR$^{1B}$, —CONR$^{1A}$R$^{1B}$, an aliphatic, heteroaliphatic, alicyclic, heteroalicyclic, aromatic or heteroaromatic moiety, or —WR$^{1A}$; wherein W is independently —O—, —S— or —NR$^{1C}$—, wherein each occurrence of R$^{1A}$, R$^{1B}$ and R$^{1C}$ is independently hydrogen, or an aliphatic, heteroaliphatic, alicyclic, heteroalicyclic, aromatic or heteroaromatic moiety; or R$_1$ and R$_2$, taken together with the carbon atoms to which they are attached, form an alicyclic, heteroalicyclic, aromatic or heteroaromatic moiety;

R$_3$ is hydrogen, halogen, aliphatic, heteroaliphatic, alicyclic, heterocyclic, aryl or heteroaryl moiety, or —WR$^{3A}$; wherein W is independently —O—, —S—, —NR$^{3B}$— or —C(=O)—, wherein R$^{3A}$ is hydrogen, an aliphatic, heteroaliphatic, alicyclic, heterocyclic, aryl or heteroaryl moiety; —C(=O)R$^{3C}$, —Si(R$^{3C}$)$_3$, —C(=S)R$^{3C}$, —C(=NR$^{3C}$)R$^{3C}$, —SO$_2$R$^{3C}$, or —ZR$^{3C}$, wherein Z is —O—, —S—, —NR$^{3D}$, wherein each occurrence of R$^{3B}$, R$^{3C}$ and R$^{3D}$ is independently hydrogen, or an aliphatic, heteroaliphatic, alicyclic, heterocyclic, aryl or heteroaryl moiety;

R$_4$ is halogen, —OR$^{4A}$, OC(=O)R$^{4A}$ or NR$^{4A}$R$^{4B}$; wherein R$^{4A}$ and R$^{4B}$ are independently hydrogen, an aliphatic, heteroaliphatic, alicyclic, heteroalicyclic, aromatic or heteroaromatic moiety; a prodrug moiety, a nitrogen protecting group or an oxygen protecting group; or R$^{4A}$ and R$^{4B}$, taken together with the nitrogen atom to which they are attached, form a heterocyclic or heteroaryl moiety; or R$_4$, taken together with the carbon atom to which it is attached forms a moiety having the structure:

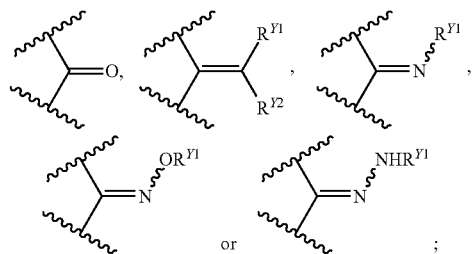

or ;

R$_5$ is hydrogen, an aliphatic, heteroaliphatic, alicyclic, heteroalicyclic, aromatic or heteroaromatic moiety;

R$_a$ and each occurrence of R$_b$ are independently hydrogen, halogen, —CN, —S(O)$_{1-2}$R$^{a1}$, —NO$_2$, —COR$^{a1}$, —CO$_2$R$^{a1}$, —NR$^{a1}$C(=O)R$^{a2}$, —NR$^{a1}$C(=O)OR$^{a2}$, CONR$^{a1}$R$^{a2}$, an aliphatic, heteroaliphatic, alicyclic, heteroalicyclic, aromatic or heteroaromatic moiety, or —WR$^{a1}$; wherein W is independently —O—, —S— or —NR$^{a3}$—, wherein each occurrence of R$^{a1}$, R$^{a2}$ and R$^{a3}$ is independently hydrogen, or an aliphatic, heteroaliphatic, alicyclic, heteroalicyclic, aromatic or heteroaromatic moiety; or R$_a$ and the adjacent occurrence of R$_b$, taken together with the carbon atoms to which they are attached, form an alicyclic, heteroalicyclic, aromatic or heteroaromatic moiety;

X$_1$ is O, S, NR$^{X1}$ or CR$^{X1}$R$^{X2}$; wherein R$^{X1}$ and R$^{X2}$ are independently hydrogen, halogen, an aliphatic, heteroaliphatic, alicyclic, heteroalicyclic, aromatic or heteroaromatic moiety, or a nitrogen protecting group;

Q is hydrogen, halogen, —CN, —S(O)$_{1-2}$R$^{Q1}$, —NO$_2$, —COR$^{Q1}$, —CO$_2$R$^{Q1}$, —NR$^{Q1}$C(=O)R$^{Q2}$, —NR$^{Q1}$C(=O)OR$^{Q2}$, —CONR$^{Q1}$R$^{Q2}$, an aliphatic, heteroaliphatic, alicyclic, heteroalicyclic, aromatic or heteroaromatic moiety, or —WR$^{Q1}$; wherein W is independently —O—, —S— or —NR$^{Q3}$—, wherein each occurrence of R$^{Q1}$, R$^{Q2}$ and R$^{Q3}$ is independently hydrogen, or an aliphatic, heteroaliphatic, alicyclic, heteroalicyclic, aromatic or heteroaromatic moiety;

Y$_1$ and Y$_2$ are independently hydrogen, an aliphatic, heteroaliphatic, alicyclic, heteroalicyclic, aromatic or heteroaromatic moiety; or —WR$^{Y1}$; wherein W is independently —O—, —S— or —NR$^{Y2}$—, wherein each occurrence of R$^{Y1}$ and R$^{Y2}$ is independently hydrogen, or an aliphatic, heteroaliphatic, alicyclic, heteroalicyclic, aromatic or heteroaromatic moiety; or Y$_1$ and Y$_2$ together with the carbon atom to which they are attached form a moiety having the structure:

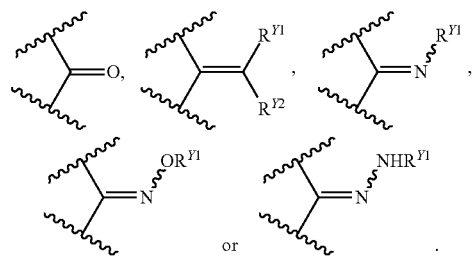

or .

In certain embodiments of compounds described directly above and compounds as described in certain classes and subclasses herein, inventive compounds do not have the following structure:

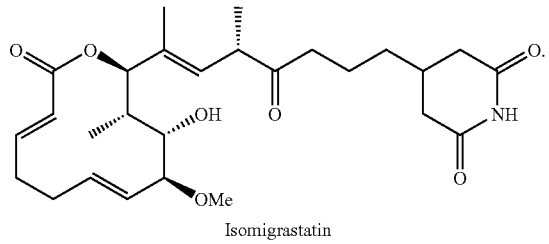

Isomigrastatin

In certain other embodiments, compounds of formula (I) have the following stereochemistry:

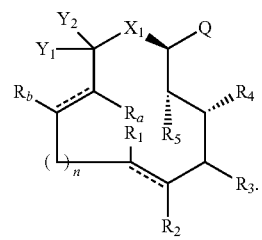

In certain other embodiments, compounds of formula (I) have the following stereochemistry:

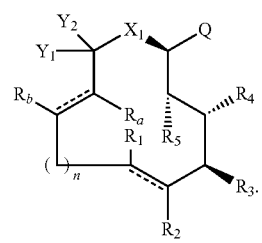

In certain other embodiments, compounds of formula (I) have the following stereochemistry:

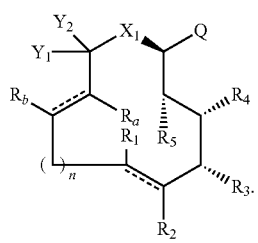

In certain other embodiments, compounds of formula (I) are defined as follows:

n is an integer from 1 to 4;

$R_1$ and $R_2$ are each independently hydrogen or substituted or unsubstituted lower alkyl; or $R_1$ and $R_2$, taken together with the carbon atoms to which they are attached, form an epoxide, an aziridine or a substituted or unsubstituted cyclopropyl moiety;

$R_3$ is hydrogen, halogen, alkyl, heteroalkyl, cycloalkyl, heterocycloalkyl, aryl or heteroaryl moiety, or —$WR^{3A}$; wherein W is independently —O—, —S—, —$NR^{3B}$— or —C(=O)—, wherein $R^{3A}$ is hydrogen, an alkyl, heteroalkyl, cycloalkyl, heterocycloalkyl, aryl or heteroaryl moiety; —C(=O)$R^{3C}$, —Si($R^{3C}$)$_3$, —C(=S)$R^{3C}$, —C(=$NR^{3C}$)$R^{3C}$, —$SO_2R^{3C}$, or —$ZR^{3C}$, wherein Z is —O—, —S—, —$NR^{3D}$, wherein each occurrence of $R^{3B}$, $R^{3C}$ and $R^{3D}$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety;

$R_4$ is halogen, $OR^{4A}$, —OC(=O)$R^{4A}$ or $NR^{4A}R^{4B}$; wherein $R^{4A}$ and $R^{4B}$ are independently hydrogen, or substituted or unsubstituted lower alkyl; a prodrug moiety, a nitrogen protecting group or an oxygen protecting group; or $R^{4A}$ and $R^{4B}$, taken together with the nitrogen atom to which they are attached, form a heterocyclic or heteroaryl moiety; or $R^4$, taken together with the carbon atom to which it is attached forms a moiety having the structure:

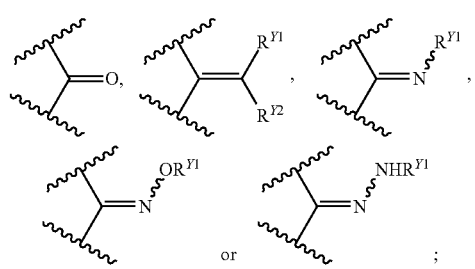

$R_5$ is hydrogen or substituted or unsubstituted lower alkyl;

$R_a$ and each occurrence of $R_b$ are independently hydrogen, halogen, alkyl, heteroalkyl, cycloalkyl, heterocycloalkyl, aryl or heteroaryl moiety, or —$WR^{a1}$; wherein W is independently —O—, —S— or —$NR^{a3}$—, wherein $R^{a1}$ and $R^{a3}$ are independently hydrogen, or an alkyl, heteroalkyl, cycloalkyl, heterocycloalkyl, aryl or heteroaryl moiety; or $R_a$ and the adjacent occurrence of $R_b$, taken together, form an epoxide, an aziridine or a substituted or unsubstituted cyclopropyl moiety;

$X_1$ is O, S, $NR^{X1}$ or $CR^{X1}R^{X2}$; wherein $R^{X1}$ and $R^{X2}$ are independently hydrogen, halogen, substituted or unsubstituted alkyl, heteroalkyl, cycloalkyl, heterocycloalkyl, aryl or heteroaryl, or a nitrogen protecting group;

Q is hydrogen, halogen, —CN, —S(O)$_{1-2}R^{Q1}$, —$NO_2$, —COR$^{Q1}$, —CO$_2R^{Q1}$, —$NR^{Q1}$C(=O)$R^{Q2}$, —$NR^{Q1}$C(=O)OR$^{Q2}$, —CONR$^{Q1}R^{Q2}$, an aliphatic, heteroaliphatic, alicyclic, heteroalicyclic, aryl or heteroaryl moiety, or —$WR^{Q1}$; wherein W is independently —O—, —S— or —$NR^{Q3}$—, wherein each occurrence of $R^{Q1}$, $R^{Q2}$ and $R^{Q3}$ is independently hydrogen, or an aliphatic, heteroaliphatic, alicyclic, heteroalicyclic, aryl or heteroaryl moiety;

$Y_1$ and $Y_2$ are independently hydrogen, an alkyl, heteroalkyl, cycloalkyl, heterocycloalkyl, aryl or heteroaryl moiety; or —$WR^{Y1}$; wherein W is independently —O—, —S— or —$NR^{Y2}$—, wherein each occurrence of $R^{Y1}$ and $R^{Y2}$ is independently hydrogen, or an alkyl, heteroalkyl, cycloalkyl, heterocycloalkyl, aryl or heteroaryl moiety; or $Y_1$ and $Y_2$ together with the carbon atom to which they are attached form a moiety having the structure:

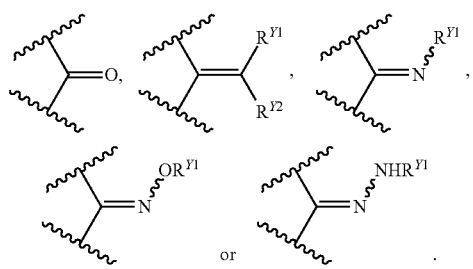

In certain embodiments, the present invention defines certain classes of compounds which are of special interest. For example, one class of compounds of special interest includes those compounds having the structure of formula (I) in which the compound has one of the following structures:

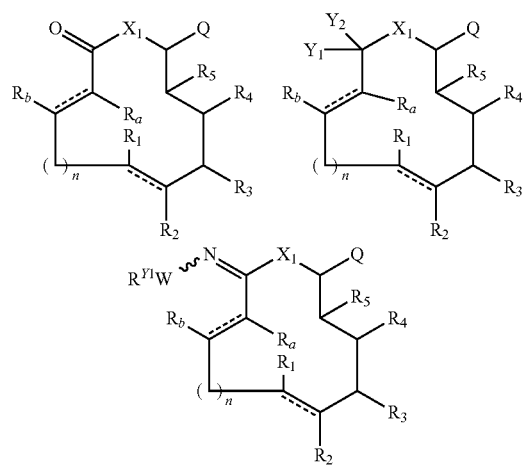

wherein n, $R_1$-$R_5$, $X_1$ and Q are as defined in classes and subclasses herein; W is O or NH; and $Y_1$, $Y_2$ and $R^{Y1}$ are independently hydrogen, or an aliphatic, heteroaliphatic, alicyclic, heteroalicyclic, aryl or heteroaryl moiety.

In certain exemplary embodiments, compounds of the invention shown directly above have the following stereochemistry:

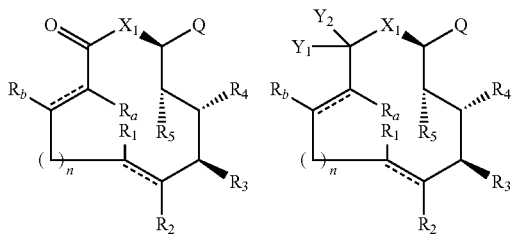

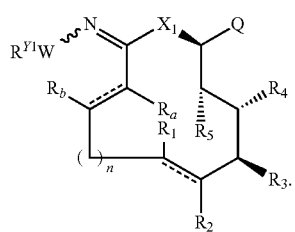

Another class of compounds of special interest includes those compounds having the structure of formula (I) in which Q is hydrogen and the compound has one of the following structures:

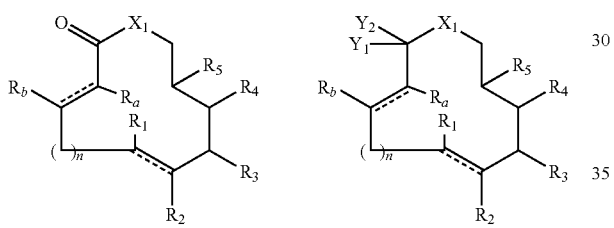

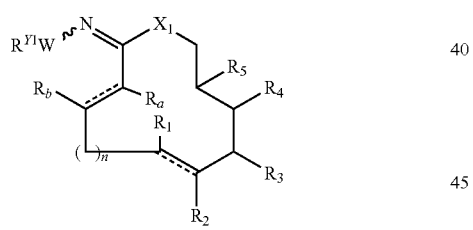

wherein n, $R_1$-$R_5$ and $X_1$ are as defined in classes and subclasses herein; W is O or NH; and $Y_1$, $Y_2$ and $R^{Y1}$ are independently hydrogen, or an aliphatic, heteroaliphatic, alicyclic, heteroalicyclic, aryl or heteroaryl moiety.

In certain exemplary embodiments, compounds of the invention shown directly above have the following stereochemistry:

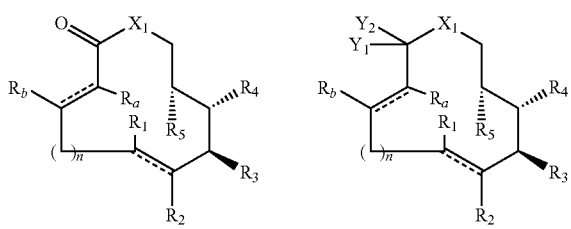

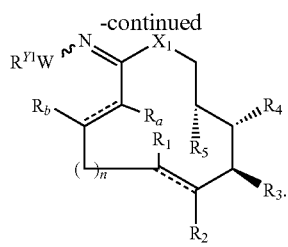

Another class of compounds of special interest includes those compounds having the structure of formula (I) in which $R_a$, $R_b$ and $R_c$ are each hydrogen, Q is a carbonyl-containing moiety and the compound has one of the following structures:

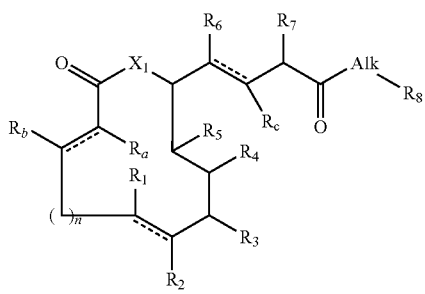

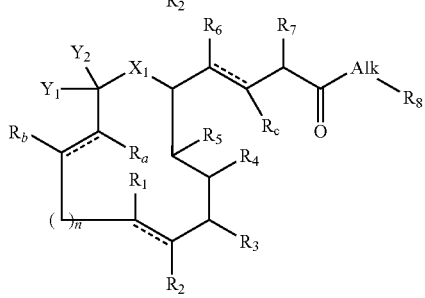

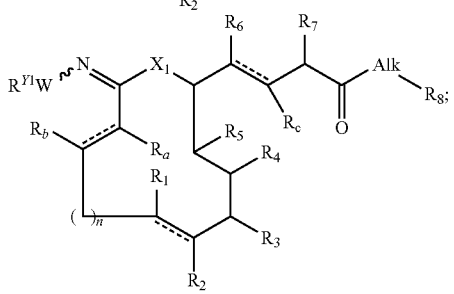

wherein n, $R_1$-$R_5$ and $X_1$ are as defined in classes and subclasses herein; W is or NH; and $Y_1$, $Y_2$ and $R^{Y1}$ are independently hydrogen, or an aliphatic, heteroaliphatic, alicyclic, heteroalicyclic, aryl or heteroaryl moiety; $R_6$ is hydrogen, halogen, —CN, —S(O)$_{1-2}$R$^{6A}$, —NO$_2$, —COR$^{6A}$, —CO$_2$R$^{6A}$, NR$^{6A}$C(=O)R$^{6B}$, —NR$^{6A}$C(=O)OR$^{6B}$, —CONR$^{6A}$R$^{6B}$, an aliphatic, heteroaliphatic, alicyclic, heteroalicyclic, aryl or heteroaryl moiety, or —WR$^{6A}$; wherein W is independently —O—, —S— or —NR$^{6C}$—, wherein each occurrence of R$^{6A}$, R$^{6B}$ and R$^{6C}$ is independently hydrogen, or an aliphatic, heteroaliphatic, alicyclic, heteroalicyclic, aryl or heteroaryl moiety; or $R_6$ and $R_c$, taken together with the carbon atoms to which they are attached, form an alicyclic, heteroalicyclic, aryl or heteroaryl moiety; and F, is hydrogen, halogen, —CN, —S(O)$_{1-2}$R$^{c1}$, —NO$_2$, —COR$^{c1}$, —CO$_2$R$^{c1}$, —NR$^{c1}$C(=O)R$^{c2}$, —NR$^{c1}$C(=O)OR$^{c2}$, —CONR$^{c1}$R$^{c2}$; an aliphatic, heteroaliphatic, alicyclic, heteroalicyclic, aryl or heteroaryl moiety, or —WR$^{c1}$; wherein W is independently —O—, —S— or NR$^{c3}$—, wherein each occurrence of R$^{c1}$, R$^{c2}$ and R$^{c3}$ is independently hydrogen, or an aliphatic, heteroaliphatic, alicyclic, heteroalicyclic, aryl or heteroaryl moiety; or R$_c$, and R$_6$, taken together with the carbon atoms to which they are attached, form an alicyclic, heteroalicyclic, aryl or heteroaryl moiety.

In certain exemplary embodiments, compounds of the invention shown directly above have the following stereochemistry:

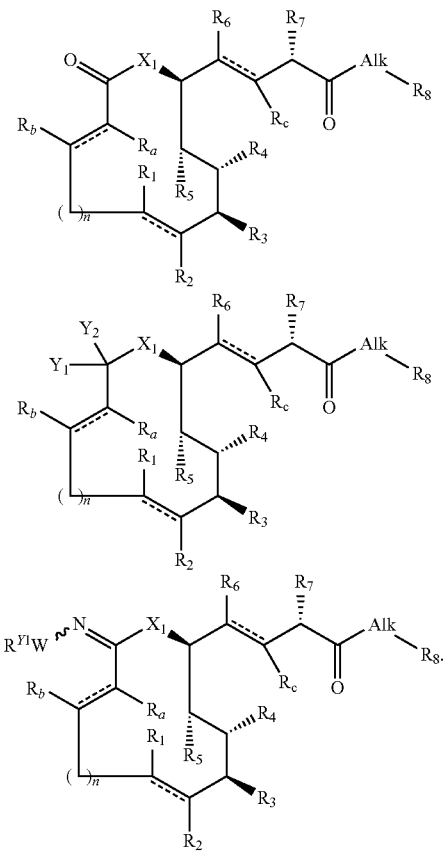

Another class of compounds of special interest includes those compounds having the structure of formula (I) in which R$_a$ and R$_b$ are each hydrogen, Q is hydrogen and the compound has the following structure:

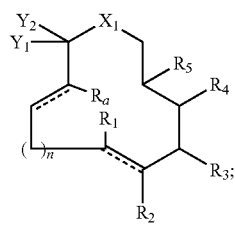

wherein n, R$_1$-R$_5$, Y$_1$, Y$_2$ and X$_1$ are as defined in classes and subclasses herein.

In certain exemplary embodiments, compounds of the invention shown directly above have the following stereochemistry:

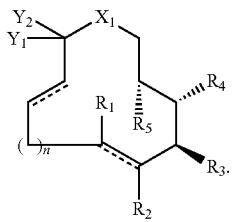

Another class of compounds of special interest includes compounds having the structure of formula (I) in which Y$_1$, Y$_2$, R$_a$ and R$_b$ are each hydrogen, Q is hydrogen, and the compound has the following structure:

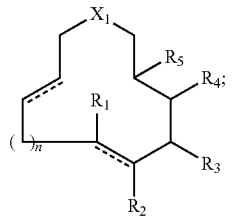

wherein n, R$_1$-R$_5$ and X$_1$ are as defined in classes and subclasses herein.

In certain exemplary embodiments, compounds of the invention shown directly above have the following stereochemistry:

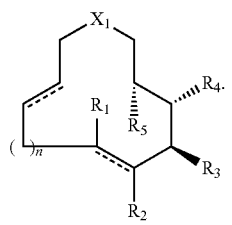

In another aspect, the invention provides compounds of formula (II):

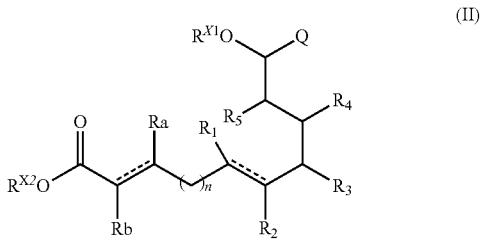

or pharmaceutically acceptable derivatives thereof;
wherein n, R$_1$-R$_5$, R$_a$-R$_b$, Q, Y$_1$ and Y$_2$ are as defined above;
R$^{X1}$ is hydrogen, an aliphatic, heteroaliphatic, alicyclic, heteroalicyclic, aromatic or heteroaromatic moiety, or —C(=O)R$^{X1A}$, —Si(R$^{X1A}$)$_3$, —C(=S)R$^{X1A}$, —C(=NR$^{X1A}$)R$^{X1A}$, —SO$_2$R$^{X1A}$, wherein each occurrence of R$^{X1A}$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety; and $R^{X2}$ is hydrogen, or an aliphatic, heteroaliphatic, alicyclic, heteroalicyclic, aromatic or heteroaromatic moiety.

In certain other embodiments, compounds of formula (II) have the following stereochemistry:

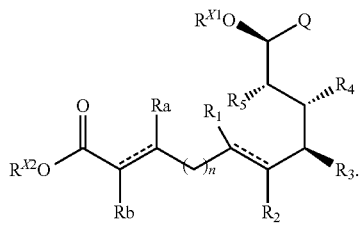

In certain other embodiments, compounds of formula (II) have the following stereochemistry:

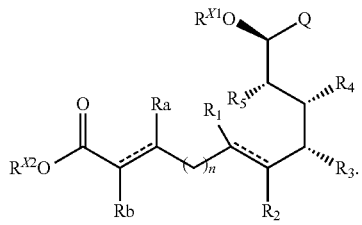

In certain embodiments, compounds of formula (II) do not have the following structure:

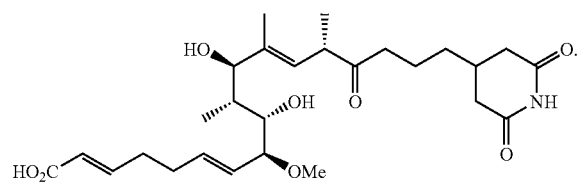

In certain embodiments, the present invention defines certain classes of compounds which are of special interest. For example, one class of compounds of special interest includes those compounds having the structure of formula (II) in which the compound has one of the following structures:

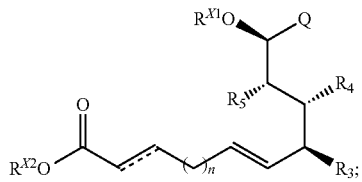

wherein n, $R_3$-$R_5$, $R^{X1}$, $R^{X2}$ and Q are as defined in classes and subclasses herein.

A number of important subclasses of each of the foregoing classes deserve separate mention; these subclasses include subclasses of the foregoing classes in which:

i) $R_1$ is hydrogen, halogen, —CN, —S(O)$_{1-2}$R$^{1A}$, —NO$_2$, —COR$^{1A}$, —CO$_2$R$^{1A}$, —NR$^{1A}$C(=O)R$^{1B}$, —NR$^{1A}$C(=O)OR$^{1B}$, —CONR$^{1A}$R$^{1B}$, an aliphatic, heteroaliphatic, alicyclic, heteroalicyclic, aryl or heteroaryl moiety, or —WR$^{1A}$; wherein W is independently —O—, —S— or —NR$^{1C}$—, wherein each occurrence of R$^{1A}$, R$^{1B}$ and R$^{1C}$ is independently hydrogen, or an aliphatic, heteroaliphatic, alicyclic, heteroalicyclic, aryl or heteroaryl moiety;

ii) $R_1$ is hydrogen, halogen, —CN, —S(O)$_{1-2}$R$^{1A}$, —NO$_2$, —COR$^{1A}$, —CO$_2$R$^{1A}$, —NR$^{1A}$C(=O)R$^{1B}$, —NR$^{1A}$C(=O)OR$^{1B}$, —CONR$^{1A}$R$^{1B}$, an alkyl, heteroalkyl, cycloalkyl, heterocycloalkyl, aryl or heteroaryl moiety, or —WR$^{1A}$; wherein W is independently —O—, —S— or —NR$^{1C}$—, wherein each occurrence of R$^{1A}$, R$^{1B}$ and R$^{1C}$ is independently hydrogen, or an alkyl, heteroalkyl, cycloalkyl, heterocycloalkyl, aryl or heteroaryl moiety;

iii) $R_1$ is hydrogen or lower alkyl;

iv) $R_1$ is hydrogen;

v) $R_1$ is CF$_3$;

vi) $R_2$ is hydrogen, halogen, —CN, —S(O)$_{1-2}$R$^{1A}$, —NO$_2$, —COR$^{1A}$, —CO$_2$R$^{1A}$, —NR$^{1A}$C(=O)R$^{1B}$, —NR$^{1A}$C(=O)OR$^{1B}$, —CONR$^{1A}$R$^{1B}$, an aliphatic, heteroaliphatic, alicyclic, heteroalicyclic, aryl or heteroaryl moiety, or —WR$^{1A}$; wherein W is independently —O—, —S— or —NR$^{1C}$—, wherein each occurrence of R$^{1A}$, R$^{1B}$ and R$^{1C}$ is independently hydrogen, or an aliphatic, heteroaliphatic, alicyclic, heteroalicyclic, aryl or heteroaryl moiety;

vii) $R_2$ is hydrogen, halogen, —CN, —S(O)$_{1-2}$R$^{1A}$, —NO$_2$, —COR$^{1A}$, —CO$_2$R$^{1A}$, —NR$^{1A}$C(=O)R$^{1B}$, —NR$^{1A}$C(=O)OR$^{1B}$, —CONR$^{1A}$R$^{1B}$, an alkyl, heteroalkyl, cycloalkyl, heterocycloalkyl, aryl or heteroaryl moiety, or —WR$^{1A}$; wherein W is independently —O—, —S— or —NR$^{1C}$—, wherein each occurrence of R$^{1A}$, R$^{1B}$ and R$^{1C}$ is independently hydrogen, or an alkyl, heteroalkyl, cycloalkyl, heterocycloalkyl, aryl or heteroaryl moiety;

viii) $R_2$ is hydrogen or lower alkyl;

ix) $R_2$ is hydrogen;

x) $R_2$ is CF$_3$;

xi) $R_1$ and $R_2$ are each hydrogen;

xii) $R_1$ and $R_2$, taken together with the carbon atoms to which they are attached, form an alicyclic, heteroalicyclic, aryl or heteroaryl moiety;

xiii) $R_1$ and $R_2$, taken together with the carbon atoms to which they are attached, form a cycloalkyl, heterocycloalkyl, aryl or heteroaryl moiety;

xiv) $R_1$ and $R_2$, taken together with the carbon atoms to which they are attached, form an epoxide;

xv) $R_1$ and $R_2$, taken together with the carbon atoms to which they are attached, form an aziridine;

xvi) $R_1$ and $R_2$, taken together with the carbon atoms to which they are attached, form a substituted or unsubstituted cyclopropyl;

xvii) $R_3$ is hydrogen, halogen, alkyl, heteroalkyl, cycloalkyl, heterocycloalkyl, aryl or heteroaryl moiety, or —WR$^{3A}$; wherein W is independently —O—, —S—, —NR$^{3B}$ or —C(=O)—, wherein R$^{3A}$ is hydrogen, an alkyl, heteroalkyl, cycloalkyl, heterocycloalkyl, aryl or heteroaryl moiety; —C(=O)R$^{3C}$, —Si(R$^{3C}$)$_3$, —C(=S)R$^{3C}$, C(=NR$^{3C}$)R$^{3C}$, —SO$_2$R$^{3C}$, or —ZR$^{3C}$, wherein Z is —O—, —S—, —NR$^{3D}$, wherein each occurrence of R$^{3B}$, R$^{3C}$ and R$^{3D}$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety;

xviii) $R_3$ is OR$^{3A}$ wherein R$^{3A}$ is hydrogen, alkyl, alkenyl, alkynyl, heteroalkyl, heteroalkenyl, heteroalkynyl, aryl, heteroaryl, silyl, —C(=O)R$^x$, —C(=S)R$^x$, —C(=NR$^x$)R$^y$, —SO$_2$R$^x$, wherein R$^x$ and R$^y$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)R$^A$ or —ZR$^A$, wherein Z is —O—, —S—, —NR$^B$, wherein each occurrence of R$^A$ and R$^B$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety;

xix) $R_3$ is OR$^{3A}$ wherein R$^{3A}$ is hydrogen, an alkyl, heteroalkyl, cycloalkyl, heterocycloalkyl, aryl or heteroaryl moiety; or a prodrug moiety or an oxygen protecting group;

xx) $R_3$ is —OR$^{3A}$ wherein R$^{3A}$ is hydrogen, lower alkyl, aryl, a prodrug moiety or an oxygen protecting group;

xxi) $R_3$ is —OR$^{3A}$ wherein R$^{3A}$ is hydrogen, lower alkyl, aryl or an oxygen protecting group;

xxii) $R_3$ is methoxy;

xxiii) $R_3$ is OAc;

xxiv) the carbon atom bearing $R_4$ is of R-configuration;

xxv) the carbon atom bearing $R_4$ is of S-configuration xxvi) $R_4$ is halogen, —OR$^{4A}$, —C(=O)R$^{4A}$ or —NR$^{4A}$R$^{4B}$; wherein R$^{4A}$ and R$^{4B}$ are independently hydrogen, or substituted or unsubstituted lower alkyl; a prodrug moiety, a nitrogen protecting group or an oxygen protecting group; or R$^{4A}$ and R$^{4B}$, taken together with the nitrogen atom to which they are attached, form a heterocyclic or heteroaryl moiety; or $R_4$, taken together with the carbon atom to which it is attached forms a moiety having the structure:

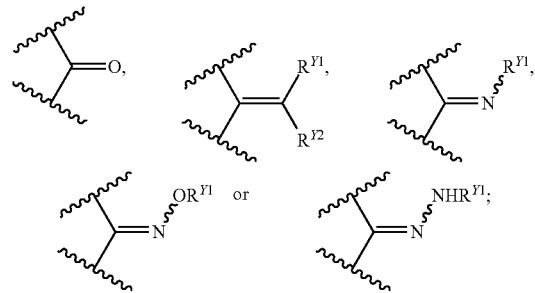

xxvii) $R_4$ is a halogen selected from fluorine, chlorine, bromine, and iodine;

xxviii) $R_4$ is fluorine; xxix) the carbon atom bearing $R_4$ is of R-configuration, and $R_4$ is a halogen selected from fluorine, chlorine, bromine, and iodine;

xxx) the carbon atom bearing R$^4$ is of R-configuration, and 4 is fluorine;

xxxi) $R_4$ is OR$^{4A}$, wherein R$^{4A}$ is hydrogen, a substituted or unsubstituted lower alkyl; acyl; a prodrug moiety or an oxygen protecting group;

xxxii) $R_4$ is OH;

xxxiii) $R_4$ is —OC(=O)R$^{4A}$ wherein R$^{4A}$ is hydrogen, lower alkyl, aryl or heteroaryl;

xxxiv) $R_4$ is OAc;

xxxv) $R_4$ is NR$^{4A}$R$^{4B}$; wherein R$^{4A}$ and R$^{4B}$ are independently hydrogen, a substituted or unsubstituted lower alkyl; a prodrug moiety or a nitrogen protecting group; or R$^{4A}$ and R$^{4B}$, taken together with the nitrogen atom to which they are attached, form a heterocyclic or heteroaryl moiety;

xxxvi) $R_4$ is NR$^{4A}$R$^{4B}$; wherein R$^{4A}$ and R$^{4B}$ are independently hydrogen, alkyl, alkenyl, —C(=O)R$^x$, —C(=O)OR$^x$, —SR$^x$, SO$_2$R$^x$, or R$^{4A}$ and R$^{4B}$, taken together with the nitrogen atom to which they are attached form a moiety having the structure =CR$^x$R$^y$, wherein R$^{4A}$ and R$^{4B}$ are not simultaneously hydrogen and R$^x$ and R$^y$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl, heteroaryl, —C(=O)R$^A$ or —ZR$^A$, wherein Z is —O—, —S—, —NR$^B$, wherein each occurrence of R$^A$ and R$^B$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety;

xxxvii) $R_4$ is NH$_2$;

xxxviii) $R_4$ together with the carbon atom to which it is attached forms a moiety having the structure:

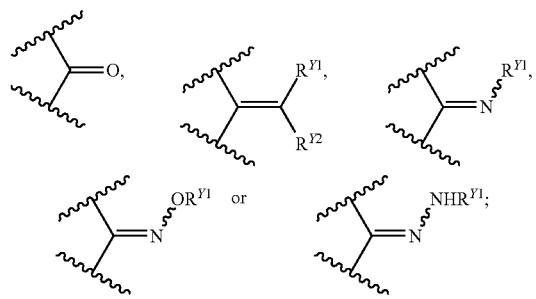

xxxix) $R_4$ together with the carbon atom to which it is attached forms a moiety having the structure:

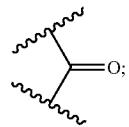

xl) $R_5$ is hydrogen or an alkyl, heteroalkyl, cycloalkyl, heterocycloalkyl, aryl or heteroaryl moiety;

xli) $R_5$ is hydrogen or substituted or unsubstituted lower alkyl;

xlii) $R_5$ is methyl;

xliii) $R_a$ is hydrogen, halogen, —CN, —S(O)$_{1-2}$R$^{a1}$, —NO$_2$, —COR$^{a1}$, —CO$_2$R$^{a1}$, —NR$^{a1}$C(=O)R$^{a2}$, —NR$^{a1}$C(=O)OR$^{a2}$, —CONR$^{a1}$R$^{a2}$, an aliphatic, heteroaliphatic, alicyclic, heteroalicyclic, aryl or heteroaryl moiety, or —WR$^{a1}$; wherein W is independently —O—, —S— or —NR$^{1C}$—, wherein each occurrence of R$^{a1}$, R$^{a2}$ and R$^{a3}$ is independently hydrogen, or an aliphatic, heteroaliphatic, alicyclic, heteroalicyclic, aryl or heteroaryl moiety;

xliv) $R_a$ is hydrogen, halogen, —CN, —S(O)$_{1-2}$R$^{a1}$, —NO$_2$, —COR$^{a1}$, —CO$_2$R$^{a1}$, —NR$^{a1}$C(=O)R$^{a2}$, —NR$^{a1}$C(=O)OR$^a$, —CONR$^{a1}$R$^{a2}$, an alkyl, heteroalkyl, cycloalkyl, heterocycloalkyl, aryl or heteroaryl moiety, or —WR$^{a1}$; wherein W is independently —O—, —S— or —NR$^{1C}$—, wherein each occurrence of R$^{a1}$, R$^{a2}$ and R$^{a3}$ is independently hydrogen, or an alkyl, heteroalkyl, cycloalkyl, heterocycloalkyl, aryl or heteroaryl moiety;

xlv) $R_a$ is hydrogen or lower alkyl;

xlvi) $R_a$ is hydrogen;

xlvii) $R_b$ is hydrogen, halogen, —CN, —S(O)$_{1-2}$R$^{a1}$—, —NO$_2$, COR$^{a1}$, —CO$_2$R$^{a1}$, —NR$^{a1}$C(=O)R$^{a2}$, —NR$^{a1}$C(=O)OR$^{a2}$, —CONR$^{a1}$R$^{a2}$, an aliphatic, heteroaliphatic, alicyclic, heteroalicyclic, aryl or heteroaryl moiety, or —WR$^{a1}$; wherein W is independently —O—, —S— or —NR$^{1C}$—, wherein each occurrence of R$^{a1}$, R$^{a2}$ and R$^{a3}$ is independently hydrogen, or an aliphatic, heteroaliphatic, alicyclic, heteroalicyclic, aryl or heteroaryl moiety;

xlviii) R$_b$ is hydrogen, halogen, —CN, —S(O)$_{1-2}$R$^{a1}$, —NO$_2$, —COR$^{a1}$, —CO$_2$R$^{a1}$, —NR$^{a1}$C(=O)R$^{a2}$, —NR$^{a1}$C(=O)OR$^{a2}$, —CONR$^{a1}$R$^{a2}$, an alkyl, heteroalkyl, cycloalkyl, heterocycloalkyl, aryl or heteroaryl moiety, or —WR$^{a1}$; wherein W is independently —O—, —S— or —NR$^{1C}$—, wherein each occurrence of R$^{a1}$, R$^{a2}$ and R$^{a3}$ is independently hydrogen, or an alkyl, heteroalkyl, cycloalkyl, heterocycloalkyl, aryl or heteroaryl moiety;

xlix) R$_b$ is hydrogen or lower alkyl;

l) R$_b$ is hydrogen;

ln) R$_b$ is CF$_3$;

lii) R$_a$ and R$_b$ are each hydrogen;

liii) R$_a$ and R$_b$, taken together with the carbon atoms to which they are attached, form a cycloalkyl, heterocycloalkyl, aryl or heteroaryl moiety;

liv) R$_a$ and R$_b$, taken together with the carbon atoms to which they are attached, form an epoxide;

lv) R$_a$ and R$_b$, taken together with the carbon atoms to which they are attached, form an aziridine;

lvi) R$_a$ and R$_b$, taken together with the carbon atoms to which they are attached, form a substituted or unsubstituted cyclopropyl;

lvii) X$_1$ is O, S, NR$^{X1}$ or CR$^{X1}$R$^{X2}$; wherein R$^{X1}$ and R$^{X2}$ are independently hydrogen, halogen, substituted or unsubstituted alkyl, heteroalkyl, cycloalkyl, heterocycloalkyl, aryl or heteroaryl, or a nitrogen protecting group;

lviii) X$_1$ is O, NR$^{X1}$ or CR$^{X1}$R$^{X2}$; wherein R$^{x1}$ and R$^{X2}$ are independently hydrogen, halogen, substituted or unsubstituted alkyl, heteroalkyl, cycloalkyl, heterocycloalkyl, aryl or heteroaryl, or a nitrogen protecting group;

lix) X$_1$ is O;

lx) X$_1$ is NH;

lxi) X$_1$ is CH$_2$;

lxii) Q is hydrogen, halogen, —CN, —S(O)$_{1-2}$R$^{Q1}$, —NO$_2$, —COR$^{Q1}$, —CO$_2$R$^{Q1}$, —NR$^{Q1}$C(=O)R$^{Q2}$, —NR$^{Q1}$C(=O)OR$^{Q2}$, —CONR$^{Q1}$R$^{Q2}$, a substituted or unsubstituted alkyl, heteroalkyl, cycloalkyl, heterocycloalkyl, aryl or heteroaryl; or —WR$^{Q1}$; wherein W is independently —O—, —S— or —NR$^{Q3}$—, wherein each occurrence of R$^{Q1}$, R$^{Q2}$ and R$^{Q3}$ is independently hydrogen, or an alkyl, heteroalkyl, cycloalkyl, heterocycloalkyl, aryl or heteroaryl moiety lxiii) Q is a substituted or unsubstituted carbonyl-containing alkyl or heteroalkyl moiety;

lxiv) Q comprises a carbonyl linked to a carbocyclic, heterocyclic, aryl or heteroaryl moiety through a bond or a C$_{1-6}$alkylene or C$_{2-6}$alkenylene chain wherein up to two non-adjacent methylene units are independently optionally replaced by CO, CO$_2$, COCO, CONR$^{Z1}$, OCONR$^{Z1}$, NR$^{Z1}$NR$^{Z2}$, NR$^{Z1}$NR$^{Z2}$CO, NR$^{Z1}$CO, NR$^{Z1}$CO$_2$, NR$^{Z1}$CONR$^{Z2}$, SO, SO$_2$, NR$^{Z1}$SO$_2$, SO$_2$NR$^{Z1}$, NR$^{Z1}$SO$_2$NR$^{Z2}$, O, S, or NR$^{Z1}$; wherein each occurrence of R$^{Z1}$ and R$^{Z2}$ is independently hydrogen, alkyl, heteroalkyl, aryl, heteroaryl or acyl;

lxv) Q has the structure:

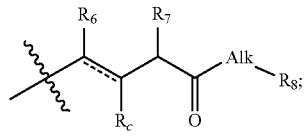

wherein R$_c$ and R$_6$ are independently as defined in classes and subclasses below; R$_7$ is a substituted or unsubstituted lower alkyl or heteroalkyl moiety; R$_8$ is a substituted or unsubstituted alkyl, heteroalkyl, cycloalkyl, heterocycloalkyl, aryl or heteroaryl moiety; and Alk is a bond or a substituted or unsubstituted C$_{1-6}$alkylene or C$_{2-6}$alkenylene chain wherein up to two non-adjacent methylene units are independently optionally replaced by CO, CO$_2$, COCO, CONR$^{Z1}$, OCONR$^{Z1}$, NR$^{Z1}$NR$^{Z2}$, NR$^{Z1}$NR$^{Z2}$CO, NR$^{Z1}$CO, NR$^{Z1}$CO$_2$, NR$^{Z1}$CONR$^{Z2}$, SO, SO$_2$, NR$^{Z1}$SO$_2$, SO$_2$NR$^{Z1}$, NR$^{Z1}$SO$_2$NR$^{Z2}$, O, S, or NR$^{Z1}$; wherein each occurrence of R$^{Z1}$ and R$^{Z2}$ is independently hydrogen, alkyl, heteroalkyl, aryl, heteroaryl or acyl;

lxvi) Q has the structure:

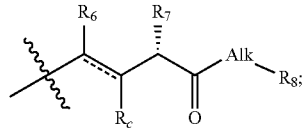

wherein R$_c$ and R$_6$ are independently as defined in classes and subclasses below; R$_7$ is a substituted or unsubstituted, linear or branched, cyclic or acyclic lower alkyl moiety; R$_8$ is a substituted or unsubstituted carbocyclic, heterocyclic, aryl or heteroaryl moiety; and Alk is a bond or a substituted or unsubstituted C$_{1-6}$alkylene or C$_{2-6}$alkenylene chain wherein up to two non-adjacent methylene units are independently optionally replaced by CO, CO$_2$, COCO, CONR$^{Z1}$, OCONR$^{Z1}$, NR$^{Z1}$NR$^{Z2}$, NR$^{Z1}$NR$^{Z2}$CO, NR$^{Z1}$CO, NR$^{Z1}$CO$_2$, NR$^{Z1}$CONR$^{Z2}$, SO, SO$_2$, NR$^{Z1}$SO$_2$, SO$_2$NR$^{Z1}$, NR$^{Z1}$SO$_2$NR$^{Z2}$, O, S, or NR$^{Z1}$; wherein each occurrence of R$^{Z1}$ and R$^{Z2}$ is independently hydrogen, alkyl, heteroalkyl, aryl, heteroaryl or acyl;

lxvii) Q has the structure:

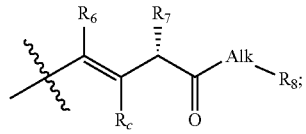

lxviii) Q has the structure:

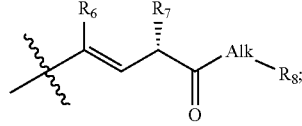

lxix) Q has the structure:

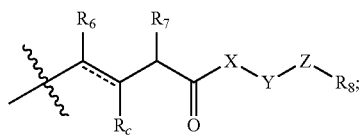

wherein $R_c$ and $R_6$ are independently as defined in classes and subclasses below; $R_7$ is a substituted or unsubstituted, linear or branched, cyclic or acyclic lower alkyl moiety; $R_8$ is a substituted or unsubstituted carbocyclic, heterocyclic, aryl or heteroaryl moiety; and X, Y and Z are independently a bond, —O—, —S—, —C(=O)—, —NR$^{Z1}$—, —CHOR$^{Z1}$, —CHNR$^{Z1}$R$^{Z2}$, C=S, C=N(R$^{Y1}$) or —CH(Hal); or a substituted or unsubstituted $C_{1-6}$alkylene or $C_{2-6}$alkenylene chain wherein up to two non-adjacent methylene units are independently optionally replaced by CO, CO$_2$, COCO, CONR$^{Z1}$, OCONR$^{Z1}$, NR$^{Z1}$NR$^{Z2}$, NR$^{Z1}$NR$^{Z2}$CO, NR$^{Z1}$CO, NR$^{Z1}$CO$_2$, NR$^{Z1}$CONR$^{Z2}$, SO, SO$_2$, NR$^{Z1}$SO$_2$, SO$_2$NR$^{Z1}$, NR$^{Z1}$SO$_2$NR$^{Z2}$, O, S, or NR$^{Z1}$; wherein Hal is a halogen selected from F, Cl, Br and I; and each occurrence of R$^{Z1}$ and R$^{Z2}$ is independently hydrogen, alkyl, heteroalkyl, aryl, heteroaryl or acyl; or R$^{Z1}$ and R$^{Z2}$, taken together with the nitrogen atom to which they are attached, for a heterocyclic or heteroaryl moiety;

lxx) Q has the structure:

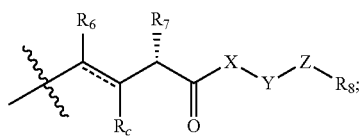

lxxi) Q has the structure:

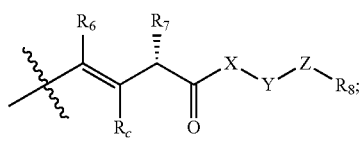

lxxii) Q has the structure:

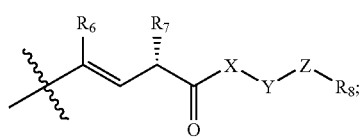

lxxiii) Q has the structure:

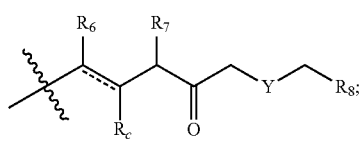

wherein $R_c$ and $R_6$ are independently as defined in classes and subclasses below; $R_7$ is a substituted or unsubstituted, linear or branched, cyclic or acyclic lower alkyl moiety; $R_9$ is a substituted or unsubstituted carbocyclic, heterocyclic, aryl or heteroaryl moiety; and Y is a bond, —O—, —S—, —C(=O)—, —NR$^{Z1}$—, —CHOR$^{Z1}$, —CHNR$^{Z1}$R$^{Z2}$, C=S, C=N(R$^{Y1}$) or —CH(Hal); or a substituted or unsubstituted $C_{1-6}$alkylene or $C_{2-6}$alkenylene chain wherein up to two non-adjacent methylene units are independently optionally replaced by CO, CO$_2$, COCO, CONR$^{Z1}$, OCONR$^{Z1}$, NR$^{Z3}$NR$^{Z2}$, NR$^{Z1}$NR$^{Z2}$CO, NR$^{Z1}$CO, NR$^{Z1}$CO$_2$, NR$^{Z1}$CONR$^{Z2}$, SO, SO$_2$, NR$^{Z1}$SO$_2$, SO$_2$NR$^{Z1}$, NR$^{Z1}$SO$_2$NR$^{Z2}$, O, S, or NR$^{Z1}$; wherein Hal is a halogen selected from F, Cl, Br and I; and each occurrence of R$^{Z1}$ and R$^{Z2}$ is independently hydrogen, alkyl, heteroalkyl, aryl, heteroaryl or acyl; or R$^{Z1}$ and R$^{Z2}$, taken together with the nitrogen atom to which they are attached, for a heterocyclic or heteroaryl moiety;

lxxiv) Q has the structure:

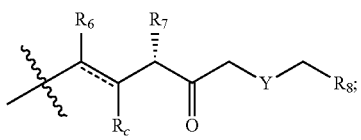

lxxv) Q has the structure:

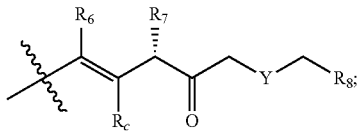

xxvi) Q has the structure:

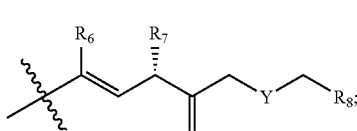

lxxvii) Q has the structure:

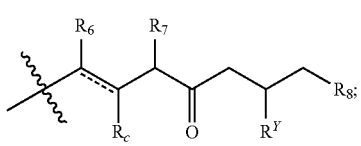

wherein R$^c$ and $R_6$ are independently as defined in classes and subclasses below; $R_7$ is a substituted or unsubstituted, linear or branched, cyclic or acyclic lower alkyl moiety; $R_8$ is a substituted or unsubstituted carbocyclic, heterocyclic, aryl or heteroaryl moiety; and R$^Y$ is hydrogen, halogen, —OR$^{Y1}$ or —NR$^{Y1}$NR$^{Y2}$; wherein R$^{Y1}$ and R$^{Y2}$ are independently hydrogen, alkyl, heteroalkyl, aryl, heteroaryl or acyl, or R$^{Y1}$ and R$^{Y2}$, taken together with the nitrogen atom to which they are attached, for a heterocyclic or heteroaryl moiety;

lxxviii) Q has the structure:

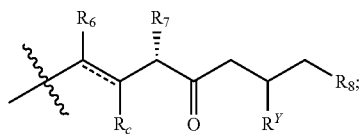

lxxix) Q has the structure:

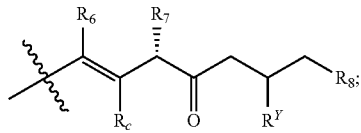

lxxx) Q has the structure:

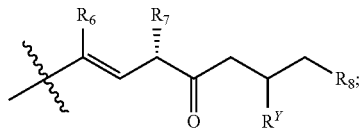

lxxxi) Q is hydrogen;

lxxxii) Q is $CF_3$;

lxxxiii) compounds of subsets lxv)-lxxx) wherein $R^6$ is hydrogen, halogen, —CN, —S(O)$_{1-2}$$R^{6A}$, —NO$_2$, —COR$^{6A}$, —CO$_2$R$^{6A}$, —NR$^{6A}$C(═O)R$^{6B}$, —NR$^{6A}$C(═O)OR$^{6B}$, —CONR$^{6A}$R$^{6B}$, an aliphatic, heteroaliphatic, alicyclic, heteroalicyclic, aryl or heteroaryl moiety, or —WR$^{6A}$; wherein W is independently —O—, —S— or —NR$^{1C}$—, wherein each occurrence of R$^{6A}$, R$^{6B}$ and R$^{6C}$ is independently hydrogen, or an aliphatic, heteroaliphatic, alicyclic, heteroalicyclic, aryl or heteroaryl moiety;

lxxxiv) compounds of subsets lxv)-lxxx) wherein $R^6$ is hydrogen, halogen, —CN, —S(O)$_{1-2}$R$^{1A}$, —NO$_2$, —COR$^{6A}$, —CO$_2$R$^{6A}$, —NR$^{6A}$C(═O)R$^{6B}$, NR$^{6A}$C(═O)OR$^{6B}$, —CONR$^{6A}$R$^{6B}$, an alkyl, heteroalkyl, cycloalkyl, heterocycloalkyl, aryl or heteroaryl moiety, or —WR$^{6A}$; wherein W is independently —O—, —S— or —NR$^{1C}$—, wherein each occurrence of R$^{6A}$, R$^{6B}$ and R$^{6C}$ is independently hydrogen, or an alkyl, heteroalkyl, cycloalkyl, heterocycloalkyl, aryl or heteroaryl moiety;

lxxxv) compounds of subsets lxv)-lxxx) wherein $R_6$ is hydrogen or substituted or unsubstituted lower alkyl;

lxxxvi) compounds of subsets lxv)-lxxx) wherein $R_6$ is methyl;

lxxxvii) compounds of subsets lxv)-lxxx) wherein $R_5$ and $R_6$ are each methyl;

lxxxviii) compounds of subsets lxv)-lxxx) wherein $R_c$ is hydrogen, halogen, —CN, —S(O)$_{1-2}$R$^{c1}$, —NO$_2$, —COR$^{c1}$, —CO$_2$R$^{c1}$, —NR$^{c1}$C(═O)R$^{c2}$, —NR$^{c1}$C(═O)OR$^{c2}$, —CONR$^{c1}$R$^{c2}$, an aliphatic, heteroaliphatic, alicyclic, heteroalicyclic, aryl or heteroaryl moiety, or —WR$^{c1}$; wherein W is independently —O—, —S— or —NR$^{1C}$—, wherein each occurrence of R$^{c1}$, R$^{c2}$ and R$^{c3}$ is independently hydrogen, or an aliphatic, heteroaliphatic, alicyclic, heteroalicyclic, aryl or heteroaryl moiety;

lxxxix) compounds of subsets lxv)-lxxx) wherein $R^c$ is hydrogen, halogen, —CN, —S(O)$_{1-2}$R$^{c1}$, —NO$_2$, —COR$^{c1}$, —CO$_2$R$^{c1}$, —NR$^{c1}$C(═O)R$^{c2}$, —NR$^{c1}$C(═O)OR$^{c2}$, —CONR$^{c1}$R$^{c2}$, an alkyl, heteroalkyl, cycloalkyl, heterocycloalkyl, aryl or heteroaryl moiety, or —WR$^{c1}$; wherein W is independently —O—, —S— or —NR$^{1C}$—, wherein each occurrence of R$^{c1}$, R$^{c2}$ and R$^{c3}$ is independently hydrogen, or an alkyl, heteroalkyl, cycloalkyl, heterocycloalkyl, aryl or heteroaryl moiety;

xc) compounds of subsets lxv)-lxxx) wherein $R_c$ is hydrogen or lower alkyl;

xci) compounds of subsets lxv)-lxxx) wherein $R_c$ is hydrogen;

xcii) compounds of subsets lxv)-lxxx) wherein $R_c$ and $R_6$, taken together with the carbon atoms to which they are attached, form a cycloalkyl, heterocycloalkyl, aryl or heteroaryl moiety;

xciii) compounds of subsets lxv)-lxxx) wherein $R_c$ and $R_6$, taken together with the carbon atoms to which they are attached with the carbon atoms to which they are attached, form an epoxide;

xciv) compounds of subsets lxv)-lxxx) wherein $R_c$ and $R_6$, taken together with the carbon atoms to which they are attached, form an aziridine;

xcv) compounds of subsets lxv)-lxxx) wherein $R_c$ and $R_6$, taken together with the carbon atoms to which they are attached, form a substituted or unsubstituted cyclopropyl;

xcvi) compounds of subsets lxv)-lxxx) wherein $R_7$ is substituted or unsubstituted lower alkyl;

xcvii) compounds of subsets lxv)-lxxx) wherein $R_7$ is methyl;

xcviii) compounds of subsets lxxvii)-lxxx) wherein $R^Y$ is hydrogen;

xcv) compounds of subsets lxxvii)-lxxx) wherein $R^e$ is a halogen selected from fluorine, chlorine, bromine, and iodine;

xcix) compounds of subsets lxxvii)-lxxx) wherein $R^Y$ is fluorine;

c) compounds of subsets lxxvii)-lxxx) wherein $R^Y$ is OR$^{Y1}$, wherein R$^{Y1}$ is hydrogen, a substituted or unsubstituted lower alkyl; a prodrug moiety or an oxygen protecting group;

ci) compounds of subsets lxxvii)-lxxx) wherein $R^Y$ is OH;

cii) compounds of subsets lxxvii)-lxxx) wherein $R^Y$ is NR$^{Y2}$R$^{Y3}$; wherein R$^{Y2}$ and R$^{Y3}$ are independently hydrogen, a substituted or unsubstituted lower alkyl; a prodrug moiety or a nitrogen protecting group; or R$^{Y2}$ and R$^{Y3}$, taken together with the nitrogen atom to which they are attached, form a heterocyclic or heteroaryl moiety;

ciii) compounds of subsets lxxvii)-lxxx) wherein $R^Y$ is NH$_2$;

civ) compounds of subsets lxv)-lxxx) wherein $R_8$ is one of:

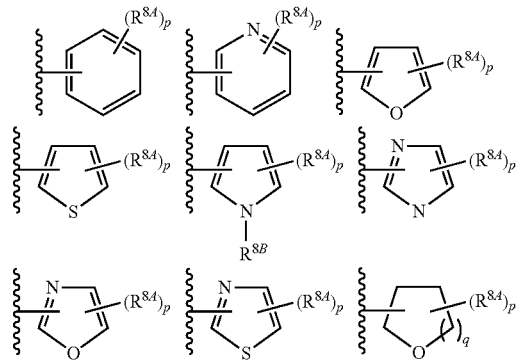

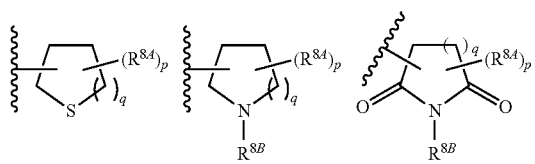 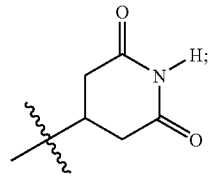

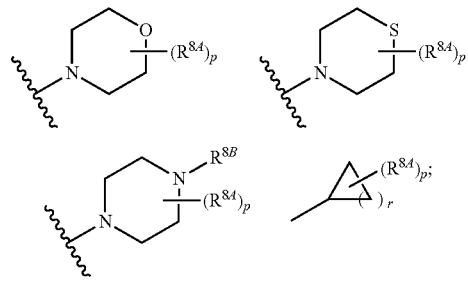 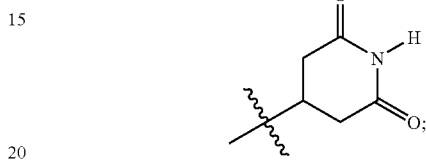

wherein p is an integer from 0 to 5; q is 1 or 2, r is an integer from 1 to 6; each occurrence of $R^{8A}$ is independently hydrogen, alkyl, heteroalkyl, aryl, heteroaryl, -(alkyl)aryl or -(alkyl)heteroaryl, $-OR^{8C}$, $-SR^{8C}$, $-N(R^{8C})_2$, $-SO_2N(R^{8C})_2$, $-(C=O)N(R^{8C})_2$, halogen, $-CN$, $-NO_2$, $-(C=O)OR^{8C}$, $-N(R^{8C})(C=O)R^D$, wherein each occurrence of $R^{8C}$ and $R^{8D}$ is independently hydrogen, lower alkyl, lower heteroalkyl, aryl, heteroaryl, -(alkyl)aryl or -(alkyl) heteroaryl; and each occurrence of $R^{8B}$ is independently hydrogen or lower alkyl;

cv) compounds of subsets lxv)-lxxx) wherein $R_8$ is substituted or unsubstituted cycloalkyl;

cvi) compounds of subsets lxv)-lxxx) wherein $R_8$ is substituted or unsubstituted cyclohexyl;

cvii) compounds of subsets lxv)-lxxx) wherein $R_8$ has the structure:

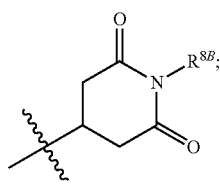

wherein $R^{8B}$ is hydrogen or lower alkyl;

cviii) compounds of subsets lxv)-lxxx) wherein $R_8$ has the structure:

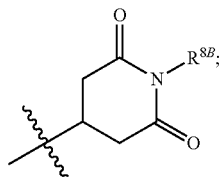

wherein $R^{8B}$ is hydrogen or methyl;

cix) compounds of subsets lxv)-lxxx) wherein $R_8$ has the structure:

cx) $X_1$ is O, $CH_2$ or NH; Q is as described in subsets lxv)-lxxx) wherein $R_8$ has the structure:

cxi) $Y_1$ is hydrogen, an alkyl, heteroalkyl, cycloalkyl, heterocycloalkyl, aryl or heteroaryl moiety; or $-WR^{Y1}$; wherein W is independently $-O-$, $-S-$ or $NR^{Y2}$, wherein each occurrence of $R^{Y1}$ and $R^{Y2}$ is independently hydrogen, or an alkyl, heteroalkyl, cycloalkyl, heterocycloalkyl, aryl or heteroaryl moiety;

cxii) $Y_1$ is hydrogen, lower alkyl or $-OR^{Y1}$; wherein $R^{Y1}$ is hydrogen, or lower alkyl;

cxiii) $Y_1$ is hydrogen or lower alkyl;

cxiv) $Y_1$ is hydrogen;

cxv) $Y_1$ is $CF_3$;

cxvi) $Y_2$ is hydrogen, an alkyl, heteroalkyl, cycloalkyl, heterocycloalkyl, aryl or heteroaryl moiety; or $-WR^{Y1}$; wherein W is independently $-O-$, $-S-$ or $-NR^{Y2}-$, wherein each occurrence of $R^{Y1}$ and $R^{Y2}$ is independently hydrogen, or an alkyl, heteroalkyl, cycloalkyl, heterocycloalkyl, aryl or heteroaryl moiety;

cxvii) $Y_2$ is hydrogen, lower alkyl or $-OR^{Y1}$; wherein $R^{Y1}$ is hydrogen, or lower alkyl;

cxviii) $Y_2$ is hydrogen or lower alkyl;

cxix) $Y_2$ is hydrogen;

cxx) $Y_2$ is $CF_3$;

cxxi) $Y_1$ is $OR^{Y1}$ and $Y_2$ is lower alkyl substituted with one or more halogen atoms selected from F, Cl, Br and I; wherein $R^{Y1}$ is hydrogen or lower alkyl;

cxxii) $Y_1$ is OH and $Y_2$ is $CF_3$;

cxxiii) $X_1$ is $CH_2$; $Y_1$ is $OR^{Y1}$ and $Y_2$ is lower alkyl; wherein $R^{Y1}$ is hydrogen or lower alkyl;

cxxiv) $X_1$ is $CH_2$; $Y_1$ is $OR^{Y1}$ and $Y_2$ is lower alkyl substituted with one or more halogen atoms selected from F, Cl, Br and I; wherein $R^{Y1}$ is hydrogen or lower alkyl;

cxxv) $X_1$ is $CH_2$; $Y_1$ is OH and $Y_2$ is $CF_3$;

cxxvi) $Y_1$ and $Y_2$ together with the carbon atom to which they are attached form a moiety having the structure:

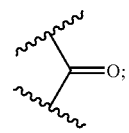

cxxvii) $Y_1$ and $Y_2$ together with the carbon atom to which they are attached form a moiety having the structure:

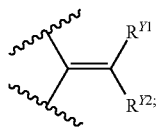

wherein $R^{Y1}$ and $R^{Y2}$ are independently hydrogen or lower alkyl;

cxxvii) $Y_1$ and $Y_2$ together with the carbon atom to which they are attached form a moiety having the structure:

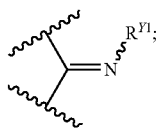

wherein $R^{Y1}$ is hydrogen or lower alkyl;

cxxviii) $Y_1$ and $Y_2$ together with the carbon atom to which they are attached form a moiety having the structure:

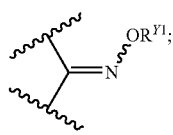

wherein $R^{Y1}$ is hydrogen or lower alkyl;

cxxix) $Y_1$ and $Y_2$ together with the carbon atom to which they are attached form a moiety having the structure:

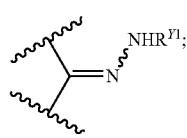

wherein $R^{Y1}$ is hydrogen or lower alkyl;

cxxx) $X_1$ is O; and $Y_1$ and $Y_2$ together with the carbon atom to which they are attached form a moiety having the structure:

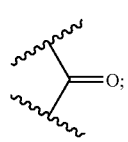

cxxxi) $X_1$ is NH; and $Y_1$ and $Y_2$ together with the carbon atom to which they are attached form a moiety having the structure:

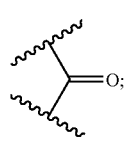

cxxxii) $X_1$ is $CH_2$; and $Y_1$ and $Y_2$ together with the carbon atom to which they are attached form a moiety having the structure:

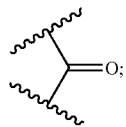

cxxxiii) $X_1$ is $CH_2$; and $Y_1$ and $Y_2$ together with the carbon atom to which they are attached form a moiety having the structure:

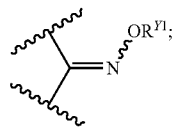

wherein $R^{Y1}$ is hydrogen or lower alkyl;

cxxxiv) $X_1$ is $CH_2$; and $Y_1$ and $Y_2$ together with the carbon atom to which they are attached form a moiety having the structure:

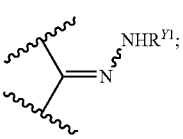

wherein $R^{Y1}$ is hydrogen or lower alkyl;

cxxxv) $X_1$ is O; and $Y_1$ and $Y_2$ are independently hydrogen or lower alkyl;

cxxxvi) $X_1$ is NH; and $Y_1$ and $Y_2$ are independently hydrogen or lower alkyl;

cxxxvii) $X_1$ is $CH_2$; and $Y_1$ and $Y_2$ are independently hydrogen or lower alkyl;

cxxxviii) $X_1$ is O; and $Y_1$ and $Y_2$ are each hydrogen;

cxxxix) $X_1$ is NH; and $Y_1$ and $Y_2$ are each hydrogen;

cxl) $X_1$ is $CH_2$; and $Y_1$ and $Y_2$ are each hydrogen;

cxli) compounds as described in classes and subclasses herein wherein the stereocenter

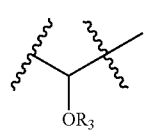

has the following stereochemistry

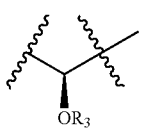

cxlii) compounds as described in classes and subclasses herein wherein the stereocenter

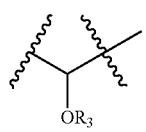

has the following stereochemistry

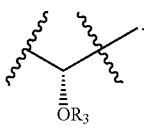

cxliii) n is 1;

cxliv) n is 2;

cxlv) n is 3; and/or cxlvi) n is 4;

cxlvii) $R^{x1}$ is hydrogen; lower alkyl or an oxygen protecting group;

cxlviii) $R^{x1}$ is hydrogen;

cxlix) $R^{X2}$ is hydrogen; lower alkyl or a carboxyl protecting group; and/or cl) $R^{X2}$ is hydrogen.

It will be appreciated that for each of the classes and subclasses described above and herein, any one or more occurrences of groups such as aliphatic, heteroaliphatic, alkyl, heteroalkyl may independently be substituted or unsubstituted, linear or branched, saturated or unsaturated; and any one or more occurrences of alicyclic, heterocyclic, cycloalkyl, aryl, heteroaryl, cycloaliphatic, cycloheteroaliphatic may be substituted or unsubstituted.

The reader will also appreciate that all possible combinations of the variables described in i)-through cl) above (e.g., $R_1$-$R_6$, $R_{a-c}$, Q, $X_1$, $Y_1$ and $Y_2$, among others) are considered part of the invention. Thus, the invention encompasses any and all compounds of formula I, and subclasses thereof, generated by taking any possible permutation of variables $R_1$-$R_6$, $R_{a-c}$, Q, $X_1$, $Y_1$ and $Y_2$, and other variables/substituents (e.g., X, Y, Z, $R^Y$, etc.) as further defined for $R_1$-$R_6$, $R_{a-c}$, Q, $X^1$, $Y_1$ and $Y_2$, described in i)-through cl) above, leading to a stable compound.

As the reader will appreciate, compounds of particular interest include, among others, those which share the attributes of one or more of the foregoing subclasses. Some of those subclasses are illustrated by the following sorts of compounds:

I) Compounds of the Formula (and Pharmaceutically Acceptable Derivatives thereof):

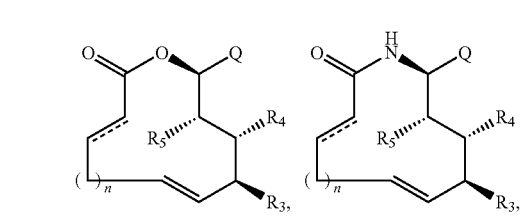

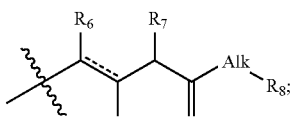

wherein n, $R_3$-$R_5$ and Q are as defined in classes and subclasses herein; and $Y_2$ and $R^{Y1}$ are independently hydrogen or lower alkyl. In certain exemplary embodiments, Q is hydrogen or a carbonyl-containing moiety. In certain exemplary embodiments, Q is hydrogen. In certain exemplary embodiments, Q is $CF_3$.

In certain other embodiments, for compounds of class I) above, Q is a substituted or unsubstituted carbonyl-containing alkyl or heteroalkyl moiety. In certain exemplary embodiments, Q comprises a carbonyl linked to a carbocyclic, heterocyclic, aryl or heteroaryl moiety through a bond or a $C_{1-6}$alkylene or $C_{2-6}$alkenylene moiety. In certain embodiments, Q has the structure:

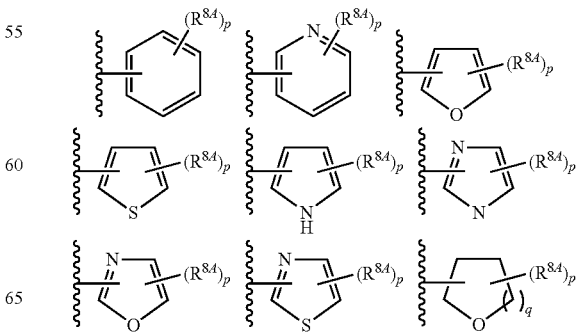

wherein $R_c$ and $R_6$ are independently hydrogen or substituted or unsubstituted alkyl; $R_7$ is a substituted or unsubstituted, linear or branched, cyclic or acyclic lower alkyl moiety; $R_8$ is a substituted or unsubstituted carbocyclic, heterocyclic, aryl or heteroaryl moiety; and Alk is a bond or a substituted or unsubstituted $C_{1-6}$alkylene or $C_{2-6}$alkenylene chain wherein up to two non-adjacent methylene units are independently optionally replaced by CO, $CO_2$, COCO, $CONR^{Z1}$, $OCONR^{Z1}$, $NR^{Z1}NR^{Z2}$, $NR^{Z1}NR^{Z2}CO$, $NR^{Z1}CO$, $NR^{Z1}CO_2$, $NR^{Z1}CONR^{Z2}$, SO, $SO_2$, $NR^{Z1}SO_2$, $SO_2NR^{Z1}$, $NR^{Z1}SO_2NR^{Z2}$, O, S, or $NR^{Z1}$; wherein each occurrence of $R^{Z1}$ and $R^{Z2}$ is independently hydrogen, alkyl, heteroalkyl, aryl, heteroaryl or acyl; and $R_8$ is a substituted or unsubstituted alkyl, heteroalkyl, cycloalkyl, heterocycloalkyl, aryl or heteroaryl moiety. In certain embodiments, $R_6$ and $R_7$ are independently lower alkyl. In certain other embodiments, $R_6$ is lower alkyl. In certain exemplary embodiments, $R_6$ is methyl. In certain embodiments, $R_c$ is hydrogen. In certain other embodiments, Alk is a $C_3$ alkylene moiety. In yet other embodiments, $R_8$ is one of:

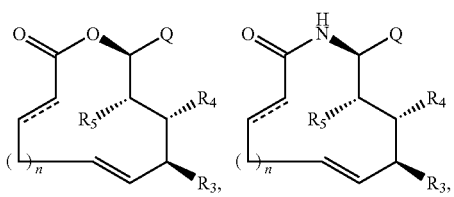

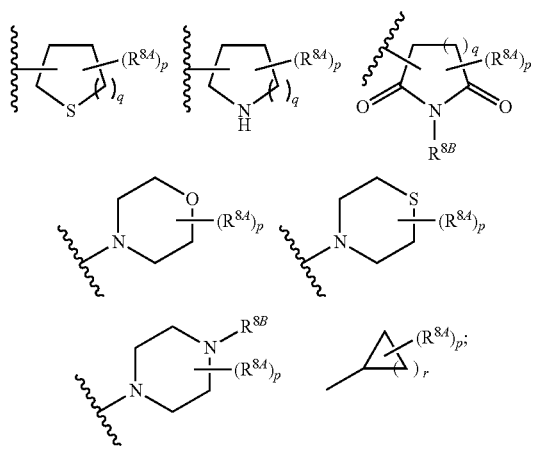

wherein p is an integer from 0 to 5; q is 1 or 2, r is an integer from 1 to 6; each occurrence of $R^{8A}$ is independently hydrogen, alkyl, heteroalkyl, aryl, heteroaryl, -(alkyl)aryl or -(alkyl)heteroaryl, —$OR^{8C}$, —$SR^{8C}$, $N(R^{8C})_2$, —$SO_2N(R^{8C})_2$, —(C=O)$N(R^{8C})_2$, halogen, —CN, —$NO_2$, —(C=O)$OR^{8C}$, —$N(R^{8C})$(C=O)$R^{8D}$, wherein each occurrence of $R^{8C}$ and $R^{8D}$ is independently hydrogen, lower alkyl, lower heteroalkyl, aryl, heteroaryl, -(alkyl)aryl or -(alkyl)heteroaryl; and each occurrence of $R^{8B}$ is independently hydrogen or lower alkyl. In certain exemplary embodiments, $R_8$ has the structure:

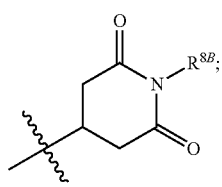

wherein $R^{8B}$ is hydrogen or lower alkyl. In certain exemplary embodiments, $R^{8B}$ is hydrogen. In certain exemplary embodiments, Q has the following stereochemistry:

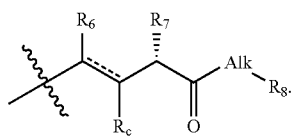

II) Compounds of the Formula (and Pharmaceutically Acceptable Derivatives Thereof):

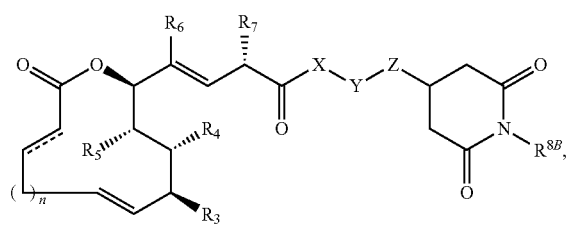

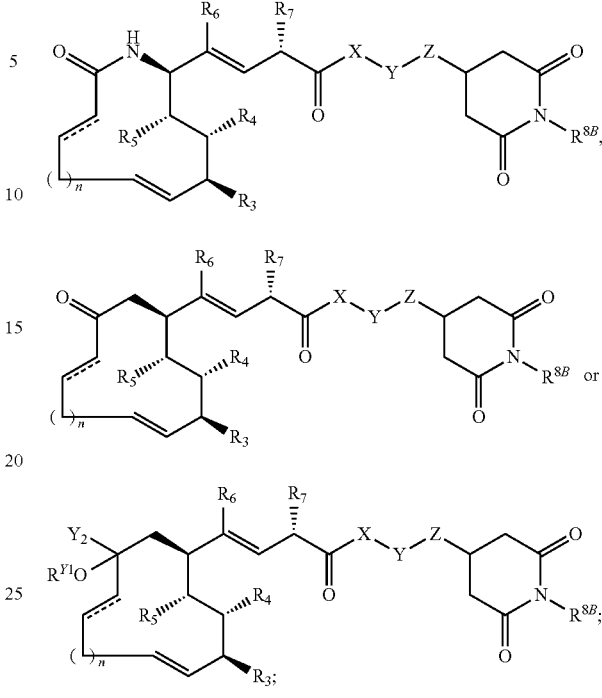

wherein n, $R_3$-$R_5$ are as defined in classes and subclasses herein; $Y_2$ and $R^{Y1}$ are independently hydrogen or lower alkyl; $R_6$ is hydrogen or lower alkyl; $R_7$ is a substituted or unsubstituted, linear or branched, cyclic or acyclic lower alkyl moiety; $R^{8B}$ is hydrogen or lower alkyl; and X, Y and Z are independently a bond, —O—, —S—, —C(=O)—, —$NR^{Z1}$, —$CHOR^{Z1}$, —$CHNR^{Z1}R^{Z2}$, C=S, C=$N(R^{Z1})$ or —CH(Hal); or a substituted or unsubstituted $C_{1-6}$alkylene or $C_{2-6}$alkenylene chain wherein up to two non-adjacent methylene units are independently optionally replaced by CO, $CO_2$, COCO, $CONR^{Z1}$, $OCONR^{Z1}$, $NR^{Z1}NR^{Z2}$, $NR^{Z1}NR^{Z2}CO$, $NR^{Z1}CO$, $NR^{Z1}CO_2$, $NR^{Z1}CONR^{Z2}$, SO, $SO_2$, $NR^{Z1}SO_2$, $SO_2NR^{Z1}$, $NR^{Z1}SO_2NR^{Z2}$, O, S, or $NR^{Z1}$; wherein Hal is a halogen selected from F, Cl, Br and I; and each occurrence of $R^{Z1}$ and $R^{Z2}$ is independently hydrogen, alkyl, heteroalkyl, aryl, heteroaryl or acyl; or $R^{Z1}$ and $R^{Z2}$, taken together with the nitrogen atom to which they are attached, for a heterocyclic or heteroaryl moiety; and pharmaceutically acceptable derivatives thereof. In certain other embodiments, $R_6$ is lower alkyl. In certain exemplary embodiments, $R_6$ is methyl. In certain other embodiments, $R_7$ is methyl. In certain other embodiments, X and Z are each $CH_2$ and Y is —CHOH, —$CHNH_2$ or —CHF. In certain other embodiments, $R^{8B}$ is hydrogen, methyl or ethyl.

In certain embodiments, for compounds of class II above, —X—Y—Z together represents the moiety —$CH_2$—Y—$CH_2$—; wherein Y is —$CHOR^{Z1}$, —$CHNR^{Z1}R^{Z2}$, C=O, C=S, C=$N(R^{Z1})$ or —CH(Hal); wherein Hal is a halogen selected from F, Cl, Br and I; and $R^{Z1}$ and $R^{Z2}$ are independently hydrogen, alkyl, heteroalkyl, aryl, heteroaryl or acyl, or $R^{Z1}$ and $R^{Z2}$, taken together with the nitrogen atom to which they are attached, for a heterocyclic or heteroaryl moiety.

III) Compounds of the Formula (and Pharmaceutically Acceptable Derivatives thereof):

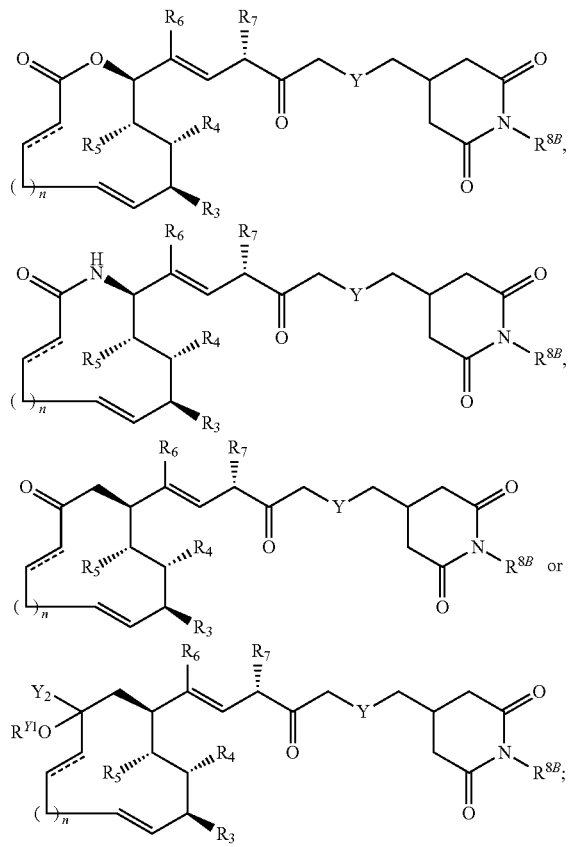

wherein n, $R_3$-$R_5$ are as defined in classes and subclasses herein; $Y_2$ and $R^{Y1}$ are independently hydrogen or lower alkyl; $R_6$ is hydrogen or lower alkyl; $R_7$ is a substituted or unsubstituted, linear or branched, cyclic or acyclic lower alkyl moiety; $R^{8B}$ is hydrogen or lower alkyl; and Y is —CHOR$^{Y2}$, —CHNR$^{Y2}$R$^{Y3}$, C=O, C=S, C=N(R$^{Y2}$) or —CH(Hal); wherein Hal is a halogen selected from F, Cl, Br and I; and R$^{Y2}$ and R$^{Y3}$ are independently hydrogen, alkyl, heteroalkyl, aryl, heteroaryl or acyl, or R$^{Y2}$ and R$^{Y3}$, taken together with the nitrogen atom to which they are attached, for a heterocyclic or heteroaryl moiety. In certain other embodiments, $R_6$ is lower alkyl. In certain exemplary embodiments, $R_6$ is methyl. In certain other embodiments, $R_7$ is methyl. In certain other embodiments, Y is —CHOH, —CHNH$_2$ or —CHF. In certain other embodiments, $R^{8B}$ is hydrogen, methyl or ethyl.

IV) Compounds of the Formula (and Pharmaceutically Acceptable Derivatives thereof):

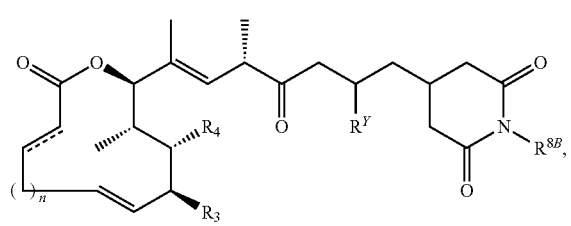

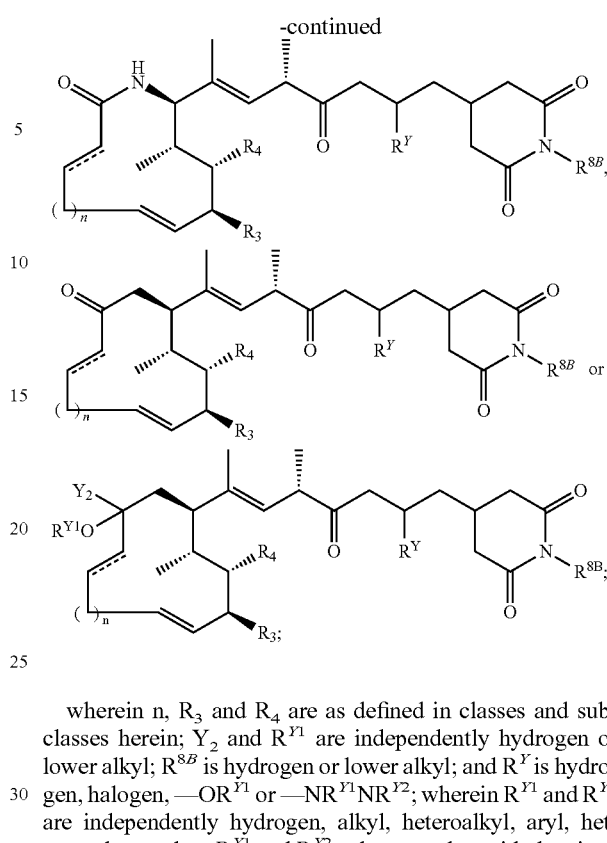

wherein n, $R_3$ and $R_4$ are as defined in classes and subclasses herein; $Y_2$ and $R^{Y1}$ are independently hydrogen or lower alkyl; $R^{8B}$ is hydrogen or lower alkyl; and $R^Y$ is hydrogen, halogen, —OR$^{Y1}$ or —NR$^{Y1}$NR$^{Y2}$; wherein R$^{Y1}$ and R$^{Y2}$ are independently hydrogen, alkyl, heteroalkyl, aryl, heteroaryl or acyl, or R$^{Y1}$ and R$^{Y2}$, taken together with the nitrogen atom to which they are attached, for a heterocyclic or heteroaryl moiety.

In certain other embodiments, $R^Y$ is OH, NH$_2$ or halogen (e.g., F). In certain other embodiments, $R^{8B}$ is hydrogen, methyl or ethyl.

V) Compounds of the Formula (and Pharmaceutically Acceptable Derivatives Thereof):

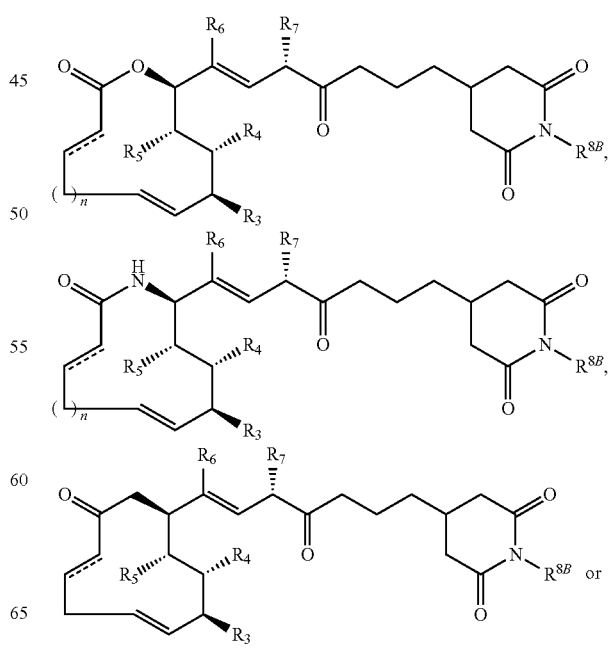

-continued

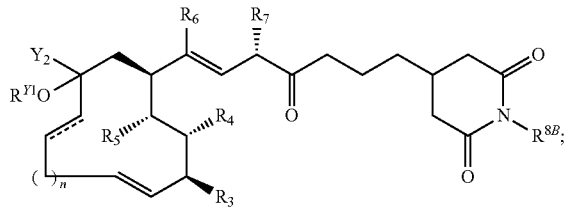

wherein n, $R_3$-$R_5$ are as defined in classes and subclasses herein; $Y_2$ and $R^{Y1}$ are independently hydrogen or lower alkyl; $R_6$ is hydrogen or lower alkyl; $R_7$ is a substituted or unsubstituted, linear or branched, cyclic or acyclic lower alkyl moiety; and $R^{8B}$ is hydrogen or lower alkyl. In certain other embodiments, $R_6$ is lower alkyl. In certain exemplary embodiments, $R_6$ is methyl. In certain other embodiments, $R_7$ is methyl. In certain other embodiments, $R^{8B}$ is hydrogen, methyl or ethyl.

VI) Compounds of the Formula (and Pharmaceutically Acceptable Derivatives Thereof):

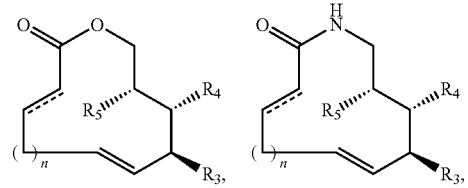

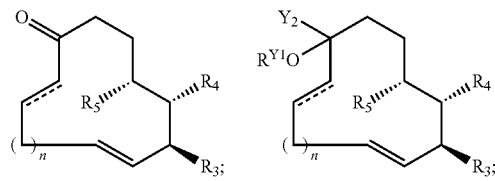

wherein n, $R_3$-$R_5$ are as defined in classes and subclasses herein; and $Y_2$ and $R^{Y1}$ are independently hydrogen or lower alkyl.

VII) Compounds of the Formula (and Pharmaceutically Acceptable Derivatives Thereof):

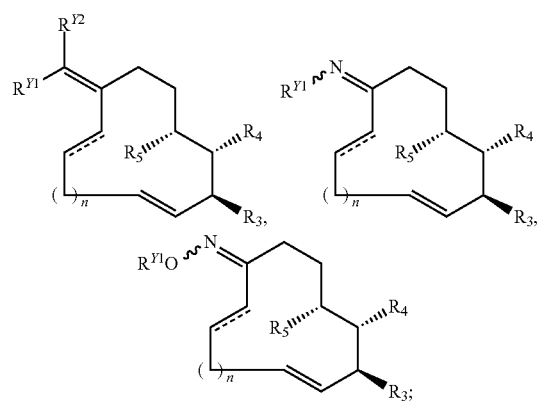

-continued

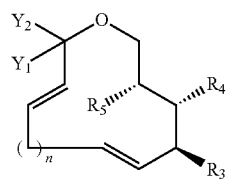

wherein n, $R_3$-$R_5$ are as defined in classes and subclasses herein; and $R^{Y1}$ and $R^{Y2}$ are independently hydrogen or lower alkyl.

VIII) Compounds of the Formula (and Pharmaceutically Acceptable Derivatives Thereof):

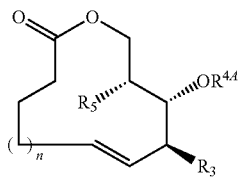

wherein n, $R_3$-$R_5$ are as defined in classes and subclasses herein; and $Y_1$ and $Y_2$ are independently hydrogen, or $C(R^{Y1})_3$; wherein each occurrence of $R^{Y1}$ is independently hydrogen or alkyl. In certain other embodiments, $R_5$ is H or lower alkyl. In yet other embodiments, $R_4$ is OH. In certain exemplary embodiments, $Y_1$ and $Y_2$ are each hydrogen; $R_5$ is H or lower alkyl; $R_4$ is OH; and $R_3$ is alkoxy. In certain exemplary embodiments, $Y_1$ and $Y_2$ are each hydrogen; $R_5$ is methyl; $R_4$ is OH; and $R_3$ is methoxy.

IX) Compounds of the Formula (and Pharmaceutically Acceptable Derivatives Thereof):

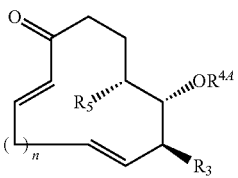

wherein n, $R_3$ and $R_5$ are as defined in classes and subclasses herein, and $R^{44}$ is hydrogen or lower alkyl. In certain other embodiments, $R_5$ is H or lower alkyl. In yet other embodiments, $R^{44}$ is H. In certain exemplary embodiments, $R_5$ is H or lower alkyl; $R^{44}$ is H; and $R_3$ is methoxy.

A Compounds of the Formula (and Pharmaceutically Acceptable Derivatives Thereof):

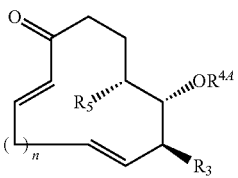

wherein n, $R_3$ and $R_5$ are as defined in classes and subclasses herein, and $R^{44}$ is hydrogen or lower alkyl. In certain other embodiments, $R_5$ is H or lower alkyl. In yet other embodiments, $R^{44}$ is H. In certain exemplary embodiments, $R_5$ is H or lower alkyl; $R^{44}$ is H; and $R_3$ is methoxy.

XI) Compounds of the Formula (and Pharmaceutically Acceptable Derivatives Thereof):

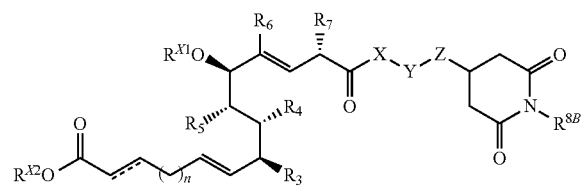

wherein n, $R_3$-$R_5$, $R^{X1}$, $R^{X2}$ and Q are as defined in classes and subclasses herein, $R_6$ is hydrogen or lower alkyl; $R_7$ is a substituted or unsubstituted, linear or branched, cyclic or acyclic lower alkyl moiety; $R^{8B}$ is hydrogen or lower alkyl; and X, Y and Z are independently a bond, —O—, —S—, —C(=O)—, —NR$^{Z1}$—, —CHOR$^{Z1}$, —CHNR$^{Z1}$R$^{Z2}$, C=S, C=N(R$^{Z1}$) or —CH(Hal); or a substituted or unsubstituted $C_{1-6}$alkylene or $C_{2-6}$alkenylene chain wherein up to two non-adjacent methylene units are independently optionally replaced by CO, CO$_2$, COCO, CONR$^{Z1}$, OCONR$^{Z1}$, NR$^{Z1}$NR$^{Z2}$, NR$^{Z1}$NR$^{Z2}$CO, NR$^{Z1}$CO, NR$^{Z1}$CO$_2$, NR$^{Z1}$CONR$^{Z2}$, SO, SO$_2$, NR$^{Z1}$SO$_2$, SO$_2$NR$^{Z1}$, NR$^{Z1}$SO$_2$NR$^{Z2}$, O, S, or NR$^{Z1}$; wherein Hal is a halogen selected from F, Cl, Br and I; and each occurrence of R$^{Z1}$ and R$^{Z2}$ is independently hydrogen, alkyl, heteroalkyl, aryl, heteroaryl or acyl; or R$^{Z1}$ and R$^{Z2}$, taken together with the nitrogen atom to which they are attached, for a heterocyclic or heteroaryl moiety; and pharmaceutically acceptable derivatives thereof. In certain other embodiments, $R_6$ is lower alkyl. In certain exemplary embodiments, $R_6$ is methyl. In certain other embodiments, $R_7$ is methyl. In certain other embodiments, X and Z are each CH$_2$ and Y is —CHOH, —CHNH$_2$ or —CHF. In certain other embodiments, $R^{8B}$ is hydrogen, methyl or ethyl.

In certain embodiments, for compounds of class X$^1$ above, —X—Y—Z together represents the moiety —CH$_2$—Y—CH$_2$—; wherein Y is —CHOR$^{Z1}$, —CHNR$^{Z1}$R$^{Z2}$, C=O, C=S, C=N(R$^{Z1}$) or —CH(Hal); wherein Hal is a halogen selected from F, Cl, Br and I; and R$^{Z1}$ and R$^{Z2}$ are independently hydrogen, alkyl, heteroalkyl, aryl, heteroaryl or acyl, or R$^{Z1}$ and R$^{Z2}$, taken together with the nitrogen atom to which they are attached, for a heterocyclic or heteroaryl moiety.

In certain embodiments, compounds of class XI above have the following structure:

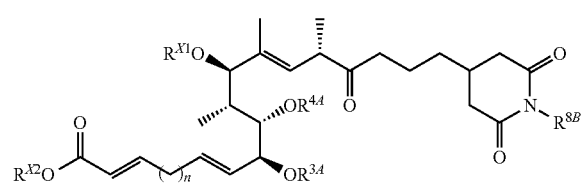

wherein $R^{X1}$, $R^{X2}$, $R^{8B}$ are as defined in classes and subclasses herein; $R^{4A}$ and $R^{3A}$ are independently hydrogen, lower alkyl or an oxygen protecting group; and n is 2.

In certain embodiments, for the compounds of subgroups I-XI described above, $R_3$ is hydroxyl, lower alkoxy or acyloxy. In certain exemplary embodiments, $R_3$ is methoxy.

In certain embodiments, for the compounds of subgroups I-III, V-VIII described above, $R_5$ is lower alkyl. In certain exemplary embodiments, $R_5$ is methyl. In certain embodiments, $R^4$ is halogen, hydroxyl, lower alkoxy, acyloxy or NR$^{4A}$R$^{4B}$, wherein R$^{4A}$ and R$^{4B}$ are independently hydrogen, lower alkyl, aryl, acyl or a nitrogen protecting group, or R$^{4A}$ and R$^{4B}$, taken together with the nitrogen atom to which they are attached, form a substituted or unsubstituted heterocyclic or heteroaryl moiety; or $R_4$, taken together with the carbon atom to which it is attached forms a moiety having the structure:

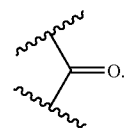

In certain embodiments, $R_4$ is a halogen selected from fluorine, chlorine, bromine and iodine. In certain exemplary embodiments, $R_4$ is fluorine. In certain other embodiments, $R_4$ is F, OH, OAc, NH$_2$ or $R_4$, taken together with the carbon atom to which it is attached forms a moiety having the structure:

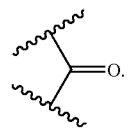

In certain embodiments, for the compounds of subgroup IV described above, $R_3$ is hydrogen, lower alkyl or an oxygen protecting group. In certain exemplary embodiments, $R_3$ is methoxy. In certain embodiments, $R_4$ is halogen, hydroxyl, lower alkoxy, acyloxy or NR$^{4A}$R$^{4B}$, wherein R$^{4A}$ and R$^{4B}$ are independently hydrogen, lower alkyl, aryl, acyl or a nitrogen protecting group, or R$^{4A}$ and R$^{4B}$, taken together with the nitrogen atom to which they are attached, form a substituted or unsubstituted heterocyclic or heteroaryl moiety; or $R_4$, taken together with the carbon atom to which it is attached forms a moiety having the structure

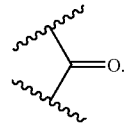

In certain embodiments, $R_4$ is a halogen selected from fluorine, chlorine, bromine and iodine. In certain exemplary embodiments, $R_4$ is fluorine. In certain other embodiments, $R_4$ is F, OH, OAc, NH$_2$ or $R_4$, taken together with the carbon atom to which it is attached forms a moiety having the structure:

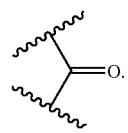

In certain embodiments, for the compounds of subgroups I-VI described above, $Y_2$ is hydrogen or lower alkyl substituted with one or more halogen atoms selected from F, Cl, Br and I. In certain exemplary embodiments, $Y_2$ is hydrogen or methyl substituted with one or more halogen atoms selected from F, Cl, Br and I. In certain exemplary embodiments, $Y_2$ is hydrogen or $CF_3$. In certain exemplary embodiments, $R^{Y1}$ is hydrogen or lower alkyl. In certain exemplary embodiments, $R^{Y1}$ is hydrogen or methyl. In certain exemplary embodiments, $Y_2$ is $CF_3$ and $R^{Y1}$ is methyl.

It will also be appreciated that for each of the subgroups I-IX described above, a variety of other subclasses are of special interest, including, but not limited to those classes described above i)-cl) and classes, subclasses and species of compounds described above and in the examples herein.

Some of the foregoing compounds can comprise one or more asymmetric centers, and thus can exist in various isomeric forms, e.g., stereoisomers and/or diastereomers. Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of stereoisomers or diastereomers are provided.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds of the invention and one or more pharmaceutically acceptable excipients or additives.

Compounds of the invention may be prepared by crystallization of compound of formula (I) under different conditions and may exist as one or a combination of polymorphs of compound of general formula (I) forming part of this invention. For example, different polymorphs may be identified and/or prepared using different solvents, or different mixtures of solvents for recrystallization; by performing crystallizations at different temperatures; or by using various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffractogram and/or other techniques. Thus, the present invention encompasses inventive compounds, their derivatives, their tautomeric forms, their stereoisomers, their polymorphs, their pharmaceutically acceptable salts their pharmaceutically acceptable solvates and pharmaceutically acceptable compositions containing them.

As discussed above, this invention provides novel compounds with a range of biological properties. Preferred compounds of this invention have biological activities relevant for the treatment of cancer and angiogenesis-related disorders.

Compounds of this invention include those specifically set forth above and described herein, and are illustrated in part by the various classes, subgenera and species disclosed elsewhere herein.

Additionally, the present invention provides pharmaceutically acceptable derivatives of the inventive compounds, and methods of treating a subject using these compounds, pharmaceutical compositions thereof, or either of these in combination with one or more additional therapeutic agents. Certain compounds of the present invention are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference. Furthermore, it will be appreciated by one of ordinary skill in the art that the synthetic methods, as described herein, utilize a variety of protecting groups. It will be appreciated that the compounds, as described herein, may be substituted with any number of substituents or functional moieties.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a prodrug or other adduct or derivative of a compound of this invention which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in *J. Pharmaceutical Sciences*, 66: 1-19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moeity advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of the compounds of the present invention which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

2) Synthetic Methodology

In another aspect, the present invention provides methods for preparing novel macrocycles having formula (I) a described above and in certain classes and subclasses herein. An overview of exemplary synthetic approaches to the inventive compounds is provided below, as detailed in Schemes 1-12, and in the Exemplification herein. It will be appreciated that the methods as described herein can be applied to each of the compounds as disclosed herein and equivalents thereof. Additionally, the reagents and starting materials are well known to those skilled in the art. Although the following schemes describe certain exemplary compounds, it will be appreciated that the use of alternate starting materials will yield other analogs of the invention. For example, compounds are described below where $X_1$ is O; however, it will be appreciated that alternate starting materials and/or intermediates can be utilized to generate compounds where $X_1$ is NH, N-alkyl, S, $CH_2$, etc.

In certain embodiments, compounds as provided herein, for example those where $X_1$ is O, and $R_1$ and $R_2$ are each hydrogen, are prepared from ring-closing metathesis of intermediate A, as depicted in Scheme 1A below:

Scheme 1A

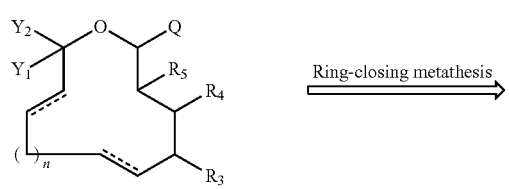

Ring-closing metathesis

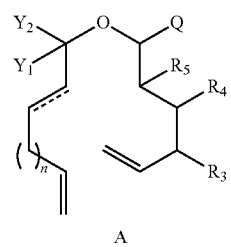

A

Compounds of formula I where Q is hydrogen and $Y_1$ and $Y_2$ together with the carbon atom to which they are attached form a C=O (e.g., isomigrastatin esters and amides) may be prepared by ring-closing metathesis of a suitable diene intermediate as shown in Scheme 2:

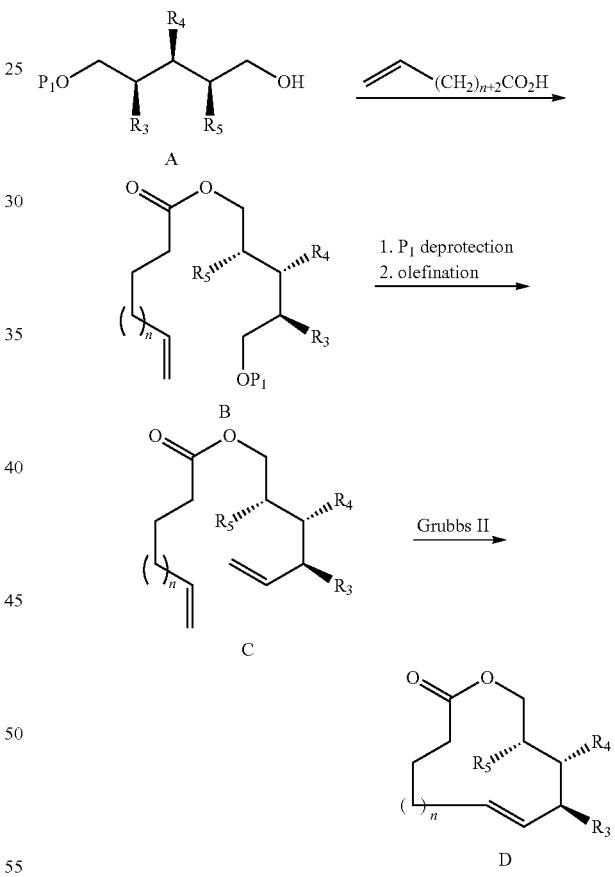

n = 1-4

Coupling of alcohol A with a suitable carboxyl olefin under suitable conditions leads to the formation of ester B. Removal of the P1 protecting group, followed by transformation of the resulting primary alcohol into a terminal olefin (e.g., Tebbe reagent) yields diene C. Ring-closing metathesis of C leads to isomigrastatin ester analog D.

Isomigrastatin amide analogs may be obtained in a similar approach, as depicted in Scheme 3.

Scheme 3

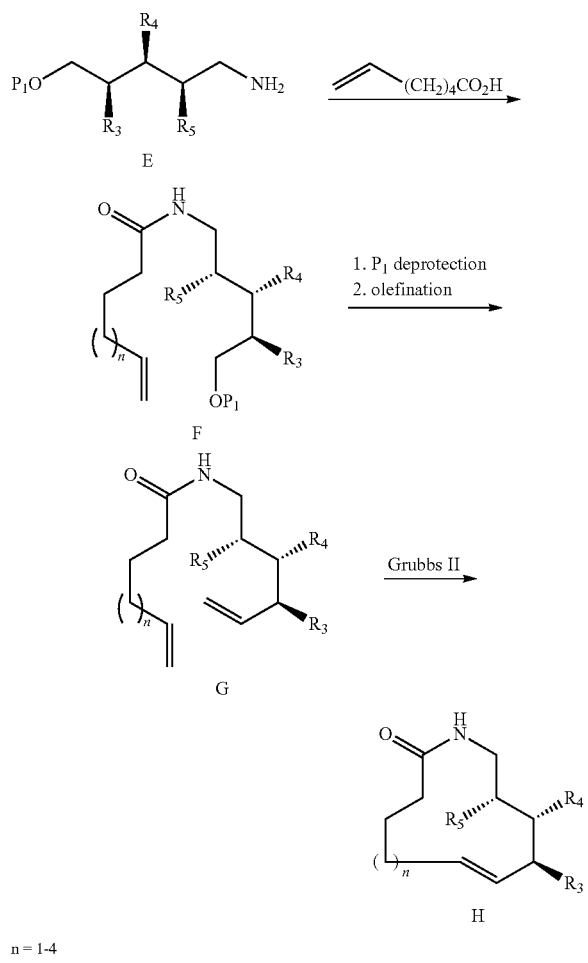

n = 1-4

An exemplary synthesis of isomigrastatin ester analog 22 using the above approach is illustrated in Schemes 4-6.

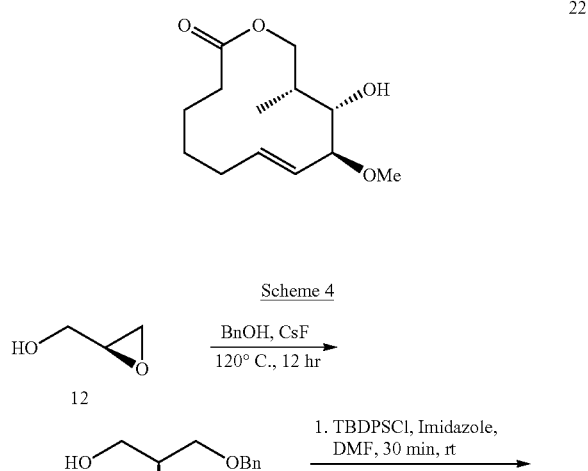

Scheme 4

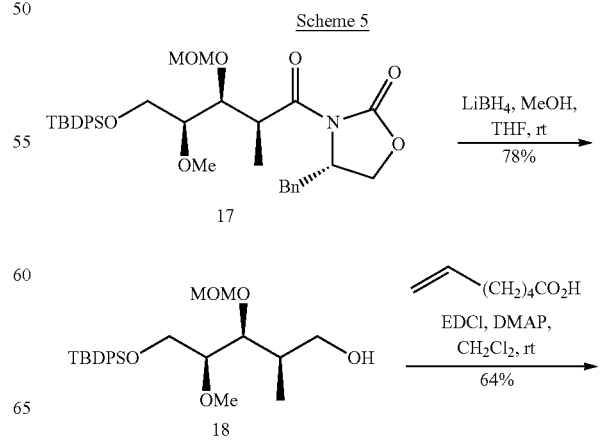

Aldehyde 15 was prepared from commercially available (S)-glycidol following the reported procedure and was used for the auxiliary mediated aldol to afford 16, and thereby installing three contiguous stereocenters in the required fashion (Scheme 4). Protection of the alcohol functionality of 16 using MOMCl followed by cleavage of auxiliary provided the primary alcohol in 78% yield (Scheme 5). Esterification of 18 with heptenoic proceeded smoothly under the influence of EDCI. Deprotection of TBDPS group followed by a two step operation (oxidation of the primary alcohol by Dess-Martin Periodinane and Tebbe Olefination of the resulting aldehde) provided the diene 20, and set the stage to test RCM to form the 12-membered lactone. Gratifyingly, under the influence of catalytic amount of Grubbs Ru-dihydroimidazolylidene in refluxing toluene macrolactone 21 was obtained as singe isomer. Removal of MOM was accomplished using TMSBr to afford the dihydro-isomigrastatin core in 60% yield.

Scheme 5

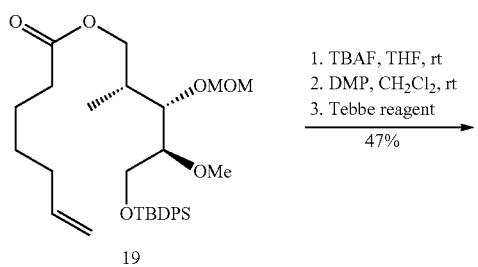

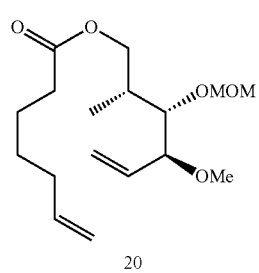

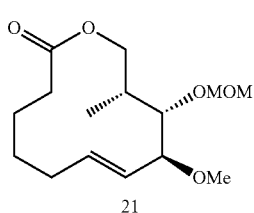

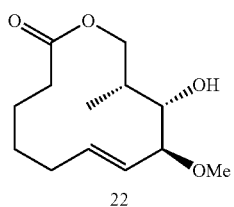

Although the strategy described above led to the core lactone in an efficient manner, we were still looking for more convergent strategy to streamline the synthesis.

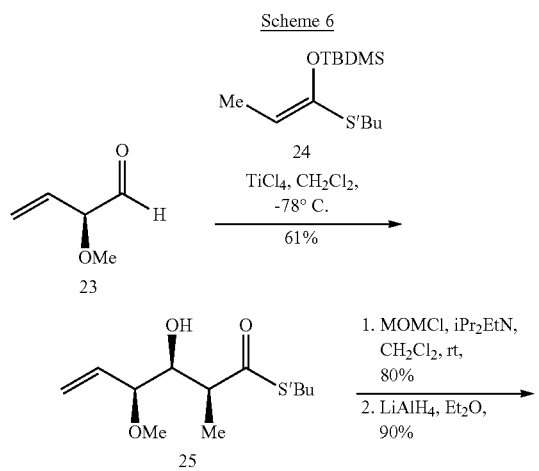

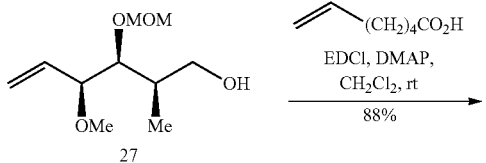

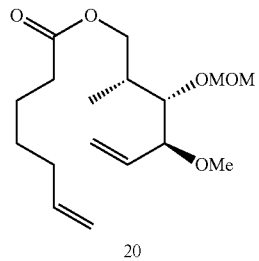

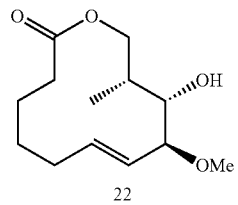

The Substrate-controlled aldol reaction of aldehyde 23 with enol ether 24 under the mediation of TiCl$_4$ afforded the 25 in 60% yield (Scheme 6). Protection of alcohol functionality with MOM followed by reduction of thio-ester to the primary alcohol provided primary alcohol 27 in 90% yield. Esterification with heptenoic acid proceeded smoothly to yield the previously encounter metathesis precursor 20 in an efficient manner, which was converted to the macro-lactone 22 following the reaction sequences described in scheme 3.

Compounds of formula I where Q is hydrogen and Y$_1$ and Y$_2$ are each hydrogen (e.g., isomigrastatin ethers) may be prepared by ring-closing metathesis of a suitable diene intermediate as shown in Scheme 7. The interest of these types of compounds is that they are likely to have better plasma stability than their ester counterparts.

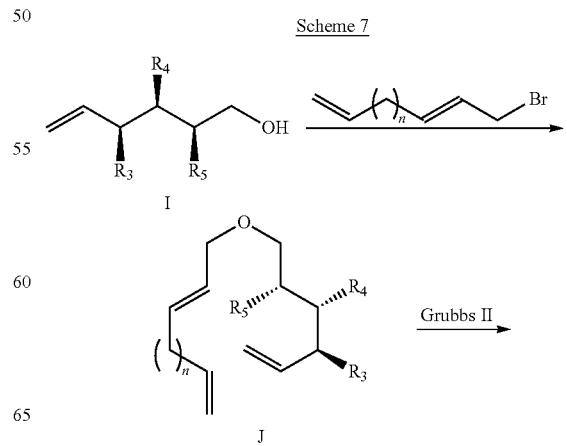

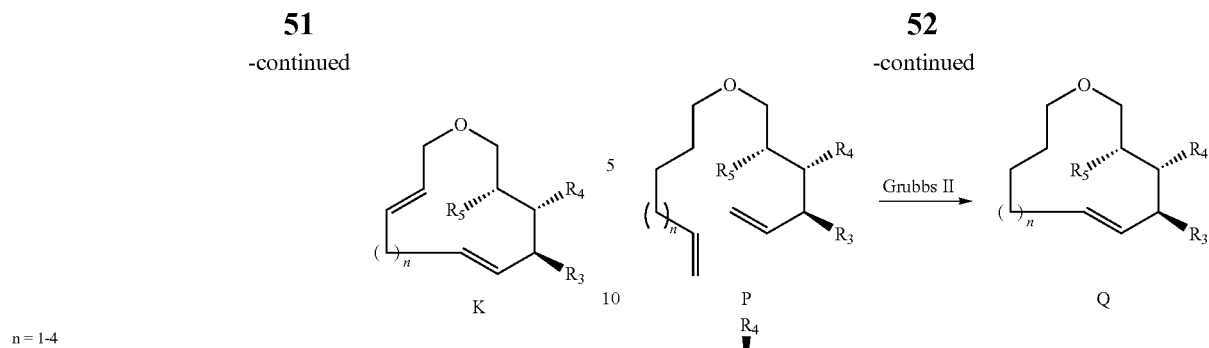

Coupling of alcohol I with a suitable dienyl halide under suitable conditions leads to the formation of ether J. Ring-closing metathesis of the resulting triene yields isomigrastatin ether analog K.

Isomigrastatin amine analogs may be obtained in a similar approach, as depicted in Scheme 8.

Scheme 8

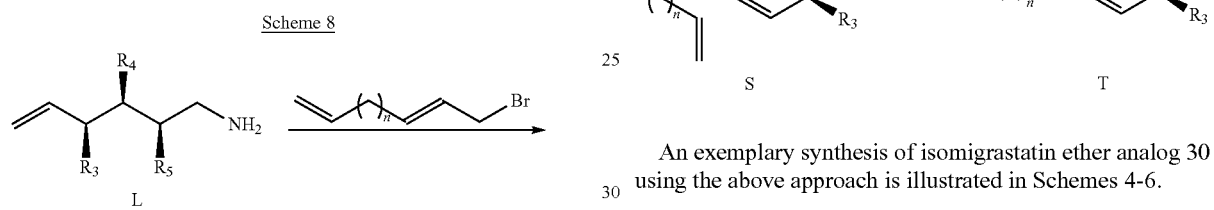

Analogs having one less degree of unsaturation may be obtained via an analogous approach, as shown in Scheme 9.

Scheme 9

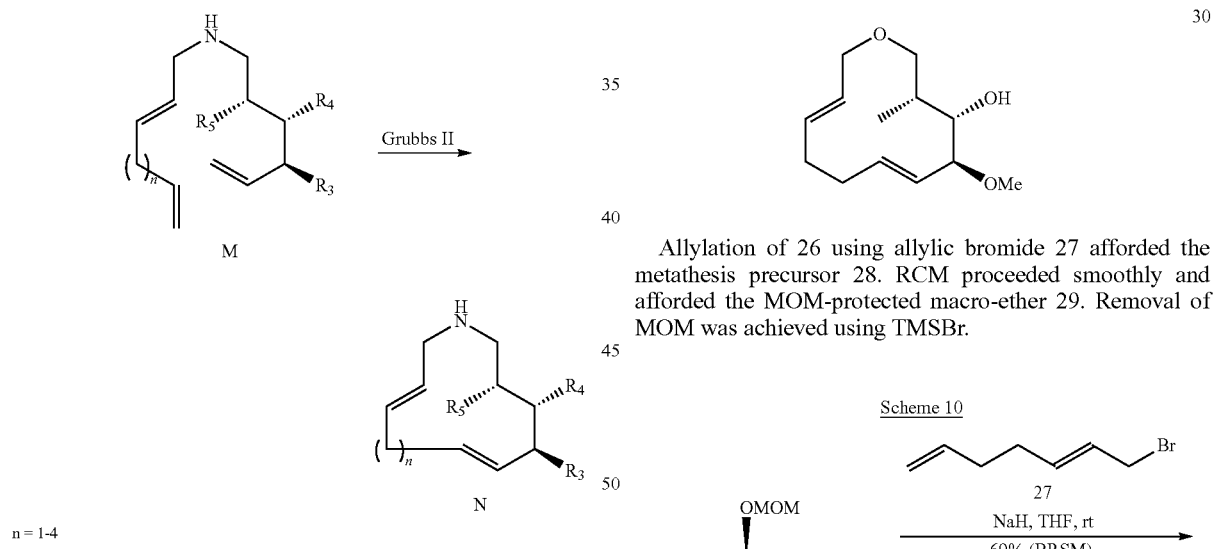

An exemplary synthesis of isomigrastatin ether analog 30 using the above approach is illustrated in Schemes 4-6.

Allylation of 26 using allylic bromide 27 afforded the metathesis precursor 28. RCM proceeded smoothly and afforded the MOM-protected macro-ether 29. Removal of MOM was achieved using TMSBr.

Scheme 10

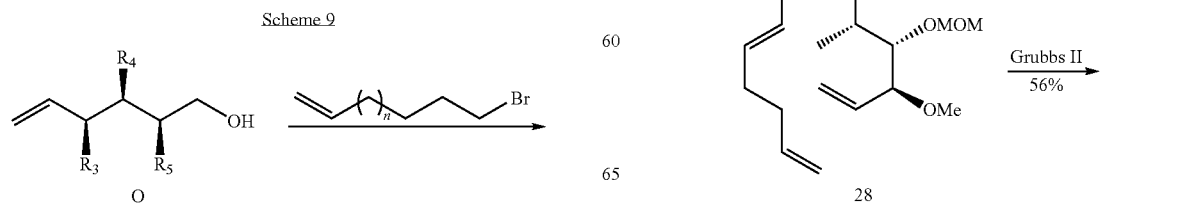

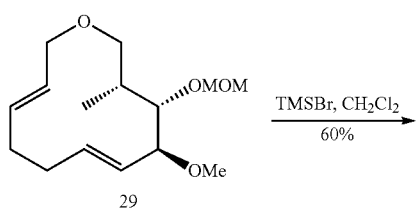

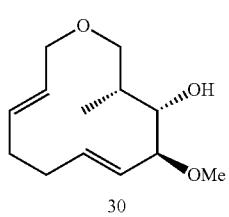

Compounds 21, 22 and 30 were investigated to evaluate their inhibitory potency against Ovcar3 ovarian cancer cells in chamber cell migration assays, wound healing assays and cell proliferation assays.

Compounds of formula I where Q is hydrogen, X1 is $CH_2$ and $Y_1$ and $Y_2$ together with the carbon atom to which they are attached form C=O (e.g., isomigrastatin macroketones) may be prepared by ring-closing metathesis of a suitable diene intermediate as shown in Scheme 11.

Scheme 11

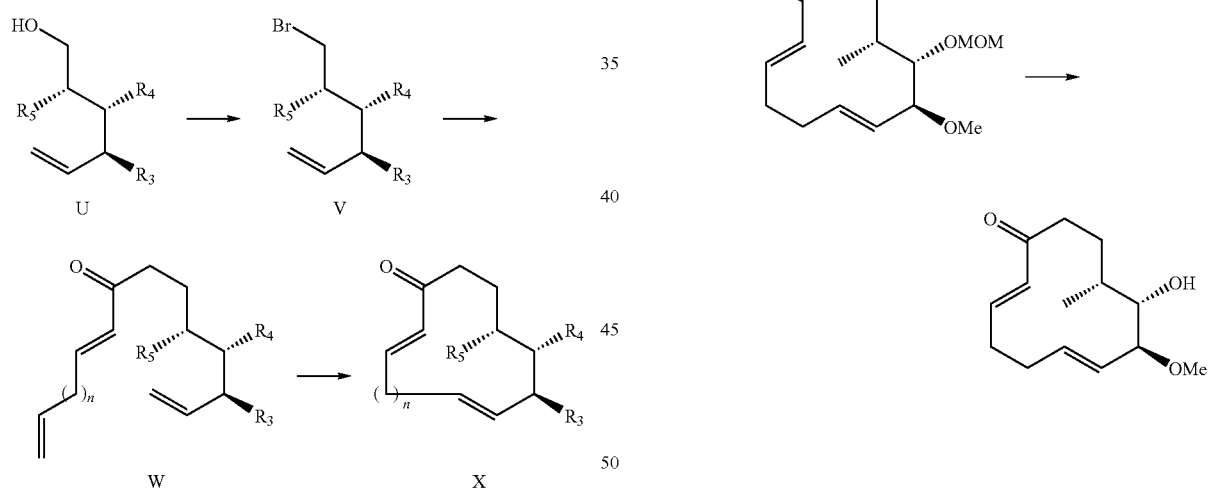

Transformation of alcohol U into the corresponding bromide, followed by coupling with a suitable diene reagent (e.g., Grignard) gives adduct W. Ring-closing metathesis of the resulting triene yields isomigrastatin ketone analog X. Scheme 12 depicts an exemplary synthesis of a methoxy hydroxy isomigrastatin macroketone.

Scheme 12

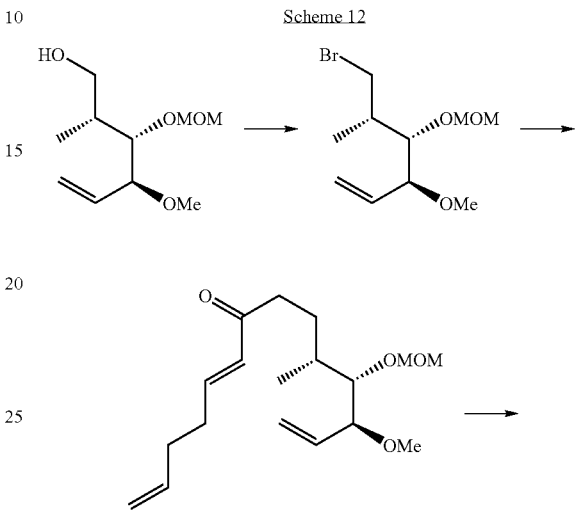

An exemplary synthesis of isomigrastatin is shown in Schemes 13 and 14.

Scheme 13

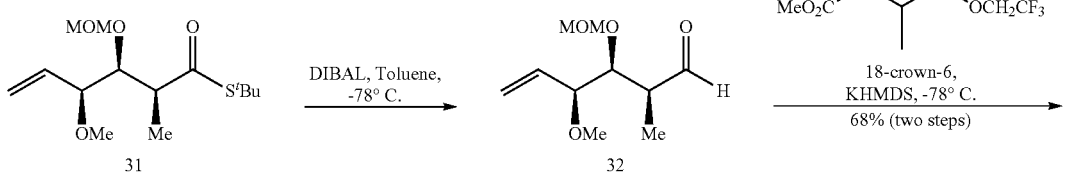

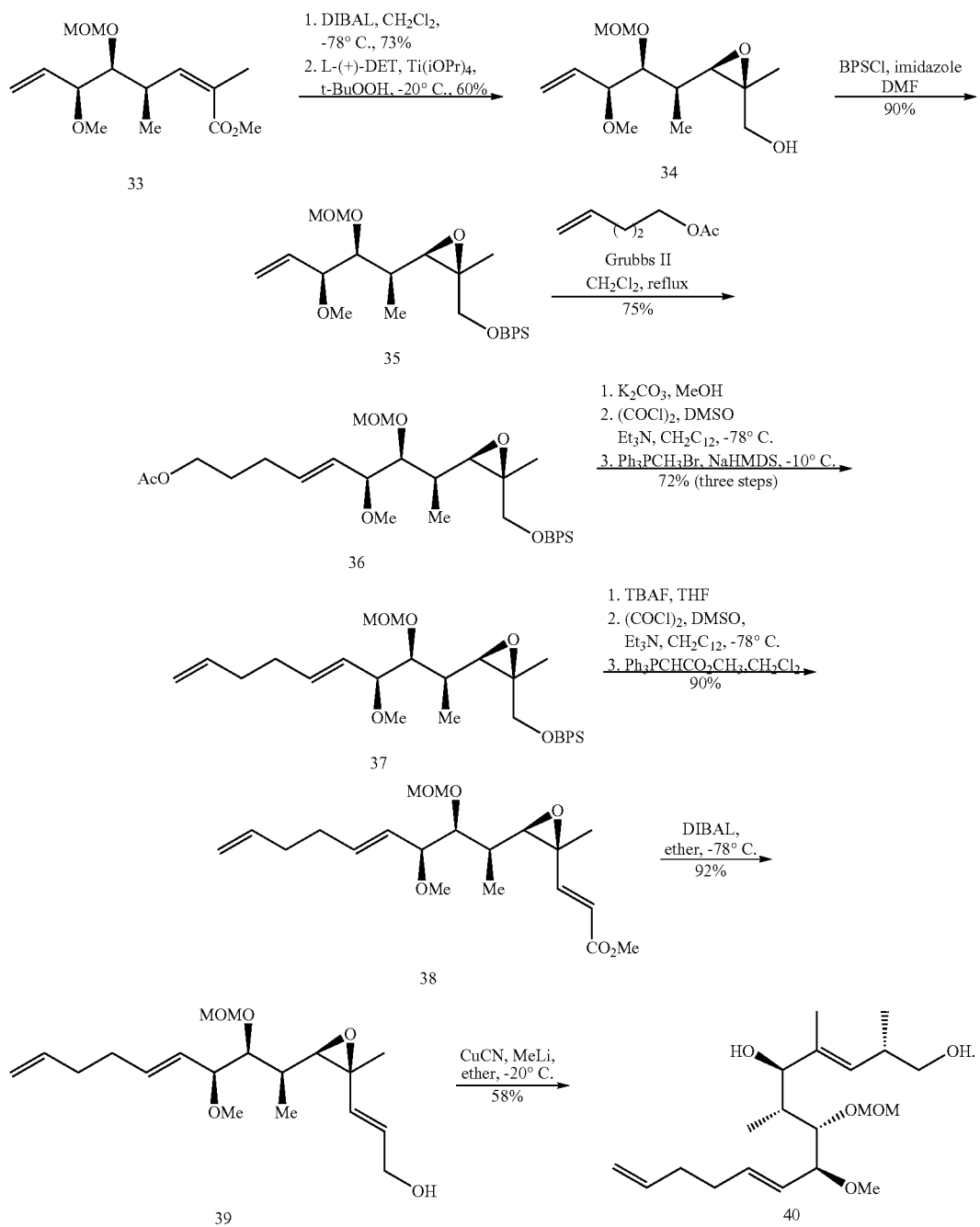
Scheme 14
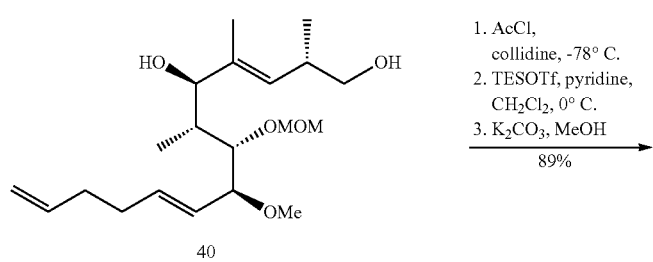

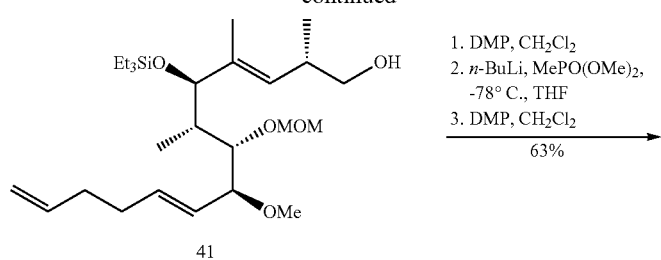
41
1. DMP, CH$_2$Cl$_2$
2. n-BuLi, MePO(OMe)$_2$, −78° C., THF
3. DMP, CH$_2$Cl$_2$
63%
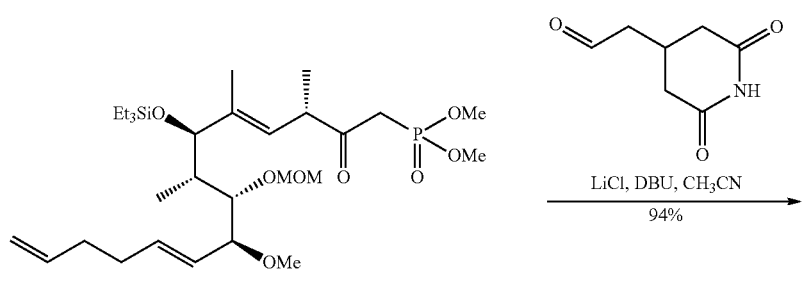
42
LiCl, DBU, CH$_3$CN
94%
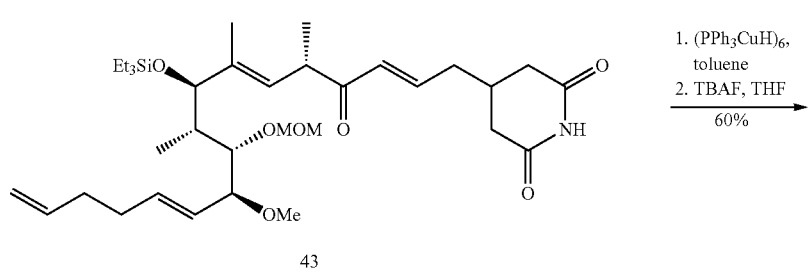
43
1. (PPh$_3$CuH)$_6$, toluene
2. TBAF, THF
60%
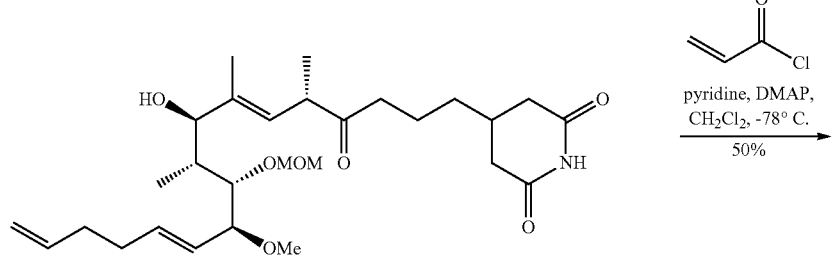
44
pyridine, DMAP, CH$_2$Cl$_2$, −78° C.
50%
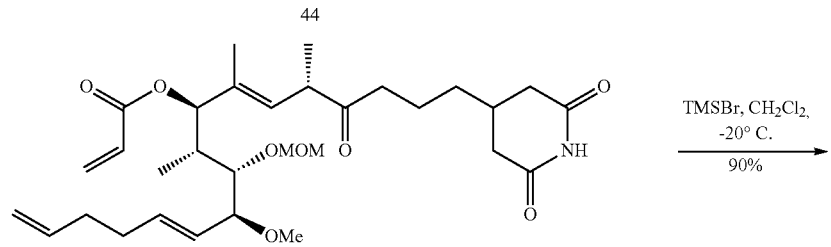
45
TMSBr, CH$_2$Cl$_2$, −20° C.
90%
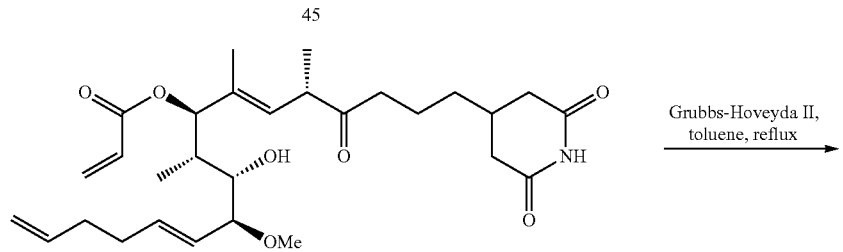
46
Grubbs-Hoveyda II, toluene, reflux -continued

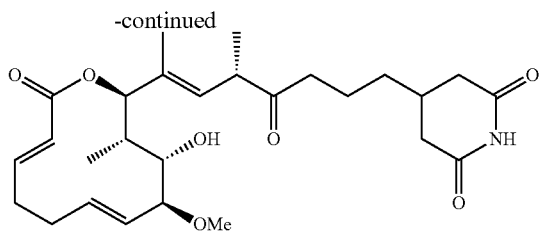

47
compound was seen by mass spec

Dorrigocin B (48) may be obtained by hydrolysis of 47.

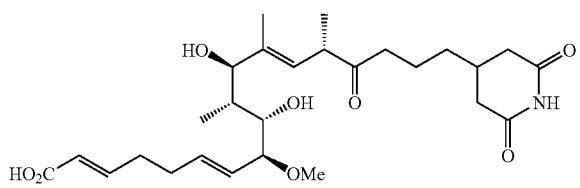

48

Other approaches to prepare inventive compounds will be readily apparent to the practitioner skilled in the relevant art.

Diversification:

It will also be appreciated that each of the components used in the synthesis of isomigrastatin analogues can be diversified either before synthesis or alternatively after the construction of the macrocycle. As used herein, the term "diversifying" or "diversify" means reacting an inventive compound (I) or any of the precursor fragments as defined herein (or any classes or subclasses thereof) at one or more reactive sites to modify a functional moiety or to add a functional moiety (e.g., nucleophilic addition of a substrate). Described generally herein are a variety of schemes to assist the reader in the synthesis of a variety of analogues, either by diversification of the intermediate components or by diversification of the macrocyclic structures as described herein, and classes and subclasses thereof. It will be appreciated that a variety of diversification reactions can be employed to generate novel analogues. As but a few examples, epoxidation and aziridation can be conducted to generate epoxide and aziridine analogues of compounds described herein. Additionally, addition across either double bond will generate additional diversity. In addition to diversification after macrocyclization, it will be understood that diversification can occur prior to macrocyclization (e.g., epoxidation, aziridation, reduction at a $C_{2-3}$ and/or $C_{12-13}$ double bond(s) could occur prior to metathesis ring-closure, or other means known in the art to effect macorcyclic ring closure, to describe just one example). For additional guidance available in the art, the practitioner is directed to "Advanced Organic Chemistry", March, J. John Wiley & Sons, 2001, $5^{th}$ ed., the entire contents of which are hereby incorporated by reference.

3) Pharmaceutical Compositions

In another aspect of the present invention, pharmaceutical compositions are provided, which comprise any one of the compounds described herein (or a prodrug, pharmaceutically acceptable salt or other pharmaceutically acceptable derivative thereof), and optionally comprise a pharmaceutically acceptable carrier, adjuvant or vehicle. In certain other embodiments, the compositions of the invention are useful for the treatment of cancer and disorders associated with metastasis and/or angiogenesis. In certain embodiments, the inventive compositions optionally further comprise one or more additional therapeutic agents. In certain other embodiments, the additional therapeutic agent is a cytotoxic agent, as discussed in more detail herein. In certain other embodiments, the additional therapeutic agent is an anticancer agent. In certain embodiments, the anticancer agent is an epothilone, taxol, radicicol or TMC-95A/B. In certain embodiments, the epothilone is 12,13-desoxyepothilone B, (E)-9,10-dehydro-12,13-desoxyEpoB and 26-CF3-(E)-9,10-dehydro-12,13-desoxyEpoB. Alternatively, a compound of this invention may be administered to a patient in need thereof in combination with the administration of one or more other therapeutic agents. For example, additional therapeutic agents for conjoint administration or inclusion in a pharmaceutical composition with a compound of this invention may be an antiangiogenesis agent or anticancer agent approved for the treatment of cancer, as discussed in more detail herein, or it may be any one of a number of agents undergoing approval in the Food and Drug Administration that ultimately obtain approval for the treatment of cancer.

As described above, the pharmaceutical compositions of the present invention additionally comprise a pharmaceutically acceptable carrier, adjuvant or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogenfree water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly (orthoesters) and poly(anhydrides). Depot injectable formulations are also prepared by entrapping the drug in liposomes or microemulsions, which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions, which can be used, include polymeric substances and waxes.

The present invention encompasses pharmaceutically acceptable topical formulations of inventive compounds. The term "pharmaceutically acceptable topical formulation", as used herein, means any formulation which is pharmaceutically acceptable for intradermal administration of a compound of the invention by application of the formulation to the epidermis. In certain embodiments of the invention, the topical formulation comprises a carrier system. Pharmaceutically effective carriers include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other carrier known in the art for topically administering pharmaceuticals. A more complete listing of art-known carriers is provided by reference texts that are standard in the art, for example, Remington's Pharmaceutical Sciences, 16th Edition, 1980 and 17th Edition, 1985, both published by Mack Publishing Company, Easton, Pa., the disclosures of which are incorporated herein by reference in their entireties. In certain other embodiments, the topical formulations of the invention may comprise excipients. Any pharmaceutically acceptable excipient known in the art may be used to prepare the inventive pharmaceutically acceptable topical formulations. Examples of excipients that can be included in the topical formulations of the invention include, but are not limited to, preservatives, antioxidants, moisturizers, emollients, buffering agents, solubilizing agents, other penetration agents, skin protectants, surfactants, and propellants, and/or additional therapeutic agents used in combination to the inventive compound. Suitable preservatives include, but are not limited to, alcohols, quaternary amines, organic acids, parabens, and phenols. Suitable antioxidants include, but are not limited to, ascorbic acid and its esters, sodium bisulfite, butylated hydroxytoluene, butylated hydroxyanisole, tocopherols, and chelating agents like EDTA and citric acid. Suitable moisturizers include, but are not limited to, glycerine, sorbitol, polyethylene glycols, urea, and propylene glycol. Suitable buffering agents for use with the invention include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates. Suitable skin protectants that can be used in the topical formulations of the invention include, but are not limited to, vitamin E oil, allatoin, dimethicone, glycerin, petrolatum, and zinc oxide.

In certain embodiments, the pharmaceutically acceptable topical formulations of the invention comprise at least a compound of the invention and a penetration enhancing agent. The choice of topical formulation will depend or several factors, including the condition to be treated, the physicochemical characteristics of the inventive compound and other excipients present, their stability in the formulation, available manufacturing equipment, and costs constraints. As used herein the term "penetration enhancing agent" means an agent capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, Percutaneous Penetration Enhancers, Maibach H. I. and Smith H. E. (eds.), CRC Press, Inc., Boca Raton, Fla. (1995), which surveys the use and testing of various skin penetration enhancers, and Buyuktimkin et al., Chemical Means of Transdermal Drug Permeation Enhancement in Transdermal and Topical Drug Delivery Systems, Gosh T. K., Pfister W. R., Yum S. I. (Eds.), Interpharm Press Inc., Buffalo Grove, Ill. (1997). In certain exemplary embodiments, penetration agents for use with the invention include, but are not limited to, triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate) and N-methylpyrrolidone.

In certain embodiments, the compositions may be in the form of ointments, pastes, creams, lotions, gels, powders, solutions, sprays, inhalants or patches. In certain exemplary embodiments, formulations of the compositions according to the invention are creams, which may further contain saturated or unsaturated fatty acids such as stearic acid, palmitic acid, oleic acid, palmito-oleic acid, cetyl or oleyl alcohols, stearic acid being particularly preferred. Creams of the invention may also contain a non-ionic surfactant, for example, polyoxy-40-stearate. In certain embodiments, the active component is admixed under sterile conditions with a pharmaceutically acceptable carrier, adjuvant or vehicle and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix or gel.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anticancer agent), or they may achieve different effects (e.g., control of any adverse effects).

For example, other therapies or therapeutic agents that may be used in combination with the inventive compounds of the present invention include surgery, radiotherapy (in but a few examples, γ-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. For a more comprehensive discussion of updated cancer therapies see, The Merck Manual, Seventeenth Ed. 1999, the entire contents of which are hereby incorporated by reference. See also the National Cancer Institute (CNI) website (www.nci.nih.gov) and the Food and Drug Administration (FDA) website for a list of the FDA approved oncology drugs (www.fda.gov/cder/cancer/druglistframe—See Appendix A).

In certain embodiments, the pharmaceutical compositions of the present invention further comprise one or more additional therapeutically active ingredients (e.g., chemotherapeutic and/or palliative). For purposes of the invention, the term "Palliative" refers to treatment that is focused on the relief of symptoms of a disease and/or side effects of a therapeutic regimen, but is not curative. For example, palliative treatment encompasses painkillers, antinausea medications and anti-sickness drugs. In addition, chemotherapy, radiotherapy and surgery can all be used palliatively (that is, to reduce symptoms without going for cure; e.g., for shrinking tumors and reducing pressure, bleeding, pain and other symptoms of cancer).

4) Research Uses, Pharmaceutical Uses and Methods of Treatment

Research Uses

According to the present invention, the inventive compounds may be assayed in any of the available assays known in the art for identifying compounds having antiangiogenic activity and/or antiproliferative activity. For example, the assay may be cellular or non-cellular, in vivo or in vitro, high- or low-throughput format, etc.

Thus, in one aspect, compounds of this invention which are of particular interest include those which:

exhibit activity as inhibitors of cell migration;

exhibit an antiproliferative and/or an antiangiogenic effect on solid tumors;

facilitate wound healing; and/or exhibit a favorable therapeutic profile (e.g., safety, efficacy, and stability).

As discussed above, certain of the compounds as described herein exhibit activity generally as inhibitors of cell migration and/or angiogenesis. More specifically, compounds of the invention act as inhibitors of tumor growth and angiogenesis.

As detailed in the exemplification herein, in assays to determine the ability of compounds to inhibit tumor cell migration (e.g., chamber cell migration assay), certain inventive compounds exhibited $IC_{50}$ values $\leq 50$ μM. In certain other embodiments, inventive compounds exhibit $IC_{50}$ values $\leq 40$ μM. In certain other embodiments, inventive compounds exhibited $IC_{50}$ values $\leq 30$ μM. In certain other embodiments, inventive compounds exhibited $IC_{50}$ values $\leq 20$ μM. In certain other embodiments, inventive compounds exhibited $IC_{50}$ values $\leq 10$ μM. In certain other embodiments, inventive compounds exhibited $IC_{50}$ values $\leq 7.5$ μM. In certain embodiments, inventive compounds exhibited $IC_{50}$ values $\leq 5$ μM. In certain other embodiments, inventive compounds exhibit $IC_{50}$ values $\leq 2.5$ μM. In certain embodiments, inventive compounds exhibit $IC_{50}$ values $\leq 1$ μM. In certain other embodiments, inventive compounds exhibit $IC_{50}$ values $\leq 750$ nM. In certain other embodiments, inventive compounds exhibit $IC_{50}$ values $\leq 500$ nM. In certain other embodiments, inventive compounds exhibit $IC_{50}$ values $\leq 250$ nM. In certain other embodiments, inventive compounds exhibit $IC_{50}$ values $\leq 100$ nM. In other embodiments, exemplary compounds exhibited $IC_{50}$ values $\leq 75$ nM. In other embodiments, exemplary compounds exhibited $IC_{50}$ values $\leq 50$ nM. In other embodiments, exemplary compounds exhibit $IC_{50}$ values $\leq 40$ nM. In other embodiments, exemplary compounds exhibited $IC_{50}$ values $\leq 30$ nM. In other embodiments, exemplary compounds exhibited $IC_{50}$ values $\leq 25$ nM.

As detailed in the exemplification herein, in assays to determine the ability of compounds to inhibit tumor cell proliferation, certain inventive compounds exhibit $IC_{50}$ values $\leq 200$ μM. In certain other embodiments, inventive compounds exhibit $IC_{50}$ values $\leq 150$ μM. In certain other embodiments, inventive compounds exhibit $IC_{50}$ values $\leq 100$ μM. In certain other embodiments, inventive compounds exhibit $IC_{50}$ values $\leq 50$ μM. In certain other embodiments, inventive compounds exhibit $IC_{50}$ values $\leq 10$ μM. In certain other embodiments, inventive compounds exhibit $IC_{50}$ values $\leq 7.5$ μM. In certain embodiments, inventive compounds exhibit $IC_{50}$ values $\leq 5$ μM. In certain other embodiments, inventive compounds exhibit $IC_{50}$ values $\leq 2.5$ μM. In certain embodiments, inventive compounds exhibit $IC_{50}$ values $\leq 1$ μM. In certain other embodiments, inventive compounds exhibit $IC_{50}$ values $\leq 750$ nM. In certain other embodiments, inventive compounds exhibit $IC_{50}$ values $\leq 500$ nM. In certain other embodiments, inventive compounds exhibit $IC_{50}$ values $\leq 250$ nM. In certain other embodiments, inventive compounds exhibit $IC_{50}$ values $\leq 100$ nM. In other embodiments, exemplary compounds exhibit $IC_{50}$ values $\leq 75$ nM. In other embodiments, exemplary compounds exhibit $IC_{50}$ values $\leq 50$ nM.

In certain embodiments, the present invention provides methods for identifying isomigrastatin analogs useful in the preparation of pharmaceutical compositions for the treatment of various disorders including cancer, metastasis, proliferative disorders and disorders involving increased angiogenesis.

In certain exemplary embodiments, there is provided a method for identifying isomigrastatin analogs having antiangiogenic activity, the method comprising steps of:

a. contacting a compound with a plurality of cells, whereby the compound has the structure:

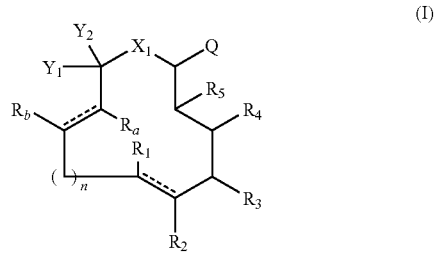

(I)

or pharmaceutically acceptable derivatives thereof;

wherein n is an integer from 1 to 4;

$R_1$ and $R_2$ are each independently hydrogen, halogen, —CN, —S(O)$_{1-2}$R$^{1A}$, —NO$_2$, —COR$^{1A}$, —CO$_2$R$^{1A}$, —NR$^{1A}$C(=O)R$^{1B}$, —NR$^{1A}$C(=O)OR$^{1B}$, —CONR$^{1A}$R$^{1B}$, an aliphatic, heteroaliphatic, alicyclic, heteroalicyclic, aromatic or heteroaromatic moiety, or —WR$^{1A}$; wherein W is independently —O—, —S— or —NR$^{1C}$—, wherein each occurrence of R$^{1A}$, R$^{1B}$ and R$^{1C}$ is independently hydrogen, or an aliphatic, heteroaliphatic, alicyclic, heteroalicyclic, aromatic or heteroaromatic moiety; or $R_1$ and $R_2$, taken together with the carbon atoms to which they are attached, form an alicyclic, heteroalicyclic, aromatic or heteroaromatic moiety;

$R_3$ is hydrogen, halogen, aliphatic, heteroaliphatic, alicyclic, heterocyclic, aryl or heteroaryl moiety, or —WR$^{3A}$; wherein W is independently —O—, —S—, —NR$^{3B}$— or —C(=O)—, wherein R$^{3A}$ is hydrogen, an aliphatic, heteroaliphatic, alicyclic, heterocyclic, aryl or heteroaryl moiety; —C(=O)R$^{3C}$, —Si(R$^{3C}$)$_3$, —C(=S)R$^{3C}$, —C(=NR$^{3C}$)R$^{3C}$, —SO$_2$R$^{3C}$, or —ZR$^{3C}$, wherein Z is —O—, —S—, —NR$^{3D}$, wherein each occurrence of R$^{3B}$, R$^{3C}$ and R$^{3D}$ is independently hydrogen, or an aliphatic, heteroaliphatic, alicyclic, heterocyclic, aryl or heteroaryl moiety;

$R_4$ is halogen, —OR$^{4A}$, OC(=O)R$^{4A}$ or —NR$^{4A}$R$^{4B}$; wherein R$^{4A}$ and R$^{4B}$ are independently hydrogen, an aliphatic, heteroaliphatic, alicyclic, heteroalicyclic, aromatic or heteroaromatic moiety; a prodrug moiety, a nitrogen protecting group or an oxygen protecting group; or $R^{4A}$ and $R^{4B}$, taken together with the nitrogen atom to which they are attached, form a heterocyclic or heteroaryl moiety; or $R_4$, taken together with the carbon atom to which it is attached forms a moiety having the structure:

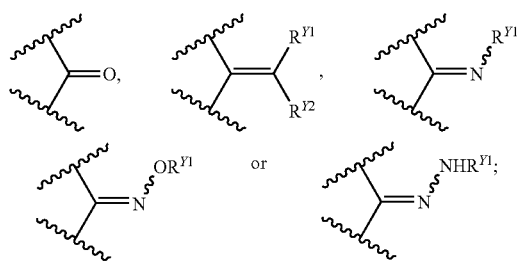

$R_5$ is hydrogen, an aliphatic, heteroaliphatic, alicyclic, heteroalicyclic, aromatic or heteroaromatic moiety;

$R_a$ and each occurrence of $R_b$ are independently hydrogen, halogen, —CN, —S(O)$_{1-2}$R$^{a1}$, —NO$_2$, —COR$^{a1}$, —CO$_2$R$^{a1}$, —NR$^a$C(=O)R$^{a2}$, —NR$^{a1}$C(=O)OR$^{a2}$, CONR$^{a1}$R$^{a2}$, an aliphatic, heteroaliphatic, alicyclic, heteroalicyclic, aromatic or heteroaromatic moiety, or —WR$^{a1}$; wherein W is independently —O—, —S— or —NR$^{a3}$—, wherein each occurrence of R$^{a1}$, R$^{a2}$ and R$^{a3}$ is independently hydrogen, or an aliphatic, heteroaliphatic, alicyclic, heteroalicyclic, aromatic or heteroaromatic moiety; or $R_a$ and the adjacent occurrence of $R_b$, taken together with the carbon atoms to which they are attached, form an alicyclic, heteroalicyclic, aromatic or heteroaromatic moiety;

$X_1$ is O, S, NR$^{X1}$ or CR$^{X1}$R$^{X2}$; wherein R$^{X1}$ and R$^{X2}$ are independently hydrogen, halogen, an aliphatic, heteroaliphatic, alicyclic, heteroalicyclic, aromatic or heteroaromatic moiety, or a nitrogen protecting group;

Q is hydrogen, halogen, —CN, —S(O)$_{1-2}$R$^{Q1}$, —NO$_2$, —COR$^{Q1}$, —CO$_2$R$^{Q1}$, —NR$^{Q1}$C(=O)R$^{Q2}$, —NR$^{Q1}$C(=O)OR$^{Q2}$, —CONR$^{Q1}$R$^{Q2}$, an aliphatic, heteroaliphatic, alicyclic, heteroalicyclic, aromatic or heteroaromatic moiety, or —WR$^{Q1}$; wherein W is independently —O—, —S— or —NR$^{Q3}$—, wherein each occurrence of R$^{Q1}$, R$^{Q2}$ and R$^{Q3}$ is independently hydrogen, or an aliphatic, heteroaliphatic, alicyclic, heteroalicyclic, aromatic or heteroaromatic moiety;

$Y_1$ and $Y_2$ are independently hydrogen, an aliphatic, heteroaliphatic, alicyclic, heteroalicyclic, aromatic or heteroaromatic moiety; or —WR$^{Y1}$; wherein W is independently —O—, —S— or —NR$^{Y2}$—, wherein each occurrence of R$^{Y1}$ and R$^{Y2}$ is independently hydrogen, or an aliphatic, heteroaliphatic, alicyclic, heteroalicyclic, aromatic or heteroaromatic moiety; or $Y_1$ and $Y_2$ together with the carbon atom to which they are attached form a moiety having the structure:

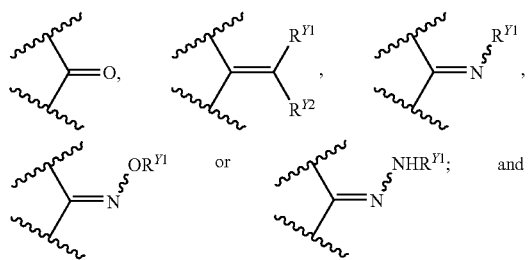

and b. evaluating the effect of the compound on the complexity of the tube network among the cells.

In certain embodiments, the compound being contacted with the plurality of cells is at a concentration ≦200 μM. In certain exemplary embodiments, the compound has the following stereochemistry:

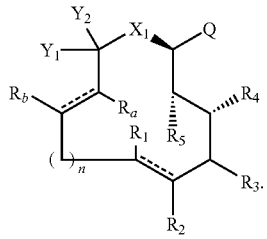

In certain embodiments, in the method described directly above, the step of evaluating comprises comparing the disturbance of the complexity of the tube network with that observed for cells exposed to a reference Migrastatin concentration. In certain exemplary embodiments, the reference Migrastatin concentration is about 100 μM. In certain exemplary embodiments, the reference Migrastatin concentration is about 75 μM. In certain exemplary embodiments, the reference Migrastatin concentration is about 50 μM. In certain exemplary embodiments, the reference Migrastatin concentration is about 30 μM.

In certain embodiments, the method is for identifying isomigrastatin analogs useful in the preparation of pharmaceutical compositions for the treatment of angiogenesis-related disorders.

In certain other embodiments, the invention provides a highthroughput method for identifying isomigrastatin analogs having anti-angiogenic activity, the method comprising steps of:

a. introducing in each of a plurality of reaction vessels:
   a plurality of cells; and
   one or more test compounds with having the structure (I) as defined generally above and in classes and subclasses herein; or pharmaceutically acceptable derivative thereof; and b. evaluating in each reaction vessel the effect of the test compound on the complexity of the tube network in the cells.

In certain embodiments, the test compound being contacted with the plurality of cells is at a concentration ≦200 μM. In certain exemplary embodiments, the test compound has the following stereochemistry:

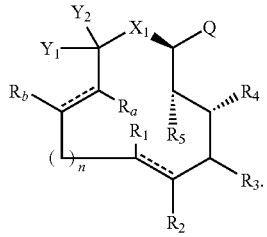

In certain embodiments, in the method described directly above, the step of evaluating comprises comparing the disturbance of the complexity of the tube network in each reaction vessel with that observed for cells exposed to a reference Migrastatin concentration. In certain exemplary embodiments, the reference Migrastatin concentration is about 100

μM. In certain exemplary embodiments, the reference Migrastatin concentration is about 75 μM. In certain exemplary embodiments, the reference Migrastatin concentration is about 50 μM. In certain exemplary embodiments, the reference Migrastatin concentration is about 30 μM.

In certain embodiments, the method is for identifying isomigrastatin analogs useful in the preparation of pharmaceutical compositions for the treatment of angiogenesis-related disorders.

In certain exemplary embodiments, there is provided a method for identifying isomigrastatin analogs having cell migration inhibitory activity, the method comprising steps of:
 a. providing a plurality of cells;
 b. applying a scratch to the cell layer surface;
 c. contacting the cells with a compound having the structure (I) as defined generally above and in classes and subclasses herein; or pharmaceutically acceptable derivative thereof; and
 b. evaluating the wound healing effect of the compound on the cells.

In certain embodiments, the compound being contacted with the plurality of cells is at a concentration $\leq 200$ μM. In certain exemplary embodiments, the compound has the following stereochemistry:

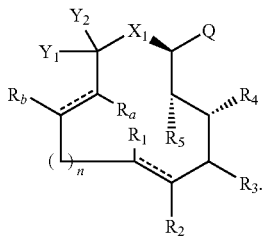

In certain embodiments, in the method described directly above, the step of evaluating comprises comparing the compound wound healing effect with that observed for cells exposed to a reference Migrastatin concentration. In certain exemplary embodiments, the reference Migrastatin concentration is about 100 μM. In certain exemplary embodiments, the reference Migrastatin concentration is about 75 μM. In certain exemplary embodiments, the reference Migrastatin concentration is about 50 μM. In certain exemplary embodiments, the reference Migrastatin concentration is about 30 μM.

In certain embodiments, the method is for identifying isomigrastatin analogs useful in the preparation of pharmaceutical compositions for the treatment of metastasis-related disorders In certain embodiments, the method may be adapted to high-throughput format wherein the cells and test compounds are introduced and assayed in each of a plurality of reaction vessels. For example, in certain embodiments, there is provided a highthroughput method for identifying isomigrastatin analogs having cell migration inhibitory activity, the method comprising steps of:
 a. introducing a plurality of cells in each of a plurality of reaction vessels;
 b. in each reaction vessel, applying a scratch to the cell layer surface;
 c. contacting the cells, in each reaction vessel, with one or more test compounds having the structure (I) as defined generally above and in classes and subclasses herein; or pharmaceutically acceptable derivative thereof, and
 d. evaluating the wound healing effect of the test compound on the cells in each reaction vessel.

In certain embodiments, the test compound being contacted with the plurality of cells is at a concentration $\leq 200$ μM. In certain exemplary embodiments, the test compound has the following stereochemistry:

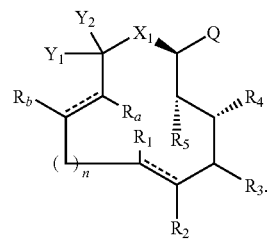

In certain embodiments, in the method described directly above, the step of evaluating comprises comparing the compound wound healing effect in each reaction vessel with that observed for cells exposed to a reference Migrastatin concentration. In certain exemplary embodiments, the reference Migrastatin concentration is about 100 μM. In certain exemplary embodiments, the reference Migrastatin concentration is about 75 μM. In certain exemplary embodiments, the reference Migrastatin concentration is about 50 μM. In certain exemplary embodiments, the reference Migrastatin concentration is about 30 μM.

In certain embodiments, the method is for identifying isomigrastatin analogs useful in the preparation of pharmaceutical compositions for the treatment of angiogenesis-related disorders.

In certain other exemplary embodiments, there is provided a method for identifying isomigrastatin analogs having cell migration inhibitory activity, comprising steps of:
 a. introducing a plurality of cells into an upper compartment;
 b. introducing a test compound having the structure (1) as defined generally above and in classes and subclasses herein; or pharmaceutically acceptable derivative thereof; into the upper compartment and a lower compartment, whereby the lower compartment is separated from the upper compartment by a cell-permeable membrane; and
 c. assessing cell migration from the upper to the lower compartment after a given period of time.

In certain embodiments, the compound being contacted with the plurality of cells is at a concentration $\leq 200$ μM. In certain exemplary embodiments, the compound has the following stereochemistry:

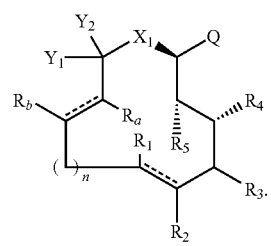

In certain embodiments, in the method described directly above, the step of evaluating comprises comparing cell migration from the upper to the lower compartment with that observed for cells exposed to a reference Migrastatin concentration after about the same period of time. In certain exemplary embodiments, the reference Migrastatin concentration is about 100 μM. In certain exemplary embodiments, the reference Migrastatin concentration is about 75 μM. In certain exemplary embodiments, the reference Migrastatin concentration is about 50 μM. In certain exemplary embodiments, the reference Migrastatin concentration is about 30 μM.

In certain embodiments, the method is for identifying isomigrastatin analogs useful in the preparation of pharmaceutical compositions for the treatment of metastasis-related disorders.

In certain embodiments, the method may be adapted to high-throughput format wherein the cells and test compounds are introduced and assayed in each of a plurality of reaction vessels. For example, in certain embodiments, there is provided a highthroughput method for identifying isomigrastatin analogs having cell migration inhibitory activity, the method comprising steps of:

a. providing a plurality of reaction vessels, each comprising an upper and lower compartment separated by a cell-permeable membrane;

b. introducing a plurality of cells into the upper compartment of each of the plurality of reaction vessels;

c. introducing a test compound having the structure (I) as defined generally above and in classes and subclasses herein; or pharmaceutically acceptable derivative thereof; into the upper and lower compartment of each of the plurality of reaction vessels; and d. in each reaction vessel, assessing cell migration from the upper to the lower compartment after a given period of time.

In certain embodiments of each of the highthroughput methods described above, a different concentration of the same test compound is introduced in each reaction vessel. In certain other embodiments, a different test compound is introduced in each reaction vessel. In certain embodiments, a different concentration of the same test compound is introduced in a subset of the reaction vessels; and a different test compound is introduced in another subset of the reaction vessels.

In certain embodiments, a highthroughput method according to the present invention is practiced with dense arrays of reaction vessels. Preferably, the center-to-center distance between reaction vessels is less than about 8.5 mm. More preferably, the distance is less than 4.5 mm. Even more preferably the distance is less than approximately 2.25 mm. Most preferably, the distance is less than approximately 1 mm. In certain embodiments, the method is performed with a 48-well culture dish.

Conventional high throughput screens are often performed in commercially available 48- or 96-well plates (see, for example, Rice et al. *Anal. Biochem.* 241:254-259. 1996). Such plates may be utilized according to the present invention. However, denser arrays are generally preferred, though it is appreciated that such arrays may desirably have the same external dimensions of a standard 48- or 96-well plate in order to facilitate automation using available equipment. Plates containing 384 (Nalge Nunc International, Naperville, Ill.; Greiner America, Lake Mary, Fla.; Corning Costar, Corning, N.Y.) or 1536 (Greiner America, Lake Mary, Fla.) wells have recently become commercially available and may be used in the practice of the present invention. In certain embodiments, a highthroughput method according to the present invention is compatible with any or all of these array formats.

Pharmaceutical Uses and Methods of Treatment

In yet another aspect, the present invention provides methods of treatment of various disorders, including those associated with metastasis and/or increased angiogenic activity. In certain embodiments, according to the methods of treatment of the present invention, metastasis and/or the growth of tumor cells is inhibited by contacting said tumor cells with an inventive compound or composition, as described herein.

Accordingly, in another aspect of the invention, methods for the treatment of cancer are provided comprising administering a therapeutically effective amount of a compound of formula (I), as described herein, to a subject in need thereof. In certain embodiments, a method for the treatment of cancer is provided comprising administering a therapeutically effective amount of an inventive compound, or a pharmaceutical composition comprising an inventive compound to a subject in need thereof, in such amounts and for such time as is necessary to achieve the desired result.

In certain embodiments, the method involves the administration of a therapeutically effective amount of the compound or a pharmaceutically acceptable derivative thereof to a subject (including, but not limited to a human or animal) in need of it. In certain embodiments, the inventive compounds as useful for the treatment of cancer (including, but not limited to, glioblastoma, retinoblastoma, breast cancer, cervical cancer, colon and rectal cancer, leukemia, lymphoma, lung cancer (including, but not limited to small cell lung cancer), melanoma and/or skin cancer, multiple myeloma, non-Hodgkin's lymphoma, ovarian cancer, pancreatic cancer, prostate cancer and gastric cancer, bladder cancer, uterine cancer, kidney cancer, testicular cancer, stomach cancer, brain cancer, liver cancer, or esophageal cancer). In certain exemplary embodiments, the inventive compounds as useful for the treatment of ovarian and/or cancer. In certain exemplary embodiments, the inventive compounds as useful for the treatment of metastatic ovarian cancer. In certain other embodiments, the compounds are useful for facilitating wound healing. In yet other embodiments, the compounds are useful for treating ascites.

As discussed above, the compounds of the present invention inhibit metastasis of tumor cells and/or inhibiting the growth of tumor cells. In general, the inventive anticancer agents are useful in the treatment of cancers and other proliferative disorders, including, but not limited to breast cancer, cervical cancer, colon and rectal cancer, leukemia, lung cancer, melanoma, multiple myeloma, non-Hodgkin's lymphoma, ovarian cancer, pancreatic cancer, prostate cancer, and gastric cancer, to name a few. In certain embodiments, the inventive anticancer agents are active against leukemia cells and melanoma cells, and thus are useful for the treatment of leukemias (e.g., myeloid, lymphocytic, myelocytic and lymphoblastic leukemias) and malignant melanomas. In still other embodiments, the inventive anticancer agents are active against solid tumors. In certain exemplary embodiments, the inventive compounds as useful for the treatment of metastatic cancer. In certain exemplary embodiments, the inventive compounds as useful for the treatment of ovarian cancer. In certain exemplary embodiments, the inventive compounds as useful for the treatment of metastatic ovarian cancer.

In certain embodiments, the present invention provides a method for treating and/or preventing metastasis and/or proliferation of tumor cells in a subject comprising administering to a subject (including, but not limited to, a human or animal) in need thereof a therapeutically effective amount of a compound of the invention and a pharmaceutically acceptable carrier, adjuvant or vehicle. In certain exemplary embodiments, the method is used to treat and/or prevent metastasis and/or proliferation of prostate, breast, colon, bladder, cervical, skin, testicular, kidney, ovarian, stomach, brain, liver, pancreatic or esophageal cancer or lymphoma, leukemia, or multiple myeloma, to name a few. In certain exemplary embodiments, the inventive method is for treating and/or lessening the severity of ovarian cancer. In certain exemplary embodiments, the inventive method is for treating and/or lessening the severity of metastatic ovarian cancer.

In another aspect, the present invention provides methods for decreasing migration of tumor cells. In a further aspect, the present invention provides methods for decreasing anchorage-independent growth of tumor cells. In yet a further aspect, the present invention provides methods for inhibiting angiogenesis.

In yet another aspect, the present invention provides methods for preventing unwanted angiogenesis in a subject (including, but not limited to, a human or animal).

As used herein, the term "angiogenesis" means the generation of new blood vessels into a tissue or organ. Under normal physiological conditions, humans or animals only undergo angiogenesis in very specific restricted situations. For example, angiogenesis is normally observed in wound healing, fetal and embryonal development and formation of the corpus luteum, endometrium and placenta. The control of angiogenesis is a highly regulated system of angiogenic stimulators and inhibitors. The control of angiogenesis has been found to be altered in certain disease states and, in many cases, the pathological damage associated with the disease is related to the uncontrolled angiogenesis.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel. In the disease state, prevention of angiogenesis could avert the damage caused by the invasion of the new microvascular system.

Persistent, unregulated angiogenesis occurs in a multiplicity of disease states, tumor metastasis and abnormal growth by endothelial cells and supports the pathological damage seen in these conditions. The diverse pathological states created due to unregulated angiogenesis have been grouped together as angiogenic dependent or angiogenic associated diseases. Therapies directed at control of the angiogenic processes could lead to the abrogation or mitigation of these diseases.

One example of a disease involving an angiogenic process is ocular neovascular disease. This disease is characterized by invasion of new blood vessels into the structures of the eye such as the retina or cornea. It is the most common cause of blindness and is involved in approximately twenty eye diseases. In agerelated macular degeneration, the associated visual problems are caused by an ingrowth of chorioidal capillaries through defects in Bruch's membrane with proliferation of fibrovascular tissue beneath the retinal pigment epithelium. Angiogenic damage is also associated with diabetic retinopathy, retinopathy of prematurity, corneal graft rejection, neovascular glaucoma and retrolental fibroplasia. Other diseases associated with corneal neovascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi's sarcoma, Mooren's ulcer, Terrien's marginal degeneration, mariginal keratolysis, rheumatoid arthritis, systemic lupus, polyarteritis, trauma, Wegener's sarcoidosis, scleritis, Stevens-Johnson disease, pemphigoid, radial keratotomy, and corneal graph rejection.

Diseases associated with retinal/choroidal neovascularization include, but are not limited to, diabetic retinopathy, macular degeneration, sickle cell anemia, sarcoid, syphilis, pseudoxanthoma elasticum, Paget's disease, vein occlusion, artery occlusion, carotid obstructive disease, clronic uveitis/vitritis, mycobacterial infections, Lyme's disease, systemic lupus erythematosis, retinopathy of prematurity, Eales' disease, Bencet's disease, infections causing a retinitis or choroiditis, presumed ocular histoplasmosis, Best's disease, myopia, optic pits, Stargardt's disease, pars planitis, chronic retinal detachment, hyperviscosity syndromes, toxoplasmosis, trauma and post-laser complications. Other diseases include, but are not limited to, diseases associated with rubeosis (neovasculariation of the angle) and diseases caused by the abnormal proliferation of fibrovascular or fibrous tissue including all forms of proliferative vitreoretinopathy.

Another disease in which angiogenesis is believed to be involved is rheumatoid arthritis. The blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis.

Factors associated with angiogenesis may also have a role in osteoarthritis. The activation of the chondrocytes by angiogenic-related factors contributes to the destruction of the joint. At a later stage, the angiogenic factors would promote new bone formation. Therapeutic intervention that prevents the bone destruction could halt the progress of the disease and provide relief for persons suffering with arthritis.

Chronic inflammation may also involve pathological angiogenesis. Such disease states as ulcerative colitis and Crohn's disease show histological changes with the ingrowth of new blood vessels into the inflamed tissues. Bartonellosis, a bacterial infection found in South America, can result in a chronic stage that is characterized by proliferation of vascular endothelial cells. Another pathological role associated with angiogenesis is found in atherosclerosis. The plaques formed within the lumen of blood vessels have been shown to have angiogenic stimulatory activity.

One of the most frequent angiogenic diseases of childhood is the hemangioma. In most cases, the tumors are benign and regress without intervention. In more severe cases, the tumors progress to large cavernous and infiltrative forms and create clinical complications. Systemic forms of hemangiomas, the hemangiomatoses, have a high mortality rate. Therapy-resistant hemangiomas exist that cannot be treated with therapeutics currently in use.

Angiogenesis is also responsible for damage found in hereditary diseases such as Osler-Weber-Rendu disease, or hereditary hemorrhagic telangiectasia. This is an inherited disease characterized by multiple small angiomas, tumors of blood or lymph vessels. The angiomas are found in the skin and mucous membranes, often accompanied by epistaxis (nosebleeds) or gastrointestinal bleeding and sometimes with pulmonary or hepatic arteriovenous fistula.

Angiogenesis is prominent in solid tumor formation and metastasis. Angiogenic factors have been found associated with several solid tumors such as rhabdomyosarcomas, retinoblastoma, Ewing sarcoma, neuroblastoma, and osteosarcoma. A tumor cannot expand without a blood supply to provide nutrients and remove cellular wastes. Tumors in which angiogenesis is important include solid tumors, and benign tumors such as acoustic neuroma, neurofibroma, trachoma and pyogenic granulomas. Prevention of angiogenesis could halt the growth of these tumors and the resultant damage to the animal due to the presence of the tumor.

It should be noted that angiogenesis has been associated with blood-born tumors such as leukemias, any of various acute or chronic neoplastic diseases of the bone marrow in which unrestrained proliferation of white blood cells occurs, usually accompanied by anemia, impaired blood clotting, and enlargement of the lymph nodes, liver, and spleen. It is believed that angiogenesis plays a role in the abnormalities in the bone marrow that give rise to leukemia-like tumors.

Angiogenesis is important in two stages of tumor metastasis. The first stage where angiogenesis stimulation is important is in the vascularization of the tumor which allows tumor cells to enter the blood stream and to circulate throughout the body. After the tumor cells have left the primary site, and have settled into the secondary, metastasis site, angiogenesis must occur before the new tumor can grow and expand. Therefore, prevention of angiogenesis could lead to the prevention of metastasis of tumors and possibly contain the neoplastic growth at the primary site.

Knowledge of the role of angiogenesis in the maintenance and metastasis of tumors has led to a prognostic indicator for breast cancer. The amount of neovascularization found in the primary tumor was determined by counting the microvessel density in the area of the most intense neovascularization in invasive breast carcinoma. A high level of microvessel density was found to correlate with tumor recurrence. Control of angiogenesis by therapeutic means could possibly lead to cessation of the recurrence of the tumors.

Angiogenesis is also involved in normal physiological processes such as reproduction and wound healing. Angiogenesis is an important step in ovulation and also in implantation of the blastula after fertilization. Prevention of angiogenesis could be used to induce amenorrhea, to block ovulation or to prevent implantation by the blastula.

In wound healing, excessive repair or fibroplasia can be a detrimental side effect of surgical procedures and may be caused or exacerbated by angiogenesis. Adhesions are a frequent complication of surgery and lead to problems such as small bowel obstruction.

Accordingly, in one aspect, the present invention provides method to inhibit unwanted angiogenesis in a subject (including, but not limited to, a human or animal).

In another aspect, the present invention provides a method for the treatment for diseases mediated by angiogenesis.

In another aspect, the present invention provides a method for the treatment for macular degeneration.

In another aspect, the present invention provides a method for the treatment for all forms of proliferative vitreoretinopathy including those forms not associated with diabetes.

In another aspect, the present invention provides a method for the treatment for solid tumors.

In another aspect, the present invention provides a method for the treatment of blood-borne tumors, such as leukemia.

In another aspect, the present invention provides a method for the treatment of hemangioma.

In another aspect, the present invention provides a method for the treatment of retrolental fibroplasia.

In another aspect, the present invention provides a method for the treatment of psoriasis.

In another aspect, the present invention provides a method for the treatment of Kaposi's sarcoma.

In another aspect, the present invention provides a method for the treatment of Crohn's disease.

In another aspect, the present invention provides a method for the treatment of diabetic retinopathy.

Thus, in certain embodiments, the invention provides a method for preventing unwanted angiogenesis in a subject (including, but not limited to, a human or animal) comprising administering to a subject in need thereof a therapeutically effective amount of the compound of the invention in an amount effective to inhibit angiogenesis.

In certain other embodiments, the invention provides a method for treating an angiogenesis-dependent disease in a subject (including, but not limited to, a human or animal) comprising administering to a subject in need thereof a therapeutically effective amount of the compound of the invention in an amount effective to inhibit angiogenesis.

Diseases associated with corneal neovascularization that can be treated according to the present invention include but are not limited to, diabetic retinopathy, retinopathy of prematurity, corneal graft rejection, neovascular glaucoma and retrolental fibroplasia, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi's sarcoma, Mooren's ulcer, Terrien's marginal degeneration, mariginal keratolysis, trauma, rheumatoid arthritis, systemic lupus, polyarteritis, Wegener's sarcoidosis, scleritis, Stevens-Johnson disease, pemphigoid, radial keratotomy, and corneal graph rejection.

Diseases associated with retinal/choroidal neovascularization that can be treated according to the present invention include, but are not limited to, diabetic retinopathy, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme's disease, systemic lupus erythematosis, retinopathy of prematurity, Eales' disease, Behcet's disease, infections causing a retinitis or choroiditis, presumed ocular histoplasmosis, Best's disease, myopia, optic pits, Stargardt's disease, pars planitis, chronic retinal detachment, hyperviscosity syndromes, toxoplasmosis, trauma and post-laser complications. Other diseases include, but are not limited to, diseases associated with rubeosis (neovasculariation of the angle) and diseases caused by the abnormal proliferation of fibrovascular or fibrous tissue including all forms of proliferative vitreoretinopathy, whether or not associated with diabetes.

Diseases associated with chronic inflammation can be treated by the compositions and methods of the present invention. Diseases with symptoms of chronic inflammation include inflammatory bowel diseases such as Crohn's disease and ulcerative colitis, psoriasis, sarcoidosis and rheumatoid arthritis. Angiogenesis is a key element that these chronic inflammatory diseases have in common. The chronic inflammation depends on continuous formation of capillary sprouts to maintain an influx of inflammatory cells. The influx and presence of the inflammatory cells produce granulomas and thus, maintains the chronic inflammatory state. Inhibition of angiogenesis by the compositions and methods of the present invention would prevent the formation of the granulomas and alleviate the disease.

The compositions and methods of the present invention can be used to treat patients with inflammatory bowel diseases such as Crohn's disease and ulcerative colitis. Both Crohn's disease and ulcerative colitis are characterized by chronic inflammation and angiogenesis at various sites in the gastrointestinal tract. Crohn's disease is characterized by chronic granulomatous inflammation throughout the gastrointestinal tract consisting of new capillary sprouts surrounded by a cylinder of inflammatory cells. Prevention of angiogenesis by the compositions and methods of the present invention inhibits the formation of the sprouts and prevents the formation of granulomas.

Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhea associated with abdominal pain, fever, anorexia, weight loss and abdominal swelling. Ulcerative colitis is also a chronic, nonspecific, inflammatory and ulcerative disease arising in the colonic mucosa and is characterized by the presence of bloody diarrhea.

The inflammatory bowel diseases also show extraintestinal manifestations such as skin lesions. Such lesions are characterized by inflammation and angiogenesis and can occur at many sites other than the gastrointestinal tract. The compositions and methods of the present invention are also capable of treating these lesions by preventing the angiogenesis, thus reducing the influx of inflammatory cells and the lesion formation.

Sarcoidosis is another chronic inflammatory disease that is characterized as a multisystem granulomatous disorder. The granulomas of this disease may form anywhere in the body and thus the symptoms depend on the site of the granulomas and whether the disease active. The granulomas are created by the angiogenic capillary sprouts providing a constant supply of inflammatory cells.

The compositions and methods of the present invention can also treat the chronic inflammatory conditions associated with psoriasis. Psoriasis, a skin disease, is another chronic and recurrent disease that is characterized by papules and plaques of various sizes. Prevention of the formation of the new blood vessels necessary to maintain the characteristic lesions leads to relief from the symptoms.

Another disease which can be treated according to the present invention is rheumatoid arthritis. Rheumatoid arthritis is a chronic inflammatory disease characterized by nonspecific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Another disease that can be treated according to the present invention are hemangiomas, Osler-Weber-Rendu disease, or hereditary hemorrhagic telangiectasia, solid or blood borne tumors and acquired immune deficiency syndrome.

By virtue of their cell migration inhibitory activity, isomigrastatin analogs of the invention are useful for blocking ascites (excess fluid in the abdominal cavity), a condition often associated with various malignacies (e.g., peritoneal metastasis). Accordingly, there is provided a method for treating and/or lessening the severity of acsites in a subject in need thereof comprising administering an effective amount of a compound of formula I. In certain embodiments, the subject is a mammal. In certain exemplary embodiments, the subject is human.

It will be appreciated that the compounds and compositions, according to the method of the present invention, may be administered using any amount and any route of administration effective for the treatment of cancer and/or disorders associated with metastasis and/or angiogenesis. Thus, the expression "effective amount" as used herein, refers to a sufficient amount of agent to inhibit the growth of tumor cells, or refers to a sufficient amount to reduce the effects of cancer. The exact amount required will vary from subject to subject, depending on the species, age, and general condition of the subject, the severity of the diseases, the particular anticancer agent, its mode of administration, and the like.

The compounds of the invention are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts (see, for example, Goodman and Gilman's, "The Pharmacological Basis of Therapeutics", Tenth Edition, A. Gilman, J. Hardman and L. Limbird, eds., McGraw-Hill Press, 155-173, 2001, which is incorporated herein by reference in its entirety).

Furthermore, after formulation with an appropriate pharmaceutically acceptable carrier, adjuvant or vehicle in a desired dosage, the pharmaceutical compositions of this invention can be administered to humans and other animals orally, rectally, parenterally, intracisternally, intravaginally, intraperitoneally, topically (as by powders, ointments, creams or drops), bucally, as an oral or nasal spray, or the like, depending on the severity of the infection being treated. In certain embodiments, compounds of the invention may be administered at dosage levels of about 0.001 mg/kg to about 50 mg/kg, of subject body weight per day, one or more times a day, to obtain the desired therapeutic effect. It will also be appreciated that dosages smaller than 0.001 mg/kg or greater than 50 mg/kg (for example 50-100 mg/kg) can be administered to a subject. In certain embodiments, compounds are administered orally or parenterally.

Dosage ranges suitable for administration to a subject (e.g., humans) suffering from a condition associated with cancer metastasis (e.g., ovarian tumor metastasis) were defined based on the in vivo data detailed in FIGS. 5-8. Methods for extrapolating effective dosages in mice and other animals, to humans are known in the art (See, for example, U.S. Pat. No. 4,938,949). For example, in certain embodiments, compounds of the invention (for example those useful for the treatment of ovarian cancer) may be administered at dosage levels of about 0.01 mg/kg to about 300 mg/kg, from about 0.1 mg/kg to about 250 mg/kg, from about 1 mg/kg to about 200 mg/kg, from about 1 mg/kg to about 150 mg/kg, from about 1 mg/kg to about 100 mg/kg, from about 1 mg/kg to about 90 mg/kg, from about 1 mg/kg to about 80 mg/kg, from about 1 mg/kg to about 70 mg/kg, from about 1 mg/kg to about 60 mg/kg, from about 1 mg/kg to about 50 mg/kg, from about 1 mg/kg to about 40 mg/kg, from about 1 mg/kg to about 30 mg/kg, from about 1 mg/kg to about 20 mg/kg, from about 5 mg/kg to about 100 mg/kg, from about 5 mg/kg to about 90 mg/kg, from about 5 mg/kg to about 80 mg/kg, from about 5 mg/kg to about 70 mg/kg, from about 5 mg/kg to about 60 mg/kg, from about 5 mg/kg to about 50 mg/kg, from about 5 mg/kg to about 40 mg/kg, from about 5 mg/kg to about 30 mg/kg, from about 5 mg/kg to about 20 mg/kg, from about 10 mg/kg to about 100 mg/kg, from about 10 mg/kg to about 90 mg/kg, from about 10 mg/kg to about 80 mg/kg, from about 10 mg/kg to about 70 mg/kg, from about 10 mg/kg to about 60 mg/kg, from about 10 mg/kg to about 50 mg/kg, from about 10 mg/kg to about 40 mg/kg, from about 10 mg/kg to about 30 mg/kg, from about 10 mg/kg to about 20 mg/kg, from about 20 mg/kg to about 100 mg/kg, from about 20 mg/kg to about 90 mg/kg, from about 20 mg/kg to about 80 mg/kg, from about 20 mg/kg to about 70 mg/kg, from about 20 mg/kg to about 60 mg/kg, from about 20 mg/kg to about 50 mg/kg, from about 20 mg/kg to about 40 mg/kg, from about 20 mg/kg to about 30 mg/kg, of subject body weight per day, one or more times a day, to obtain the desired therapeutic effect. In certain embodiments, compounds may be administered at a dosage of about 1 mg/kg or greater, 5 mg/kg or greater, 10 mg/kg or greater, 15 mg/kg or greater, 20 mg/kg or greater, 25 mg/kg or greater, 30 mg/kg or greater, 35 mg/kg or greater, 40 mg/kg or greater, 45 mg/kg or greater, 50 mg/kg or greater, 60 mg/kg or greater, 70 mg/kg or greater, of body weight. It will also be appreciated that dosages smaller than 0.01 mg/kg or greater than 70 mg/kg (for example 70-200 mg/kg) can be administered to a subject.

In certain embodiments, compounds may be used in chemotherapy (i.e., as cytotoxic drug) and may be administered at higher dosage. For example, compounds to be used in chemotherapy may be administered from about 100 mg/kg to about 300 mg/kg, from about 120 mg/kg to about 280 mg/kg, from about 140 mg/kg to about 260 mg/kg, from about 150 mg/kg to about 250 mg/kg, from about 160 mg/kg to about 240 mg/kg, of subject body weight per day, one or more times a day, to obtain the desired therapeutic effect.

In certain other embodiments, compounds may be used in supportive therapy (e.g., as an adjuvant to surgery or irradiation in a range of common types of tumour) and may be administered at lower dosage. For example, compounds to be used in supportive therapy may be administered from about 1 mg/kg to about 30 mg/kg, from about 1 mg/kg to about 25 mg/kg, from about 5 mg/kg to about 20 mg/kg, of subject body weight per day, one or more times a day, to obtain the desired therapeutic effect.

In certain other embodiments, compounds may be used for lessenng the severity of and/or treating metastatic cancer (e.g., ovarian cancer) and may be administered at an intermediate dosage. For example, compounds to be used in supportive therapy may be administered from about 1 mg/kg to about 80 mg/kg, from about 5 mg/kg to about 70 mg/kg, from about 10 mg/kg to about 70 mg/kg, from about 10 mg/kg to about 60 mg/kg, from about 20 mg/kg to about 70 mg/kg, from about 20 mg/kg to about 60 mg/kg, of subject body weight per day, one or more times a day, to obtain the desired therapeutic effect.

Treatment Kit

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

EQUIVALENTS

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art. Throughput this document, various publications are referred to, each of which is hereby incorporated by reference in its entirety in an effort to more fully describe the state of the art to which the invention pertains.

The following examples contain important additional information, exemplification and guidance that can be adapted to the practice of this invention in its various embodiments and the equivalents thereof.

EXEMPLIFICATION

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

1) General Description of Synthetic Methods:

The practitioner has a a well-established literature of macrolide chemistry to draw upon, in combination with the information contained herein, for guidance on synthetic strategies, protecting groups, and other materials and methods useful for the synthesis of the compounds of this invention.

The various references cited herein provide helpful background information on preparing compounds similar to the inventive compounds described herein or relevant intermediates, as well as information on formulation, uses, and administration of such compounds which may be of interest.

Moreover, the practitioner is directed to the specific guidance and examples provided in this document relating to various exemplary compounds and intermediates thereof.

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

According to the present invention, any available techniques can be used to make or prepare the inventive compounds or compositions including them. For example, a variety of solution phase synthetic methods such as those discussed in detail below may be used. Alternatively or additionally, the inventive compounds may be prepared using any of a variety combinatorial techniques, parallel synthesis and/or solid phase synthetic methods known in the art.

It will be appreciated as described below, that a variety of inventive compounds can be synthesized according to the methods described herein. The starting materials and reagents used in preparing these compounds are either available from commercial suppliers such as Aldrich Chemical Company (Milwaukee, Wis.), Bachem (Torrance, Calif.), Sigma (St. Louis, Mo.), or are prepared by methods well known to a person of ordinary skill in the art following procedures described in such references as Fieser and Fieser 1991, "Reagents for Organic Synthesis", vols 1-17, John Wiley and Sons, New York, N.Y., 1991; Rodd 1989 "Chemistry of Carbon Compounds", vols. 1-5 and supps, Elsevier Science Publishers, 1989; "Organic Reactions", vols 1-40, John Wiley and Sons, New York, N.Y., 1991; March 2001, "Advanced Organic Chemistry", 5th ed. John Wiley and Sons, New York, N.Y.; and Larock 1990, "Comprehensive Organic Transformations: A Guide to Functional Group Preparations", 2$^{nd}$ ed. VCH Publishers. These schemes are merely illustrative of some methods by which the compounds of this invention can be synthesized, and various modifications to these schemes can be made and will be suggested to a person of ordinary skill in the art having regard to this disclosure.

The starting materials, intermediates, and compounds of this invention may be isolated and purified using conventional techniques, including filtration, distillation, crystallization, chromatography, and the like. They may be characterized using conventional methods, including physical constants and spectral data.

As discussed herein, the idea of targeting cell migration as an alternative to inhibition of tumor cell proliferation by cytotoxic agents as an anti-cancer therapy has generated considerable interest.[1] A number of pathological conditions, such as tumor angiogenesis, tumor cell invasion and metastasis are involved with cell migration. The possibility of exploiting natural products as leads for the development of anti-angiogenic and anti-metastatic agents has lead to isolation and synthesis of several natural products such as epoxyquinol A and B, trachyspic acid, azaspirene, evodiamine, motuporamines, borrelidine and terpestain. In particular, a series of independent reports by Imoto and Kosan Bioscience on the discovery of natural products migrastatin and isomigrastatin sparked our interest in this area,[2,3] and led to the first chemical synthesis of migrastatin.[4-7]

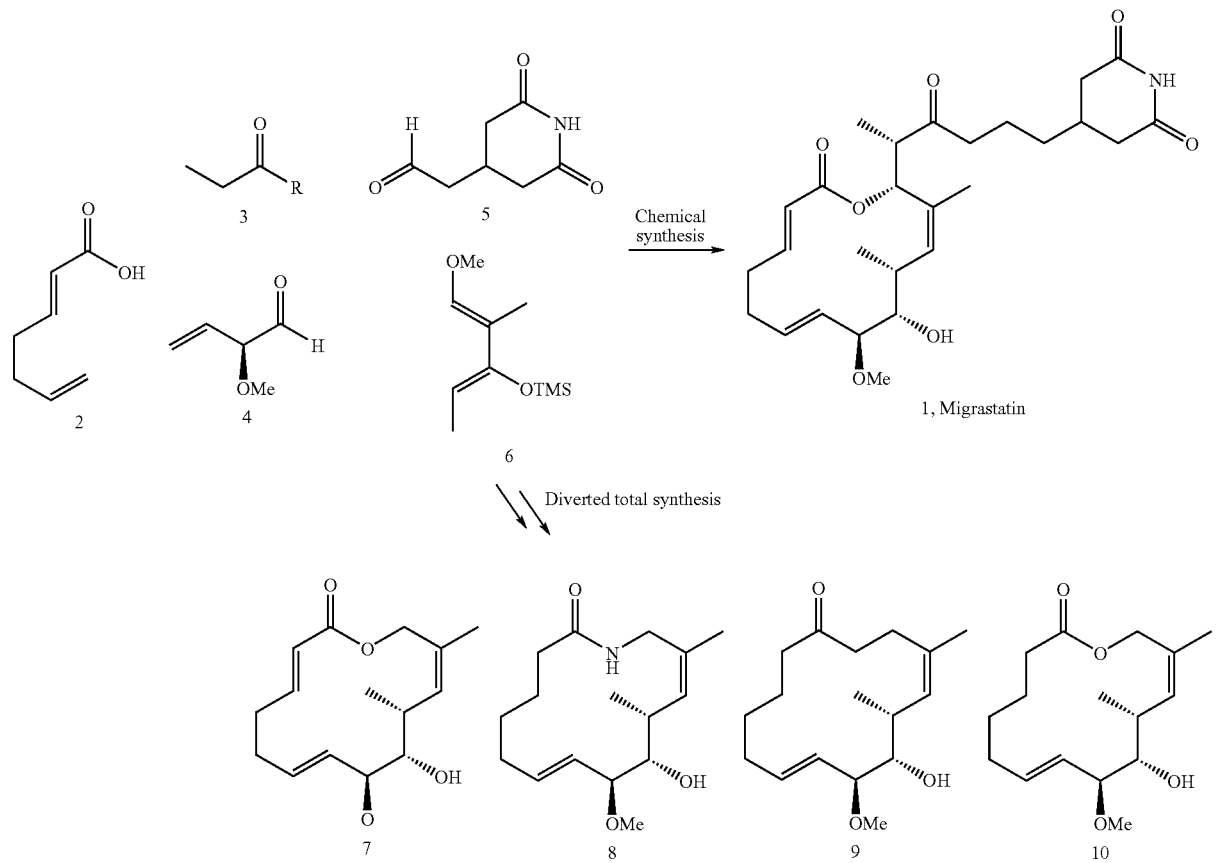

Scheme 1. Migrastatin Based Potent Cell Migration Inhibitors

Although migrastatin showed modest activity, taking it as lead several analogs were prepared (Scheme 1). These analogs are highly potent inhibitors against cancer cells migration in vitro. Currently, the efficacy of these compounds as an anti-metastatic agent in mouse and human models is being evaluated.

In an attempt to identify new molecular entities to strengthen our search for an anti-cancer agents we proceeded to pursue the total synthesis of isomigrastatin and analogs thereof—a natural product with migrastatin-like activity. An exemplary synthetic approach is described in section 2 herein.

General Reaction Procedures:

Unless mentioned specifically, reaction mixtures were stirred using a magnetically driven stirrer bar. Reactions involving air or moisture-sensitive reagents or intermediates were performed under argon or nitrogen atmosphere in glassware which had been heat gun or flame-dried under high vacuum. An inert atmosphere refers to either dry argon or dry nitrogen. Reactions were monitored either by thin layer chromatography, by proton nuclear magnetic resonance (NMR) or by high-pressure liquid chromatography (HPLC), of a suitably worked up sample of the reaction mixture.

Indicated reaction temperatures refer to those of the reaction bath, while room temperature (rt) is noted as 22° C. Preparative reactions were stirred magnetically. Tetrahydrofuran (THF), diethyl ether ($Et_2O$), methylene chloride ($CH_2Cl_2$), and toluene were obtained from a dry solvent system (activated alumina columns, positive pressure of argon). All other solvents were used as received in Sure/Seal bottles (Aldrich). Triethylamine ($Et_3N$), diisopropylethylamine (i-$Pr_2NEt$), pyridine, 2,6-lutidine, and chlorotrimethylsilane (TMSCl) were distilled from $CaH_2$ immediately prior to use. All other reagents were purchased from Aldrich at the highest commercial quality and used without further purification, with the exception of the Stryker reagent which was purchased from Fluka, the RCM catalysts 16 and 17 which were purchased from Strem, and biotin-$dPEG_4$-hydrazide which was purchased from Quanta Biodesign.

General Work Up Procedures:

Unless mentioned specifically, reaction mixtures were cooled to room temperature or below then quenched, when necessary, with either water or a saturated aqueous solution of ammonium chloride. Desired products were extracted by partitioning between water and a suitable water-immiscible solvent (e.g. ethyl acetate, dichloromethane, diethyl ether). The desired product containing extracts were washed appropriately with water followed by a saturated solution of brine. On occasions where the product containing extract was deemed to contain residual oxidants, the extract was washed with a 10% solution of sodium sulphite in saturated aqueous sodium bicarbonate solution, prior to the aforementioned washing procedure. On occasions where the product containing extract was deemed to contain residual acids, the extract was washed with saturated aqueous sodium bicarbonate solution, prior to the aforementioned washing procedure (except in those cases where the desired product itself had acidic character). On occasions where the product containing extract was deemed to contain residual bases, the extract was washed with 10% aqueous citric acid solution, prior to the aforementioned washing procedure (except in those cases where the desired product itself had basic character). Post washing, the desired product containing extracts were dried over anhydrous magnesium sulphate, and then filtered. The crude products were then isolated by removal of solvent(s) by rotary evaporation under reduced pressure, at an appropriate temperature (generally less than 45° C.).

General Purification Procedures:

Unless mentioned specifically, chromatographic purification refers to flash column chromatography on silica, using a single solvent or mixed solvent as eluent. Suitably purified desired product containing elutes were combined and concentrated under reduced pressure at an appropriate temperature (generally less than 45° C.) to constant mass. Final compounds were dissolved in 50% aqueous acetonitrile, filtered and transferred to vials, then freeze-dried under high vacuum before submission for biological testing.

Analytical Equipment:

Analytical Equipment: Optical rotations were measured on a JASCO DIP-370 digital polarimeter at rt. Concentration (c) in g/100 ml and solvent are given in parentheses. Infrared spectra were obtained on a Perkin-Elmer 1600 FT-IR spectrophotometer neat or as a film in $CHCl_3$ (NaCl plates). Absorption bands are noted in $cm^{-1}$. $^1H$- and $^{13}C$-NMR spectra were recorded on a Bruker AMX-400 or a Bruker DRX-500 spectrometer in $CDCl_3$. Chemical shifts (δ-values) are reported in ppm with residual undeuterated CHCl3 as the internal standard (referenced to 7.26 ppm for $^1H$-NMR and 77.0 ppm for $^{13}C$-NMR). Coupling constants (J) (H,H) are given in Hz, spectral splitting patterns are designated as singulet (s), doublet (d), triplet (t), quadruplet (q), multiplet or more overlapping signals (m), apparent (app), broad signal (br). Low resolution mass spectra (ionspray, a variation of electrospray) were acquired on a Perkin-Elmer Sciex API 100 spectrometer. Samples were introduced by direct infusion. High resolution mass spectra (fast atom bombardment, FAB) were acquired on a Micromass 70-SE-4F spectrometer. Flash chromatography (FC) was performed with E. Merck silica gel (60, particle size 0.040-0.063 mm). Preparative thin layer chromatography (TLC) was performed with Whatman Partisil Plates (10×10 cm, 60 Å, 200 µm).

Techniques, Solvents, and Reagents: Reactions involving air or moisture-sensitive reagents or intermediates were performed under argon or nitrogen atmosphere in glassware which had been heat gun or flame-dried under high vacuum. Indicated reaction temperatures refer to those of the reaction bath, while room temperature (rt) is noted as 22° C. Preparative reactions were stirred magnetically. Tetrahydrofuran (THF), diethyl ether ($Et_2O$), methylene chloride ($CH_2Cl_2$), and toluene were obtained from a dry solvent system (activated alumina columns, positive pressure of argon). All other solvents were used as received in Sure/Seal bottles (Aldrich). Triethylamine ($Et_3N$), diisopropylethylamine (i-$Pr_2NEt$), pyridine, 2,6-lutidine, and chlorotrimethylsilane (TMSCl) were distilled from $CaH_2$ immediately prior to use. All other reagents were purchased from Aldrich at the highest commercial quality and used without further purification, with the exception of the Stryker reagent which was purchased from Fluka, the RCM catalysts 16 and 17 which were purchased from Strem, and biotin-dPEG4-hydrazide which was purchased from Quanta Biodesign.

Aldol Product 16:

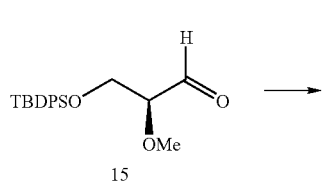

15

-continued

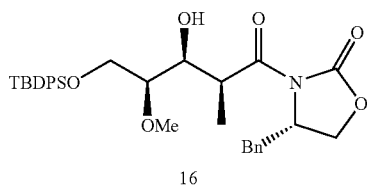

16

To a solution of 4-Benzyl-3-propionyl-oxazolidin-2-one (100 mg, 0.429 mmol) in 3 mL CH$_2$Cl$_2$ at −78° C. was added n-Bu$_2$BOTf (0.472 mL, 1.0 M in CH$_2$Cl$_2$) followed by Et$_3$N (77 □L, 0.557 mmol) under argon. After stirring for 1 hr at −78° C. the reaction mixture was warmed to 0° C. and stirred for 30 minutes. The solution was then cooled back to −78° C. and the aldehyde 15 (148 mg, 0.435 mmol) in 2 mL CH$_2$Cl$_2$ was added. After stirring for 1 hr at −78° C., reaction mixture was warmed to −0° C. and stirred for 3 hr. Phosphate buffer (pH 7) was added. To the resulting mixture was added 2 mL of H$_2$O$_2$ solution in MeOH(H$_2$O$_2$: MeOH 1:2) and stirred overnight at rt. The reaction mixture was evaporated, extracted with CH$_2$Cl$_2$. The organic layer was washed with saturated NaHCO3, dried with MgSO4, concentrated. Purification by FC afforded 40 mg of aldol adduct 16. $^1$H-NMR (500 MHz, CDCl$_3$) δ 7.65-7.60 (m, 4H), 7.38-7.12 (m, 11H), 4.58 (m, 1H), 4.09 (m, 2H), 3.92 (m, 2H), 3.77-3.70 (m, 2H), 3.26-3.16 (m, 4H), 2.69 (m, 2H), 1.26 (d, J=6.4 Hz, 3H), 0.98 (s, 9H); MS (ESI) 598 [M+Na$^+$];

Compound 18:

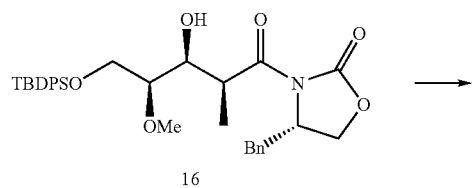

To a solution of 16 (0.086 mmol) in 2 mL of CH$_2$Cl$_2$ was added diisopropyl ethyl amine (0.86 mmol, 0.149 mL) followed by MOMCl (0.86 mmol, 65 μL) at 0° C. under argon. Ice bath was removed and the resulting solution was stirred for overnight. The reaction mixture was quenched with 0.2M aqueous NH$_4$OH solution, extracted with CH$_2$Cl$_2$, dried with MgSO$_4$ and concentrated. Purification by FC (hexanes: EtOAc 4:1) afforded 17 in quantitative yield. To the solution of MOM protected ether (0.086 mmol, 53 mg) in 3 mL THF was added LiBH$_4$ (0.344 mmol, 0.172 mL) followed by MeOH (0.344 mmol, 13 μL) at rt under argon. After stirring for 2 hr reaction mixture was quenched with 1 mL of 0.5N NaOH, extracted with ether, dried with MgSO$_4$ and concentrated. Purification by FC (hexanes:EtOAc 7:3) afforded 30 mg of alcohol 18 in 78% yield. $^1$H-NMR (500 MHz, CDCl$_3$) δ 7.71-7.68 (m, 4H), 7.46-7.38 (m, 6H), 4.80 (d, J=7.0 Hz, 1H), 4.68 (d, J=7.0 Hz, 1H), 3.82-3.71 (m, 3H), 3.50 (m, 2H), 3.41-3.33 (m, 7H), 1.95 (m, 1H), 1.07 (s, 9H), 0.83 (d, J=6.5 Hz, 3H); $^{13}$C-NMR (125 MHz, CDCl$_3$) δ 136.0, 133.7, 130.2, 128.1, 98.7, 83.4, 79.3, 65.2, 63.0, 59.2, 56.4, 37.2, 27.2, 19.6, 12.2; MS (ESI) 469 [M+Na$^+$].

Compound 19:

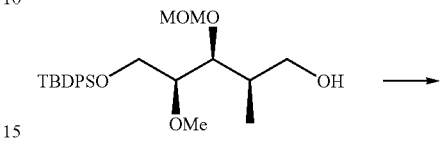

18

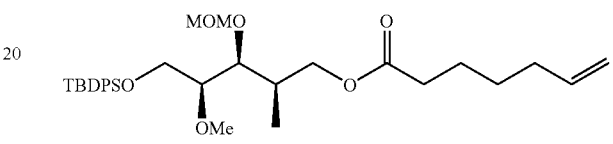

19

To a solution of alcohol 18 (30 mg, 0.067 mmol) in 2 mL CH$_2$Cl$_2$ was added DMAP (24 mg, 0.201 mmol) and hexenoic acid (22 mL, 0.167 mmol. To this solution at 0° C. was added EDCI (38 mg, 0.201 mmol) under argon. After stirring for 0.5 hr at 0° C. and 3 hr at rt the reaction mixture was diluted with water and extracted with CH$_2$Cl$_2$. The organic layer was dried with MgSO$_4$ and concentrated. Purification by FC provided 36 mg of 19 in 64% yield. $^1$H-NMR (400 MHz, CDCl$_3$) δ 7.71-7.67 (m, 4H), 7.47-7.37 (m, 6H), 5.78 (m, 1H), 5.04-4.92 (m, 2H), 4.75 (d, J=7.2 Hz, 1H), 4.67 (d, J=7.2 Hz, 1H), 4.14 (dd, J=11.2 Hz, J=6.8 Hz, 1H), 3.98 (dd, J=11.2 Hz, J=6.8 Hz, 1H), 3.79-3.72 (m, 3H), 3.36-3.26 (m, 7H), 2.36 (m, 2H), 2.16 (m, 1H), 2.06 (m, 2H), 1.64 (m, 2H), 1.42 (m, 2H), 1.07 (s, 9H), 0.94 (d, J=6.0 Hz, 3H); MS (ESI) 579 [M+Na$^+$].

Compound 20:

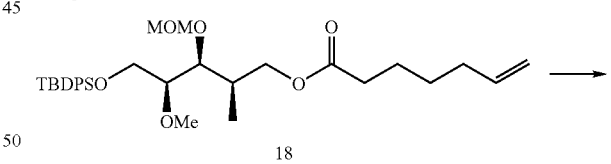

18

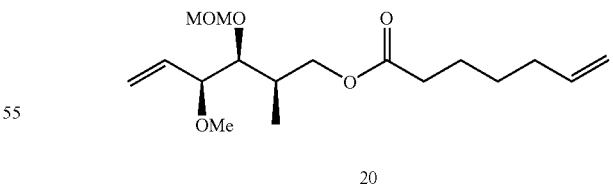

20

To a solution of 19 (30 mg, 0.053 mmol) in 2 mL THF was added TBAF (0.53 mL, 0.53 mmol) at 0° C. under argon. The ice bath was removed and the reaction mixture was stirred at rt for 5 hr. The resulting solution was diluted with water, extracted with ethyl acetate. The ethyl acetate was washed with brine, dried with MgSO$_4$, filtered and concentrated. Purification by FC (hexanes:EtOAc 7:3) afforded 17 mg of corresponding alcohol in quantitative yield. $^1$H-NMR (400

MHz, CDCl$_3$) δ 5.79 (m, 1H), 4.97 (m, 2H), 4.76 (d, J=6.4 Hz, 1H), 4.68 (d, J=6.4 Hz, 1H), 4.09 (dd, J=10.8 Hz, J=6.8 Hz), 4.00 (dd, J=10.8 Hz, J=6.8 Hz), 3.67 (m, 1H), 3.71 (t, J=5.6 Hz, 1H), 3.63 (m, 1H), 3.47 (s, 3H), 3.42 (s, 3H), 3.38 (m, 1H), 2.32 (t, J=7.2 Hz, 2H), 2.07 (m, 3H), 1.69 (m, 2H), 1.97 (m, 2H), 0.98 (d, J=6.4 Hz, 3H); $^{13}$C-NMR (100 MHz, CDCl$_3$) δ 173.6, 138.3, 114.6, 98.3, 82.3, 78.1, 66.5, 60.6, 58.6, 56.3, 34.2, 34.1, 33.3, 28.3, 24.3, 12.1. To a solution of this alcohol (17 mg, 0.053 mmol) in 2 mL CH$_2$Cl$_2$ was added DMP (24 mg, 0.058 mmol) at rt under argon. After 2 hr, additional amount of DMP (12 mg) was added. After stirring for additional 1 hr isopropyl alcohol (1 mL) and followed by 2 mL of 1M Na$_2$S$_2$O$_3$ solution. The resulting solution was extracted with CH$_2$Cl$_2$, washed with brine, dried with MgSO$_4$ and concentrated to yield the corresponding aldehyde. To the solution of this crude aldehyde was added pyridine (4 drops) followed by Tebbes's reagent (0.084 mmol, 0.169 mL) at −78° C. under argon. After stirring for 0.5 hr, the reaction mixture was warmed to −10° C. and stirred for 40 minutes. The resulting solution was quenched with 2 mL 1N aqueous NaOH solution, extracted with ether, dried with MgSO$_4$, filtered and concentrated. Purification by FC (hexanes:EtOAc 7:3) afforded 8 mg of 20 in 48% yield. [α]D−28.2° (c 1.00, CHCl$_3$); IR(CH$_2$Cl$_2$) 2932, 1735, 1157, 1033, 918; $^1$H-NMR (500 MHz, CDCl$_3$) δ 5.78 (m, 1H), 5.63 (m, 1H), 5.29 (m, 2H), 4.96 (m, 2H), 4.80 (d, J=6.5 Hz, 1H), 4.67 (d, J=6.5 Hz, 1H), 4.04 (dd, J=11.0 Hz, J=8 Hz, 1H), 3.98 (dd, J=11.0 Hz, J=8 Hz, 1H), 3.62 (t, J=7.5 Hz, 1H), 3.57 (dd, J=7.0 Hz, J=3 Hz. 1H), 3.38 (s, 3H), 3.27 (s, 3H), 2.30 (t, J=7.5 Hz, 3H), 2.05 (m, 3H), 1.63 (m, 2H), 1.90 (m, 2H), 0.91 (d, J=6.5 Hz, 2H); $^{13}$C-NMR (125 MHz, CDCl$_3$) δ 154.0, 138.8, 135.3, 119.5, 115.0, 98.6, 85.7, 79.9, 66.9, 56.8, 56.5, 34.5, 34.4, 33.7, 28.7, 24.8, 11.3; MS (ESI) 337 [M+Na$^+$];

Synthesis of Aldol Adduct 25:

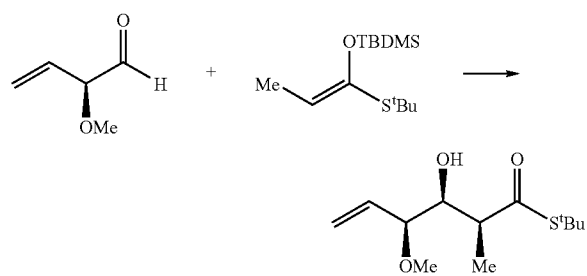

To a solution of aldehyde 23 (12.7 mmol) in 80 mL CH$_2$Cl$_2$ at −78° C. was added TiCl$_4$ (13.9 mL, 1.0 M solution in CH$_2$Cl$_2$. After 5 minutes, a solution of enol-ether 24 (13.9 mmol, 3.6 gm) in 10 mL CH$_2$Cl$_2$ was added slowly. After stirring for 2 hr, reaction mixture was diluted with ether and 1 M KOH was added. The organic layer was collected and washed with 10% HCl, 5% NaHCO$_3$ and saturated NaCl solution. The ether layer was dried with MgSO$_4$, filtered and concentrated. The resulting crude oil was purified with 20% ethyl acetate hexanes to yield 25 (1.9 gm, 61% yield). [α]D+ 40.2° (c 1.00, CHCl$_3$); IR(CH$_2$Cl$_2$) 3459, 2964, 1677, 1453, 1364, 957; $^1$H-NMR (500 MHz, CDCl$_3$) δ 5.78 (m, 1H), 5.21 (m, 2H), 3.68 (m, 1H), 3.40 (m, 1H), 3.21 (s, 3H), 2.64 (m, 1H), 2.42 (br-H, 1H), 1.36 (s, 9H), 1.11 (d, J=7.0 Hz, 3H); $^{13}$C-NMR (125 MHz, CDCl$_3$) δ 203.4, 135.0, 120.2, 83.9, 74.9, 56.9, 51.1, 48.3, 30.1, 13.0; MS (ESI) 269 [M+Na$^+$].

Compound 26:

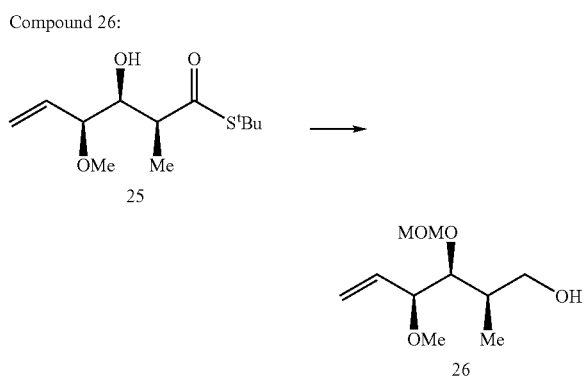

To a solution of alcohol 25 (0.864 gm, 3.43 mmol) in 10 mL CH$_2$Cl$_2$ at 0° C. was added diisopropyl ethyl amine (51.4 mmol, 15 mL). To the resulting solution was added MOMCl (34.3 mmol, 2.69 mL. Cooling bath was removed and the resulting solution was stirred for 12 hr. The reaction mixture was quenched with 10 mL of 0.2M aqueous NH$_4$OH, diluted extracted with ether. The organic layer was dried with MgSO$_4$, filtered, concentrated. The resulting crude oil was purified with 8% ethyl acetate/hexanes to afford corresponding MOM-ether (800 mg, 80% yield). D+24.8° (c 1.00, CHCl3); IR(CH$_2$Cl$_2$) 2963, 2822, 1678, 1455, 1363, 1152, 1129, 1104, 1032, 955; $^1$H-NMR (500 MHz, CDCl$_3$) δ 5.69 (m, 1H), 5.23 (m, 2H), 4.62 (d, J=6.5 Hz, 1H), 4.60 (d, J=6.5 Hz, 1H), 3.79 (m, 1H), 3.54 (m, 1H), 3.31 (s, 3H), 3.22 (s, 3H), 2.83 (m, 1H), 1.39 (s, 9H), 1.13 (d, J=6.5 Hz, 3H); $^{13}$C-NMR (125 MHz, CDCl3) δ 203.0, 135.4, 119.3, 98.6, 84.2, 81.5, 57.3, 56.6, 50.4, 48.1, 30.1, 13.7; MS (ESI) 313 [M+Na$^+$]. To a solution of LiAlH$_4$ (0.4 mL, 1M in THF) in 2 mL ether at 0° C. was added solution of MOM-ether (0.072 gm, 0.199 mmol) in 1.5 mL ether under argon. The resulting mixture was stirred at 0° C. for 2 hr and at rt for 1 hr and then excess of LiAlH$_4$ was quenched with ethyl acetate. The reaction mixture was diluted with ether and treated with saturated sodium potassium tartrate solution. The organic phase was separated and the aqueous phase was extracted twice with ether. The combined organic layer was dried with MgSO$_4$, filtered and concentrated to obtain the alcohol 26 as oil in pure form. $^1$H-NMR (500 MHz, CDCl$_3$) δ 5.58 (m, 1H), 5.23 (m, 2H), 4.81 (d, J=7.0 Hz, 1H), 4.62 (d, J=7.0 Hz, 1H), 3.60 (m, 2H), 3.45 (m, 2H), 3.35 (s, 31), 3.22 (s, 3H), 1.81 (m, 1H), 0.76 (d, J=8.5 Hz, 3H); $^{13}$C-NMR (125 MHz, CDCl$_3$) δ 134.9, 119.6, 99.1, 85.7, 80.8, 64.9, 56.8, 55.3, 36.8, 10.8; MS (ESI) 227 [M+Na$^+$].

Compound 20:

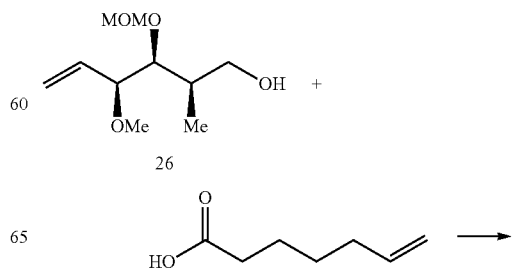

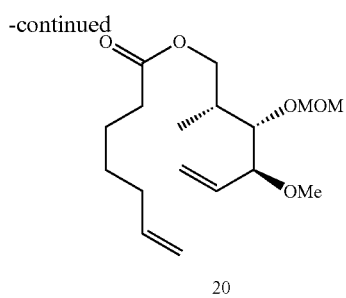

To a solution of alcohol 26 (0.022 gm, 0.107 mmol) and acid (36 □L, 0.269 mmol) in 2 mL CH$_2$Cl$_2$ was added DMAP (39 mg, 0.321 mmol) at 0° C. under argon. EDCI (61 mg, 0.321 mmol) was added and resulting solution was stirred for 30 min at 0° C. and 3 hr at rt. The reaction mixture was diluted with water and extracted with ether, dried with MgSO$_4$, concentrated. The crude oil was purified by FC (ethyl acetate: hexanes 1:9) to afford 20 in 88% yield (0.030 gm). [α]D–28.2° (c 1.0, CHCl$_3$); IR(CH$_2$Cl$_2$) 2932, 1735, 1157, 1033, 918; $^1$H-NMR (500 MHz, CDCl$_3$) δ 5.78 (m, 1H), 5.63 (m, 1H), 5.29 (m, 214), 4.96 (m, 2H), 4.80 (d, J=6.5 Hz, 1H), 4.67 (d, J=6.5 Hz, 1H), 4.04 (dd, J=11.0 Hz, J=8.0 Hz, 1H), 3.98 (dd, J=11.0 Hz, J=8.0 Hz, 1H), 3.62 (apparently t, J=7.5 Hz, 1H), 3.57 (dd, J=7.0 Hz, J=3.0 Hz, 1H), 3.38 (s, 3H), 3.27 (s, 3H), 2.30 (t, J=7.5 Hz, 3H), 2.05 (m, 3H), 1.63 (m, 2H), 1.40 (m, 2H), 0.91 (d, J=6.5 Hz, 3H); $^{13}$C-NMR (125 MHz, CDCl$_3$) δ 174.0, 138.8, 135.2, 119.5, 115.0, 98.6, 85.7, 79.9, 66.8, 56.8, 56.4, 34.5, 33.7, 28.7, 24.8, 11.3; MS (ESI) 337 [M+Na$^+$].

Compound 21:

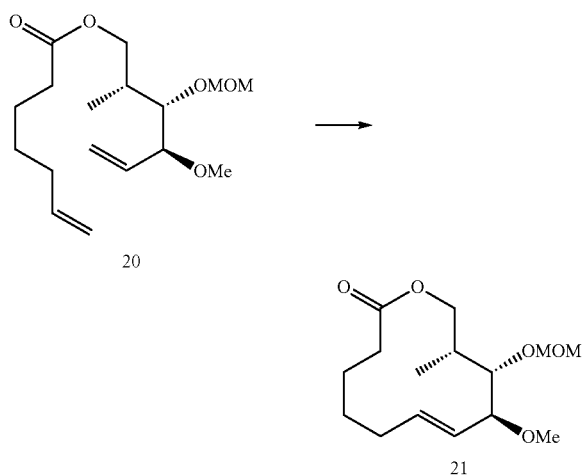

To a solution of ester 20 (15 mg, 0.047 mmol) in refluxing toluene (94 mL) was added Grubbs-II catalyst (8 mg, 0.0092 mmol). After stirring for 15 min, the reaction mixture was cooled to rt and filtered through a silica plug (hexane/EtOAc 3:1). Purification of the crude product by FC (hexane/EtOAc 9:1) afforded 21 in 67% yield. [α]D–14.0° (c 0.1, CHCl$_3$); IR(CH$_2$Cl$_2$) 1733, 1140, 1034; $^1$H-NMR (500 MHz, CDCl$_3$) δ 5.72 (m, 1H), 5.30 (dd, J=16 Hz, J=6.5 Hz, 1H), 4.91 (d, J=7.0 Hz, 1H), 4.69 (d, J=7.0 Hz, 1H), 4.45 (d, J=3 Hz, 1H), 4.43 (d, J=3 Hz, 1H), 3.57-3.46 (m, 3H), 3.41 (s, 3H), 3.30 (3, 3H), 2.44 (m, 1H), 2.19 (m, 1H), 2.12 (m, 1H), 1.86-1.67 (m, 5H), 1.18 (m, 1H), 0.93 (d, J=8.0 Hz, 3H); $^{13}$C-NMR (125 MHz, CDCl$_3$) δ 173.6, 134.8, 131.3, 98.7, 83.0, 81.3, 66.5, 57.2, 56.1, 34.9, 34.6, 30.1, 27.4, 22.8, 11.0; MS (ESI) 309 [M+Na$^+$].

Compound 22:

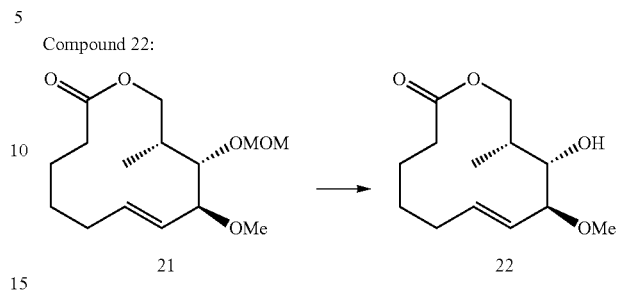

To a solution of 21 (4 mg, 0.014 mmol) in 1 mL CH$_2$Cl$_2$ at –20° C. was added trimethylsilyl bromide (0.014 mmol, 2 □l. After stirring for 20 minutes at –20° C. the reaction mixture was quenched with saturated NaHCO$_3$ solution, extracted with ether, dried with MgSO$_4$, filtered and concentrated. The crude product was purified by FC (3:1 hexanes: EtOAc) to afford 22 in 60% yield. IR(CH$_2$Cl$_2$) 3565, 2933, 2824, 1732, 1456, 1245, 1140, 1102; $^1$H-NMR (500 MHz, CDCl$_3$) δ 5.74-5.68 (m, 1H), 5.27 (dd, J=16.0 Hz, J=7.0 Hz, 111), 4.30 (dd, J=10.0 Hz, 2.0 Hz, 1H), 3.56 (app t, J=10.0 Hz, 1H), 3.50 (dd, J=9.5 Hz, J=2.5 Hz), 3.26-3.24 (m, 4H), 2.90 (br-H, 1H), 2.34 (m, 1H), 2.15 (m, 1H), 2.04 (m, 1H), 1.80-1.73 (m, 2H), 1.66-1.161 (m, 3H), 1.17 (m, 1H), 0.89 (d, J=6.5 Hz, 3H); MS (ESI) 265 [M+Na$^+$].

Compound 28:

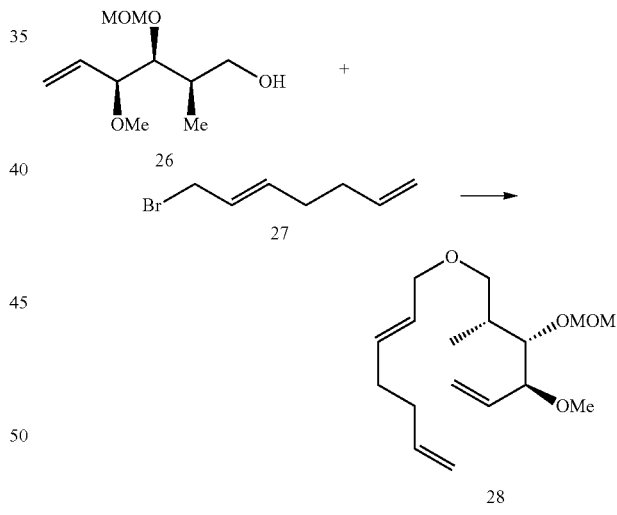

To a solution of 26 in 2 mL THF at 0° C. was added NaH (12 mg, 60% in mineral oil, 0.321 mmol) under argon. The reaction mixture was stirred for 30 minutes at 0° C., then warmed to rt and stirred for another 30 minutes. The solution was then cooled to 0° C. and the allyl bromide 27 in 1 mL THF was added, stirred for 12 hr with slowly warming to rt. It was then quenched with Saturated NH4Cl, extracted with ether, dried with MgSO$_4$, filtered and concentrated. Purification of the crude product by FC (hexanes:ethyl acetate 13:1) afforded 12 mg of 29. $^1$H-NMR (500 MHz, CDCl$_3$) δ 5.85-5.53 (m, 4H), 5.30-5.26 (m, 2H), 5.0 (m, 2H), 4.79 (d, J=6.0 Hz, 1H), 4.73 (d, J=6.0 Hz, 1H), 3.91 (m, 2H), 3.64 (m, 2H), 3.42 (m, 4H), 3.29 (m, 4H), 2.17 (m, 4H), 1.99 (m, 1H), 0.91 (d, J=7

Hz, 3H); $^{13}$C-NMR (125 MHz, CDCl$_3$) δ 138.5, 135.6, 133.7, 127.4, 119.2, 115.1, 98.7, 85.8, 80.5, 73.1, 71.9, 56.8, 56.4, 35.3, 33.6, 32.0, 11.5; MS (ESI) 321 [M+Na$^+$].

Compound 29:

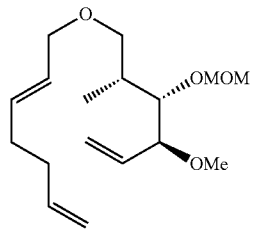

28

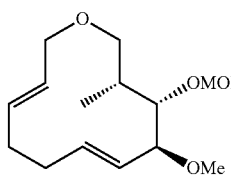

29

To a solution of ether 28 (8 mg, 0.026 mmol) in refluxing toluene (94 mL) was added Grubbs-II catalyst (4.4 mg, 0.0052 mmol). After stirring for 15 min, the reaction mixture was cooled to rt and filtered through a silica plug (hexane/EtOAc 3:1). Purification of the crude product by FC (hexane/EtOAc 9:1) afforded 29 in 56% yield. $^1$H-NMR (500 MHz, CDCl$_3$) δ 5.55-5.33 (3H, m), 5.18 (dd, J=14.5 Hz, J=8 Hz, 1H), 4.82 (d, J=7.0 Hz, 1H), 4.68 (d, J=7.0 Hz, 1H), 4.01 (dd, J=13.6 Hz, J=6.5 Hz, 1H), 3.88 (dd, J=12.5 Hz, J=6.0 Hz), 3.6-3.53 (m, 2H), 3.40 (s, 3H), 3.31-3.21 (m, 4H), 3.24 (dd, J=11.0 Hz, J=8.0 Hz), 2.28-2.15 (m, 5H), 0.9 (d, J=7.3 Hz, 3H); $^{13}$C-NMR (125 MHz, CDCl$_3$) δ 134.5, 133.6, 1314, 130.3, 98.6, 84.7, 80.7, 73.8, 72.6, 57.3, 56.3, 34.3, 32.4, 32.1, 12.1; MS (ESI) 289 [M+Na$^+$].

Compound 30:

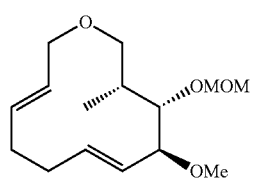

29

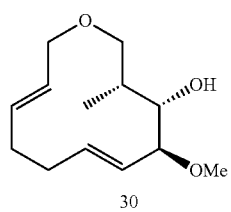

30

To a solution of 29 (4 mg, 0.014 mmol) in 1 mL CH$_2$Cl$_2$ at −20° C. was added trimethylsilyl bromide (0.014 mmol, 2 μl). After stirring for 20 minutes at −20° C. the reaction mixture was quenched with saturated NaHCO$_3$ solution, extracted with ether, dried with MgSO$_4$, filtered and concentrated. The crude product was purified by FC (3:1 hexanes:ethyl acetate)

to afford 30 in 60% yield. IR(CH$_2$Cl$_2$) 3565, 2933, 2824, 1732, 1456, 1245, 1140, 1102; $^1$H-NMR (500 MHz, CDCl$_3$) δ 5.56-5.49 (m, 1H), 5.42-5.32 (m, 2H), 5.10 (dd, J=15.0 Hz, J=7.5 Hz, 1H), 3.95 (dd, J=12.0, J=5.0 Hz, 1H), 3.84 (dd, J=13.5 Hz, J=7.5 Hz, 1H), 3.54 (dd, J=11.5 Hz, J=7.0 Hz, 1H), 3.36-3.21 (m, 6H), 2.78 (br-H, 1H), 2.33-2.00 (m, 5H), 0.93 (d, J=7.0 Hz, 3H); MS (ESI) 249 [M+Na$^+$].

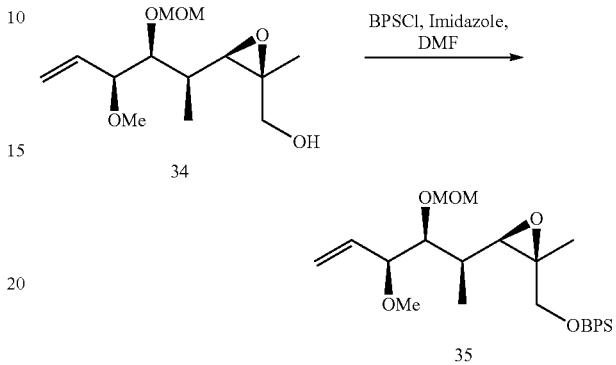

To a solution of epoxy-alcohol 34 (440 mg, 1.96 mmol) in 4 mL DMF was added imidazole (230 mg, 3.38 mol) followed by BPSCl (649 mL, 2.53 mmol) at 0° C. under argon. The reaction mixture was slowly warmed to room temperature over 30 minutes and stirred for additional 1 hour at this temperature or until the reaction was completed. The reaction mixture was diluted with ethyl acetate and washed with water. The organic layer was further washed with brine, dried with MgSO$_4$ and evaporated to yield crude product, which was separated using dichloromethane initially, then 1% ether/dichloromethane to 2% ether/dichloromethane to obtain BPS ether 35 in 85% yield. $^1$H-NMR (500 MHz, CDCl$_3$) δ 7.70-7.63 (m, 4H), 7.46-7.35 (m, 6H), 5.38-5.28 (m, 1H), 5.14 (dd, J=17.34 Hz, J=1.58 Hz, 1H), 5.07 (dd, J=10.40 Hz, J=1.58 Hz, 1H), 4.79 (d, J=6.62 Hz, 1H), 4.64 (d, J=6.62 Hz, 1H), 3.70 (d, J=11.35 Hz, 1H), 3.59 (d, J=11.35 Hz, 1H), 3.53-3.48 (m, 2H), 3.36 (s, 3H), 3.17 (s, 3H), 2.83 (d, J=9.77 Hz, 1H), 1.47 (m, 1H), 1.41 (s, 3H), 1.09 (s, 9H), 1.05 (d, J=6.94 Hz, 3H). MS (ESI) 521.3 [M+Na$^+$].

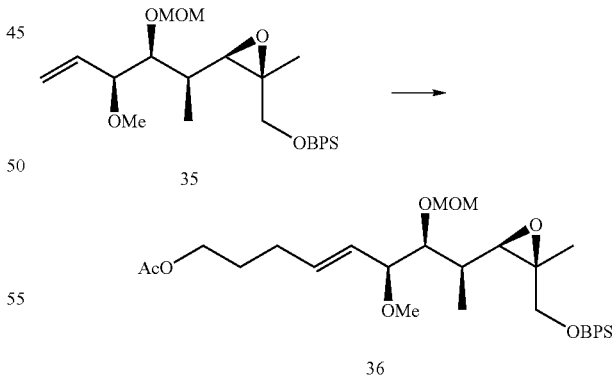

To a solution of epoxy-alkene 35 (375 mg, 0.751 mmol) and 4-pentenyl acetate (423 mg, 3 mmol) in 5 mL dichloromethane was added Grubbs II and the resulting solution was refluxed for 12 hr under argon. The reaction mixture was concentrated to under vacuum and directly loaded into the column. Column chromatography was started using dichloromethane initially, then 2.5% ethyl acetate/dichloromethane to 5% ethyl acetate/dichloromethane to obtain cross metathesis product 36 in 73% yield. $^1$H-NMR (500 MHz, CDCl$_3$) δ

7.68-7.62 (m, 4H), 7.43-7.32 (m, 6H), 5.56 (td, J=15.48 Hz, J=7 Hz, 1H), 4.99 (dd, J=15.48 Hz, J=7.5 z, 1H), 4.75 (d, 6.63 Hz. 1H), 4.61 (d, J=6.63 Hz, 1H), 3.96 (apt-t, J=6.63 Hz, 2H), 3.72 (d, J=10.6 Hz, 1H), 3.59 (d, J=10.61 Hz, 1H), 3.46 (m, 2H), 3.33 (s, 3H), 3.12 (s, 3H), 2.81 (d, J=9.73 Hz, 1H), 2.01 (s, 3H), 1.91 (apt-q, J=7.96 Hz, 2H), 1.56 (m, 2H), 1.49 (m, 1H), 1.38 (s, 3H), 1.06 (s, 9H), 1.02 (d, J=6.63 Hz, 3H).

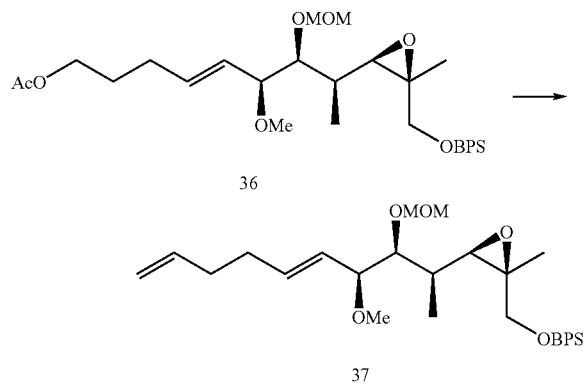

To a solution of acetate 36 (315 mg, 0.540 mg) in 3 mL methanol (anhydrous) was added solid potassium carbonate (82 mg) and the resulting solution was stirred at 0° C. under argon until the reaction was completed. Diluted with saturated NH$_4$Cl, extracted with ethyl acetate. The organic layer was washed with brine, dried with MgSO$_4$ and concentrated to afford crude alcohol. This crude alcohol was used without purification for the subsequent Swem oxidation. To a solution of oxalyl chloride (92 µL, 1.08 mmol) in 3 mL DCM was added DMSO (0.153 mL) at −78° C. under argon. After the stirring the resulting solution for 5 minutes a solution of crude alcohol in 2 (2×2) mL DCM was added. The resulting reaction mixture was stirred at −78° C. for 30 minutes. Then triethyl amine (0.376 mL) was added and stirred for 10 min. Dry ice-acetone bath was replaced by ice bath and stirred for 15 minutes. The resulting solution was diluted with water, extracted with ethyl acetate three times. The organic layer was washed with brine, dried with MgSO$^4$ and concentrated to yield crude product contaminated with triethylamine hydrochloride. The resulting crude product was dissolved in ethyl acetate and washed with water. The organic layer was dried with MgSO$_4$ and concentrated to yield aldehyde, which was used without further purification for olefination. To a suspension of methyltriphenyl phosphonium bromide (390 mg) dried overnight under P$_2$O$_5$ at 130° C.) in 2 mL THF was added NaHMDS at 0° C. under argon. The ice bath was removed and the reaction mixture was stirred at room temperature for 30 min. The resulting yellow solution was cooled to −10° C. and solution of aldehyde in THF was added and was stirred at −10° C. for 30 min and then quenched with Saturated NH$_4$Cl. The reaction mixture was diluted with water, extracted with ethyl acetate, dried with MgSO$_4$ and concentrated to yield olefin, which was purified by column chromatography using ethyl acetate/hexanes (10% to 12% ethyl acetate in hexanes) to afford the olefin 37 (yield 72% over three steps). $^1$H-NMR (500 MHz, CDCl$_3$) δ 7.68-7.62 (m, 4H), 7.43-7.32 (m, 6H), 5.65 (m, 1H), 5.55 (dt, J=14.45 Hz, J=6.62 Hz, 1H), 4.97-4.89 (m, 3H), 4.77 (d, J=6.62 Hz, 1H), 4.77 (d, J=6.62 Hz, 1H), 4.62 (d, J=6.62 Hz, 1H), 3.72 (d, J=10.72 Hz, 1H), 3.62 (d, J=10.72 Hz, 1H), 3.51-3.42 (m, 2H), 3.34 (s, 3H), 3.12 (s, 3H), 2.82 (d, J=9.96 Hz, 1H), 2.04-1.92 (m, 2H), 1.45 (m, 1H0, 1.38 (s, 3H0, 1.07 (s, 9H), 1.01 (d, J=6.94 Hz, 3H).

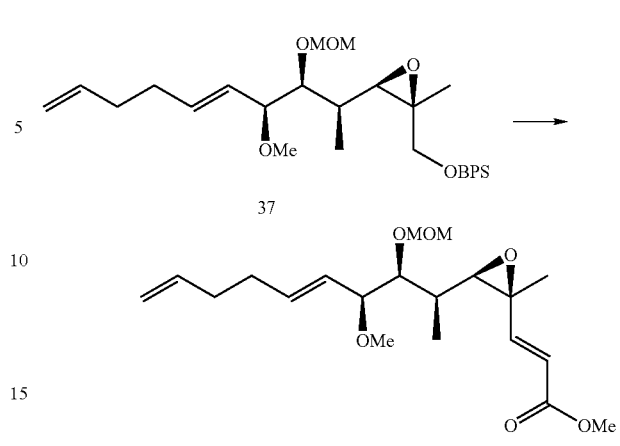

To a solution of BPS ether 37 (216 mg, 0.391 mmol) in 2 mL THF was added a solution of TBAF in THF (0.782 mL) at 0° C. under argon and resulting reaction mixture was stirred for 2 hours with slowly warming to room temperature. Then the reaction mixture was quenched with sat. NH$_4$Cl, extracted with ethyl acetate three times. The organic layers are combined, washed with brine, dried with MgSO$_4$ and concentrated to yield the crude product, which was purified using ethyl acetate hexanes (40% EtOAc in hexanes) to afford the epoxy alcohol in 96% yield.

This alcohol was used for the subsequent Swern oxidation. To a solution of oxalyl chloride (76 µL, 0.886 mmol) in 2 mL DCM was added DMSO (0.125 mL, 1.77 mmol) at −78° C. under argon. After the stirring the resulting solution for 5 minutes a solution of crude alcohol in 1.5×2 mL DCM was added. The resulting reaction mixture was stirred at −78° C. for 30 minutes. Then triethyl amine was added and stirred for 10 min. Dry ice-acetone bath was replaced by ice bath and stirred for 15 minutes. The resulting solution was diluted with water, extracted with ethyl acetate three times. The organic layer was washed with brine, dried with MgSO$_4$ and concentrated to yield crude product contaminated with triethylamine hydrochloride. The resulting crude product was dissolved in ethyl acetate and washed with water. The organic layer was dried with MgSO$_4$ and concentrated to yield aldehyde, which was used without further purification for olefination.

To a solution of crude aldehyde in CH$_2$Cl$_2$ was added methyl (triphenylphosphoranyllidene)-acetate (172 mg, 0.516 mmol) at 0° C. under argon. The resulting mixture was warmed to rt and stirred for 1 hr. The reaction mixture was concentrated and purified using ethyl acetate hexanes (17% ethyl acetate in hexanes) to obtain the conjugated ester 38 in 89% yield. $^1$H-NMR (500 MHz, CDCl$_3$) δ 6.80 (d, J=15.76 Hz, 1H), 5.97 (d, J=15.76 Hz, 1H), 5.75 (m, 1H), 5.63 (m, 1H), 5.09 (dd, J=15.45 Hz, J=8.83 Hz, 1H), 5.02-4.92 (m, 2H), 4.78 (d, J=6.94 Hz, 1H), 4.60 (d, J=6.94 Hz, 1H), 3.71 (s, 3H), 3.49 (apt-t, J=7.88 Hz, 1H), 3.38-3.30 (m, 4H), 3.17 (s, 3H), 3.02 (d, J=9.46 Hz, 1H), 2.12-2.07 (m, 4H), 1.53 (m, 1H), 1.45 (s, 3H), 1.05 (d, J=6.62 Hz, 3H).

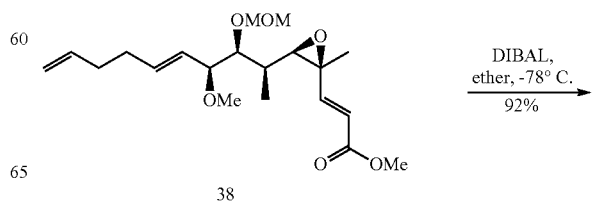

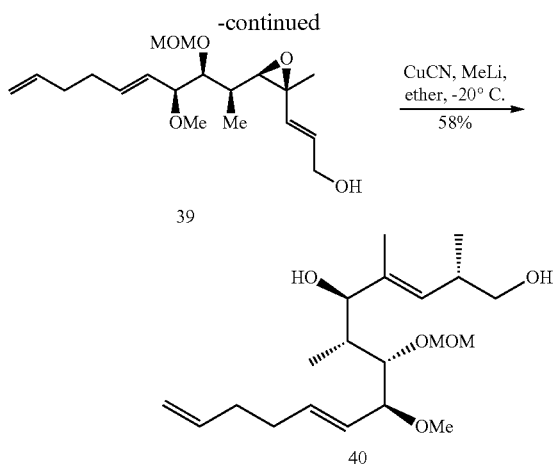

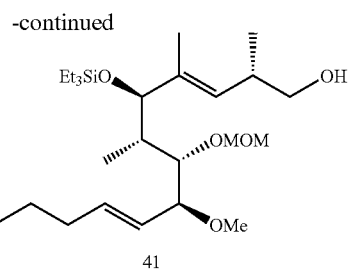

To a solution of ester 38 (146 mg, 0.396 mmol) in 8 mL ether was added a solution of DIBAL in hexanes (0.872 mL, 0.872 mmol) over 1.5 hr using syringe pump at −78° C. under argon. The resulting solution was stirred for additional 2 hrs. Then the reaction mixture was quenched with sequential addition of 97 μL of methanol followed by 10 mL of sat. Rochelle's salt The dry ice bath was replaced by ice bath and the solution was allowed to warm to rt. The reaction mixture was extracted with ether (three times). The organic layers are combined, then washed with brine, dried with MgSO$_4$ and concentrated. Purification by chromatography on silica gel deactivated by prior elution with 1% Et$_3$N in hexanes (40% ethyl in hexanes) gave 125 mg of allylic alcohol (92% yield). This allylic alcohol was used in cuprate addition reaction in next step.

To a suspension of CuCN (93 mg, 1.048 mmol, CuCN was taken in flame dried flask) in 2 mL ether was added a solution of MeLi in ether (0.952 mL, 1.048 mmol) over 1 hr at −20° C. under argon. During the addition of MeLi, the color of the solution became yellow and then faded away to colorless. The reaction mixture was stirred for additional 40 mim after the addition of MeLi at −20° C. To this clear solution was added slowly a solution of epoxide in 0.5 mL ether (30 mg, 0.104 mmol). The resulting solution was stirred for 30 min at −20° C., then TLC indicated the completion of reaction. The reaction mixture was quenched with 5 mL of 1:1 mixture of sat. NH$_4$Cl and 3M NH$_4$OH, warmed to rt, extracted with ethyl acetate, dried with MgSO$_4$ and concentrated. Column chromatography using ethyl acetate in hexanes (30% to 40% to 50% to 60% EtOAc/Hexanes) afforded the major isomer 40 in 58% yield. $^1$H-NMR (500 MHz, CDCl$_3$) δ 5.83 (m, 1H), 5.73-5.67 (m, 1H), 5.32-5.22 (m, 2H), 5.05-4.94 (m, 2H), 4.85 (d, J=6.31 Hz, 1H), 4.67 (d, J=6.31 Hz, 1H), 4.08 (d, J=6.62 Hz, 1H), 3.59 (apt-t, J=8.20 Hz, 1H), 3.51 (m, 1H), 3.45 (dd, J=4.10 Hz, J=2/84 Hz, 1H), 3.41 (s, 3H), 3.36 (apt-t, J=10.40 Hz, 1H), 3.22 (s, 3H), 2.69-2.50 (m, 3H), 2.17 (m, 4H), 1.87 (m, 1H), 1.58 (s, 3H), 0.96-0.90 (m, 6H). MS (ESI) 379.4 [M+Na$^+$].

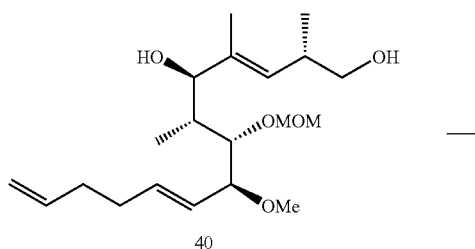

To a solution of diol 40 in 8 mL CH$_2$Cl$_2$ (317 mg, 0.891 mmol) containing 2,4,6-collidine (1.782 mmol, 0.236 mL) was added AcCl (1.070 mL, 76 μL) at −78° C. under argon. The resulting solution was stitted for 3 hr at −78° C., then slowly warmed to 0° C. and sat. NaHCO$_3$ was added. Reaction mixture was diluted with water, extracted with ethyl acetate (three times), organic layers are combined, washed with brine, dried with MgSO$_4$ and concentrated to afford the crude product. Crude product was taken for the next step. To this crude mono-protected alcohol in 5 mL CH$_2$Cl$_2$ was added pyridine (0.288 mL) followed by TESOTf (0.403 mL) at 0° C. The resulting solution was stirred for 30 min, by then TLC indicated the completion of reaction. The reaction mixture was quenched with sat. NaHCO$_3$, diluted with water, extracted with ethyl acetate (three time), organic layers were combined, washed with brine, dried with MgSO$_4$ and concentrated to afford the crude product. This crude product was dissolved in 4 mL of MeOH and K$_2$CO$_3$ (147 mg) was added at 0° C. and stirred at this temperature until the reaction was complete. Diluted with sat. NH$_4$Cl, extracted with ethyl acetate (three times), organic layers are combined, washed with brine, dried with MgSO$_4$ and concentrated to afford the crude product, which was purified with 25% ethyl acetate in hexanes to primary alcohol 41 in 89% yield. $^1$H-NMR (500 MHz, CDCl$_3$) δ 5.80-5.70 (m, 1H), 5.70-5.60 (m, 1H), 5.20 (d, J=9.46 Hz, 1H), 5.13 (dd, J=15.45 Hz, J=8.51 Hz, 1H), 5.02 (dd, J=17.02 Hz, J=1.89 Hz, 1H), 4.97 (dd, J=10.09 Hz, J=1.89 Hz, 1H), 4.89 (d, J=7.57 Hz, 1H), 4.58 (d, J=7.57 Hz, 1H), 3.88 (d, J=10.40 Hz, 1H), 3.55-3.45 (m, 2H), 3.41 (s, 3H), 3.35 (dd, J=11.03 Hz, J=7.88 Hz, 1H), 3.29 (d, J=7.88 Hz, 1H), 3.18 (s, 3H), 2.63 (m, 1H), 2.20-2.12 (m, 4H), 1.75 (m, 1H), 1.53 (s, 3H), 1.01-0.89 (m, 15H), 0.57 (q, J=7.88 Hz. 6H).

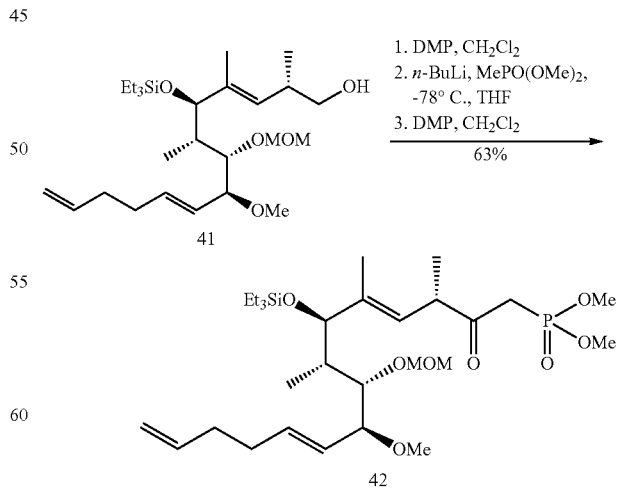

To a solution of alcohol 41 (374 mg, 0.795 mmol) in 3 mL CH$_2$Cl$_2$ was added pyridine (4.77 mmol, 0.472 mL) followed by solution of DMP in CH$_2$Cl$_2$ (15% solution in dichloromethane, 1.59 mmol, 0.675 gm) at 0° C. and stirred for 5 minutes. Ice bath was removed and the reaction mixture was stirred at rt for 30 min. By then TLC indicated the completion of reaction. Excess of isopropanol was added and stirred for additional 10 minutes. Then, sat. NaHCO$_3$ followed by 1N Na$_2$S$_2$O$_3$ was added, extracted with ether (three times), organic layers are combined, washed with brine, dried with MgSO$_4$ and concentrated to afford the crude product, which was taken for next step.

To a solution of phosphonate (3.97 mmol, 0.430 mL) in 8 mL THF was added a solution of nBuLi in hex (3.57 mmol, 2.2 mL) at −78° C. under argon and stirred for 45 minutes. Then a solution of aldehyde in (2×3 mL) THF was added to the solution while cooling at −78° C. The resulting solution was stirred for 1 hr at −78° C. TLC indicated completion of reaction. The reaction mixture was warmed to −40° C. and saturated NH$_4$Cl was added. The reaction mixture was extracted with ethyl acetate (three times), organic layers are combined, washed with brine, dried with MgSO$_4$ and concentrated to afford the crude product, which was purified using ethyl acetate in hexanes (70% to 100% ethyl acetate in hexanes). The resulting secondary alcohol was oxidized using DMP following the similar procedure used to oxidize the primary alcohol to aldehyde.

To a solution of keto-phosphonate 42 (296 mg, 0.501 mmol) in 4 mL CH$_3$CN was added LiCl (21 mg) followed by DBU (74 µL, 0.501 mmol) and the resulting solution was stirred for 15 min at rt. Then a solution of glutarimide aldehyde in 2 mL CH$_3$CN was added to the reaction mixture and reaction mixture was stirred for 2 hrs. Saturated NH$_4$Cl was added. The reaction mixture was extracted with ethyl acetate (three times), organic layers are combined, washed with brine, dried with MgSO$_4$ and concentrated to afford the crude product, which was purified using ethyl acetate in hexanes (40% ethyl acetate in hexanes) to afford the corresponding product 43 in 94% yield. $^1$H-NMR (500 MHz, CDCl$_3$) δ 8.01 (br-s, 1H), 6.76 (dd, J=15.76 Hz, J=8.20 Hz, 1H), 6.26 (d, J=15.76 Hz, 1H), 5.78 (m, 1H), 5.63 (m, 1H), 5.32 (d, J=9.77 Hz, 1H), 5.07-4.95 (m, 3H), 4.61 (d, J=6.31 Hz, 1H), 4.58 (d, J=6.31 Hz, 1H), 3.94 (d, J=10.09 Hz, 1H), 3.52-3.42 (m, 2H), 3.34 (s, 3H), 3.20-3.09 (m, 4H), 2.69 (m, 2H), 2.34-2.25 (m,

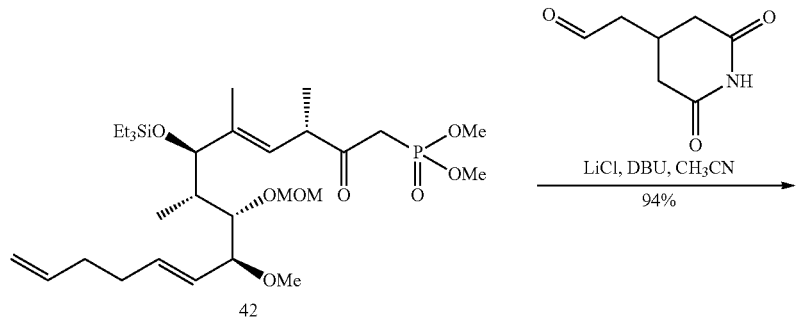

42

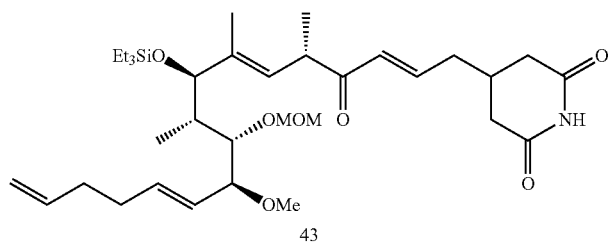

43

5H), 2.19-2.11 (m, 4H), 1.75 (m, 1H), 1.59 (s, 3H), 1.17 (d, J=6.94 Hz, 3H), 0.95-0.88 (m, 9H), 0.55 (q, J=8.20 Hz, 6H).

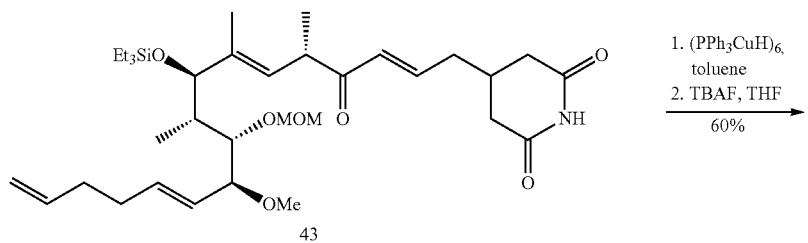

43

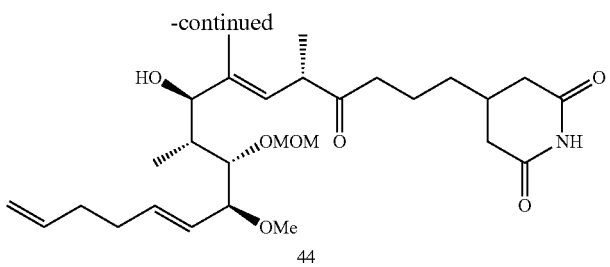

44

To a solution of conjugated ketone 43 (127 mg, 0.205 mmol) in 5 mL degassed toluene was added Stryker reagent (321 mg, 0.164 mmol) and stirred for 1 hr at rt. The reaction mixture was exposed to air, excess of hexanes and 40 µL of water added and resulting solution was stirred for 30 min at rt. Next, the reaction mixture was evaporated to dryness and directly loaded into column for purification. Column chromatography purification provided 96 mg of corresponding compound in 75% yield.

To this compound (100 mg, 0.160 mmol) in 3 mL THF was added a solution of TBAF in THF (1.0 M in THF, 0.160 mL) at 0° C. and the resulting solution was stirred for 3 hr at 0° C. Then sat. NH$_4$Cl was added, diluted with water, extracted with ethyl acetate (three times), organic layers are combined, washed with brine, dried with MgSO$_4$ and concentrated to afford the crude product, which was purified using ethyl acetate in hexanes (70% ethyl acetate in hexanes) to afford the corresponding product 44 in 77% yield. $^1$H-NMR (500 MHz, CDCl$_3$) δ 8.06 (br-s, 1H), 5.82-5.68 (m, 2H), 5.44 (d, J=10.09 Hz, 1H), 5.31 (dd, J=16.08 Hz, J=8.51 Hz, 1H), 5.01 (d, J=17.02 Hz, 1H), 4.96 (d, J=10.09 Hz, 1H), 4.79 (d, J=6.62 Hz, 1H), 4.72 (d, J=6.62 Hz, 1H), 4.21 (br-s, 1H), 3.65 (apt-t, J=6.62 Hz, 1H), 3.53 (apt-t, J=4.42 Hz), 3.41-3.34 (m, 4H), 3.27 (s, 3H), 2.70 (d, J=4.10 Hz, 1H), 2.66 (d, J=4.10 Hz, 1H), 2.55-2.46 (m, 1H), 2.42-2.34 (m, 1H), 2.27-2.04 (m, 7H), 1.91 (m, 1H), 1.61 (s, 3H), 1.56 (m, 2H), 1.33 (m, 2H), 1.12 (d, J=6.6s Hz, 3H), 0.82 (d, J=7.25 Hz, 3H). MS (ESI) 530.3 [M+Na$^+$].

To a solution of alcohol 44 (65 mg, 0.128 mmol) in 2 mL dichloromethane containing Mukaiyama reagent (39 mg, 0.153 mmol) were added acrylic acid (9.6 µL, 0.141 mmol) followed by Et$_3$N (35 µL, 0.256 mmol). The resulting mixture was refluxed for 2 hr, then cooled to rt, evaporated to dryness and directly loaded into column. Column chromatography purification provided 30 mg of corresponding compound in 50% yield.

To a solution of this compound (10 mg, 0.0178 mmol) was added TMSBr (3.5 µL, 0.0267 mmol) at −20° C. under argon. The resulting solution was stirred at −20° C. for 30 min. Then diluted with ethyl acetate, quenched with 5% aqueous NaHCO$_3$, layers were separated, organic layers were combined, washed with brine, dried with MgSO$_4$ and concentrated to afford the crude product, which was purified using ethyl acetate in hexanes (70% ethyl acetate in hexanes) to afford the corresponding product 45 in 77% yield. $^1$H-NMR (500 MHz, CDCl$_3$) δ 7.89 (br-s, 1H), 6.37 (dd, J=17.34 Hz, J=1.26 Hz, 1H), 6.10 (dd, J=17.34 Hz, J=10.40 Hz, 1H), 5.85-5.64 (m, 3H), 5.42 (d, J=10.09 Hz, 1H), 5.27 (d, J=8.51 Hz, 1H), 5.19 (dd, J=15.76 Hz, J=8.82 Hz, 1H), 5.02 (dd, J=17.02 Hz, J=2.21 Hz, 1H), 4.98 (dd, J=10.40 Hz, J=1.26 Hz, 1H), 4.72 (d, J=6.94 Hz, 1H), 4.63 (d, J=6.94 Hz, 1H), 3.57 (apt-t, J=7.25 Hz, 1H), 3.41 (s, 3H), 3.33 (dd, J=10.09 Hz, J=7.25 Hz, 1H), 3.28 (dd, J=6.94 Hz, J=3.15 Hz, 1H), 3.22 (s, 3H), 2.70 (d, J=4.10 Hz, 1H), 2.67 (d, J=4.10 Hz, 1H), 2.51-2.43 (m, 1H), 2.40-2.32 (m, 1H), 2.27-2.05 (m, 8H), 1.65 (s, 3H), 1.54 (m, 2H), 1.32 (m, 2H), 1.13 (d, J=6.94 Hz, 3H), 0.91 (d, J=6.94 Hz, 3H). MS (ESI) 584.2 [M+Na$^+$].

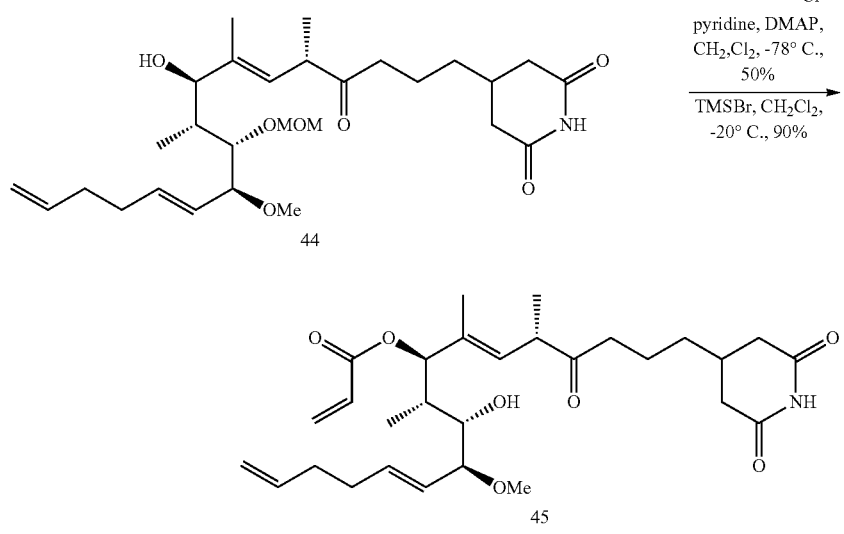

Biological Data

Material and Methods

Chamber Cell Migration Assay

Cell migrations of Ovcar3 ovarian cancer cells were assayed with 8 µm of microporous 6.5-mm transwell plates (Corning). 100 wl of 5×10$^4$ cells in serum-free RPMI1640 medium containing 0.5% BSA were added to the upper chamber and 600 µl of medium with 10% fetal bovine serum was added to the lower chamber. Transwells were incubated for 12 hours with following concentrations of chemical compounds in both upper and lower chambers (1 nM, 10 nM, 100 nM 1 µM, 10 µM). Cells on the inside of the transwell inserts were removed with a cotton swab, and cells on the under side of the insert were fixed and stained. Photographs of three random regions were taken and the number of cells was counted to calculate the average number of cells that had transmigrated. Data shown is the average of at least three experiments.

Wound Healing Assay

The tumor cells (Ovcar3) were seeded into 24-multiwell plates (Becton-Dickinson) and cultivated until the cells formed a confluent monolayer. Wounds were set by horizontally scratching the monolayer with a sterile pipette tip. The cells were thereafter washed twice with Phosphate Buffered Saline (PBS) to remove detached cells. Growth media was then added containing 250 nM of the chemical compounds (21, 22, and 30) and incubated at 37° C. The cells were photographed at the beginning of the experiment and after 24 to assess the progression of cell migration into the wound.

Cell Proliferation Assay.

5×10$^3$ Ovcar3 cells were plated into wells of 96 multi-well plates (Becton-Dickinson) using M5 as growth media in the presence or absence of chemical compounds (21, 22 and 30) in concentrations of 1 nM, 10 nM, 100 nM, 1000 nM, 10000 nM, 100000 nM and then incubated at 37° C. for 72 hours. In the last 20 hours, sodium 3'-[1-(phenylamino-carbonyl)-3,4-tetrazolium]-bis(4-methoxy-6-nitro) benzene sulfonic acid hydrate (XTT) was added and optical absorbance at 490 nm were measured. As reference wavelength 650 nm was used. The number of living cells, thus the total metabolic activity, directly correlates to the amount of orange formazan formed. The result was expressed as percentage of the control.

Results

Figure 2A:
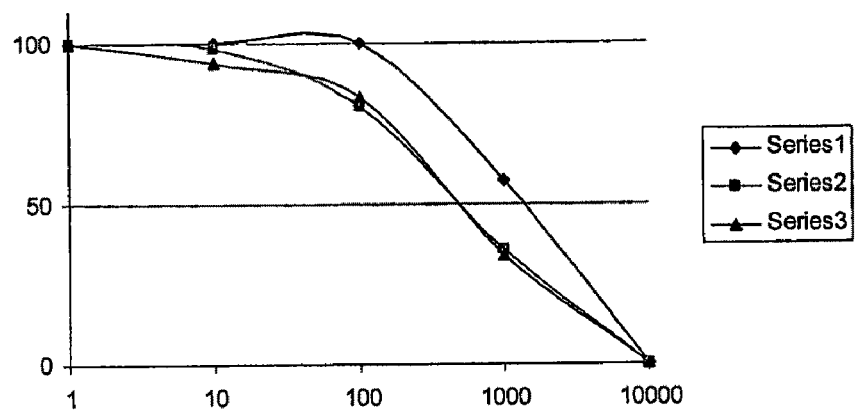
FIG. 2 depicts transwell assay experiments for inventive compounds: (A) compound 22 ($IC_{50}$=738±267 nM); (B) compound 30 ($IC_{50}$=27±5.8 nNM); and (C) compound 21 ($IC_{50}$=75±6.5 nM).
Figure 2B:
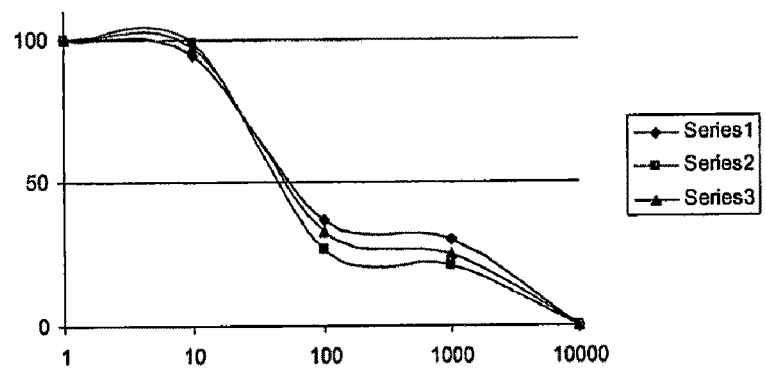
Figure 2C:
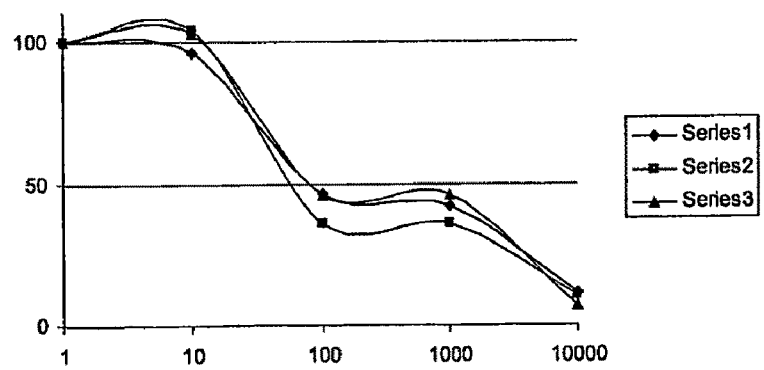
Figure 3:
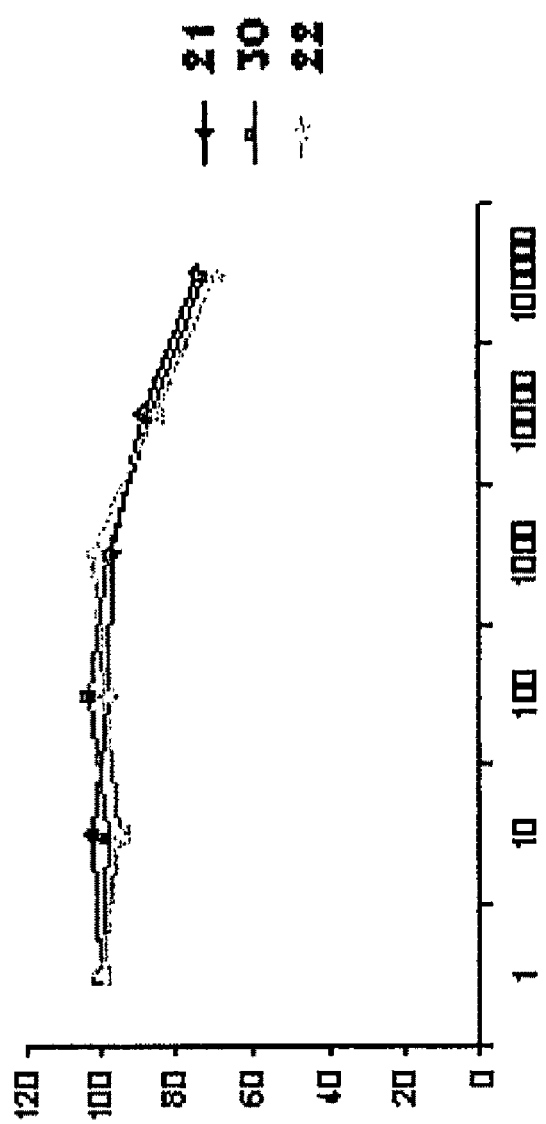
FIG. 3 depicts XTT-assay experiments for compounds 22, 30 and 21.
Figure 4:
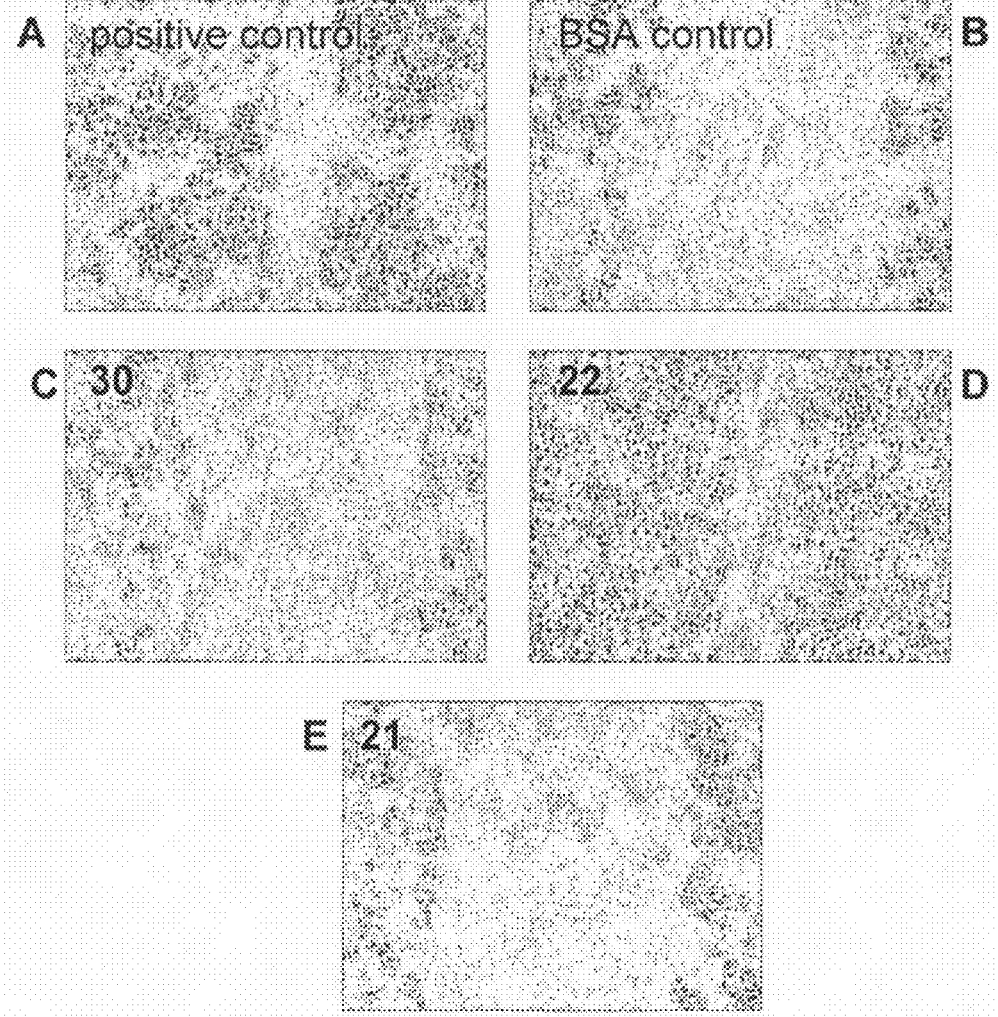
FIG. 4 depicts wound healing assay experiments for compounds 22, 30 and 21.
Figure 5:
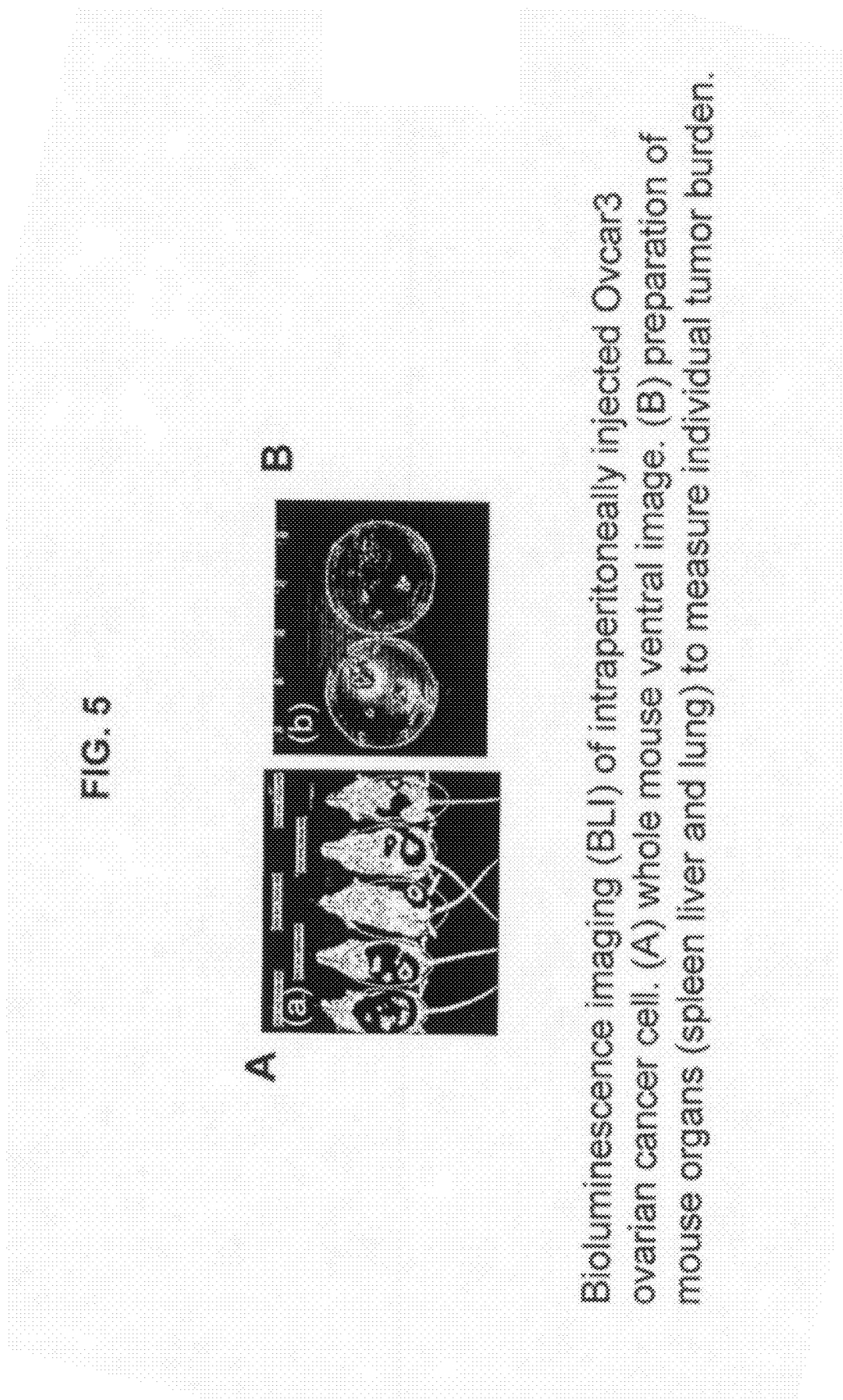
FIG. 5 depicts bioluminescence imaging (BLI) of intraperitoneally injected Ovcar3 ovarian cancer cell. (A) whole mouse ventral image. (B) preparation of mouse organs (spleen liver and lung) to measure individual tumor burden.

Compound 21 and 30 were highly potent in inhibiting the migration of human ovarian cancer cells in the transwell assay (FIG. 2) and in the wound healing assay (FIG. 4). After 12h 50% of the migration was inhibited in the transwell assay at a concentration of 27 nM for compound 30 and by a concentration of 75 for compound 21 (FIG. 2). At the concentration of 250 nM both 21 and 30 inhibited the closure of the scar in the wound healing assay (FIG. 4). The proliferation assay shows, that the inhibition of cell migration is not due to the toxicity, since cell proliferation decreases slightly after only after a two log concentration increase (FIG. 3).

In Vivo Metastatic Models

Figure 6:
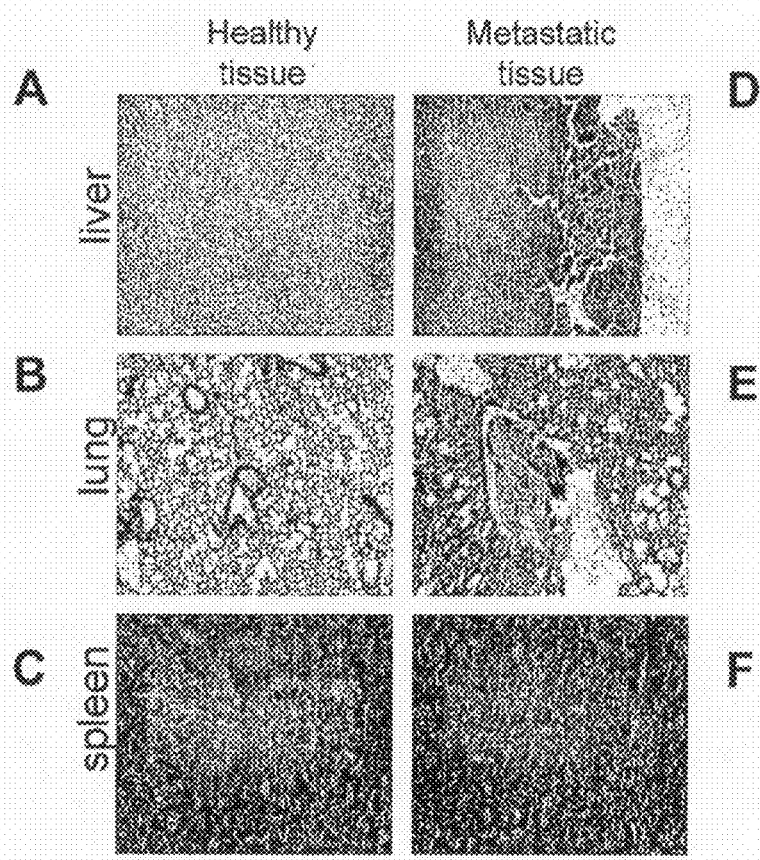
FIG. 6 depicts histological sections of mouse liver, lung and spleen, demonstrating the infiltration of Ovcar3 ovarian cancer cells into the tissue. Figures A-C: healthy mice. Figures D-F: intraperitoneally injected ovarian metastatic mice.

The human ovarian tumor cell line OVCAR3 was transduced with a triple fusion gene HSV-TK/eGFP/FLuc, expressing thymidine kinase, enhanced green fluorescence protein and firefly luciferase. Whole animal imaging by luciferase bioluminescence (FIG. 5A), allowed identification and quantification of disseminated tumor. We quantified the tumor burden in each organ, by sacrificing the mouse shortly after luciferin injecting and imaging of the dissected organs (lung, liver and spleen) (FIG. 5B). In all instances tumor engraftment was initiated with 1–5×10$^7$ cells and the recipients received 3 Gy irradiation 10 days before tumor engraftment. These tumor cells generated bulky omental metastases with diffuse microscopic peritoneal carcinomatosis causing ascites (FIG. 5A) with, significant pleural effusion and liver, lung and paraaortic metastases (FIG. 6).

Figure 7:
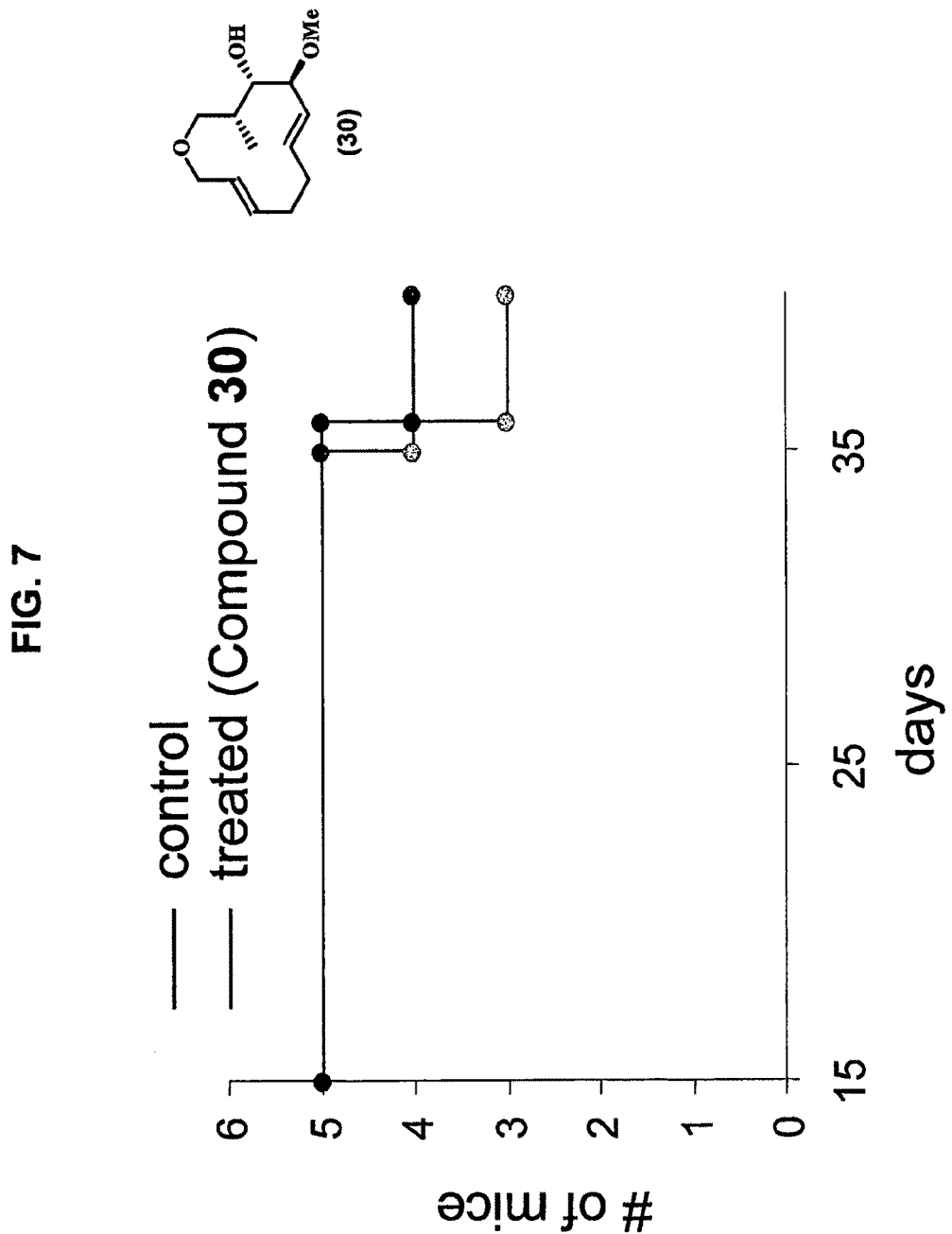
FIG. 7 depicts a survival-curve graph of mice treated with isomigrastatin analog (30) in an ovarian xenograph model.
Figure 8:
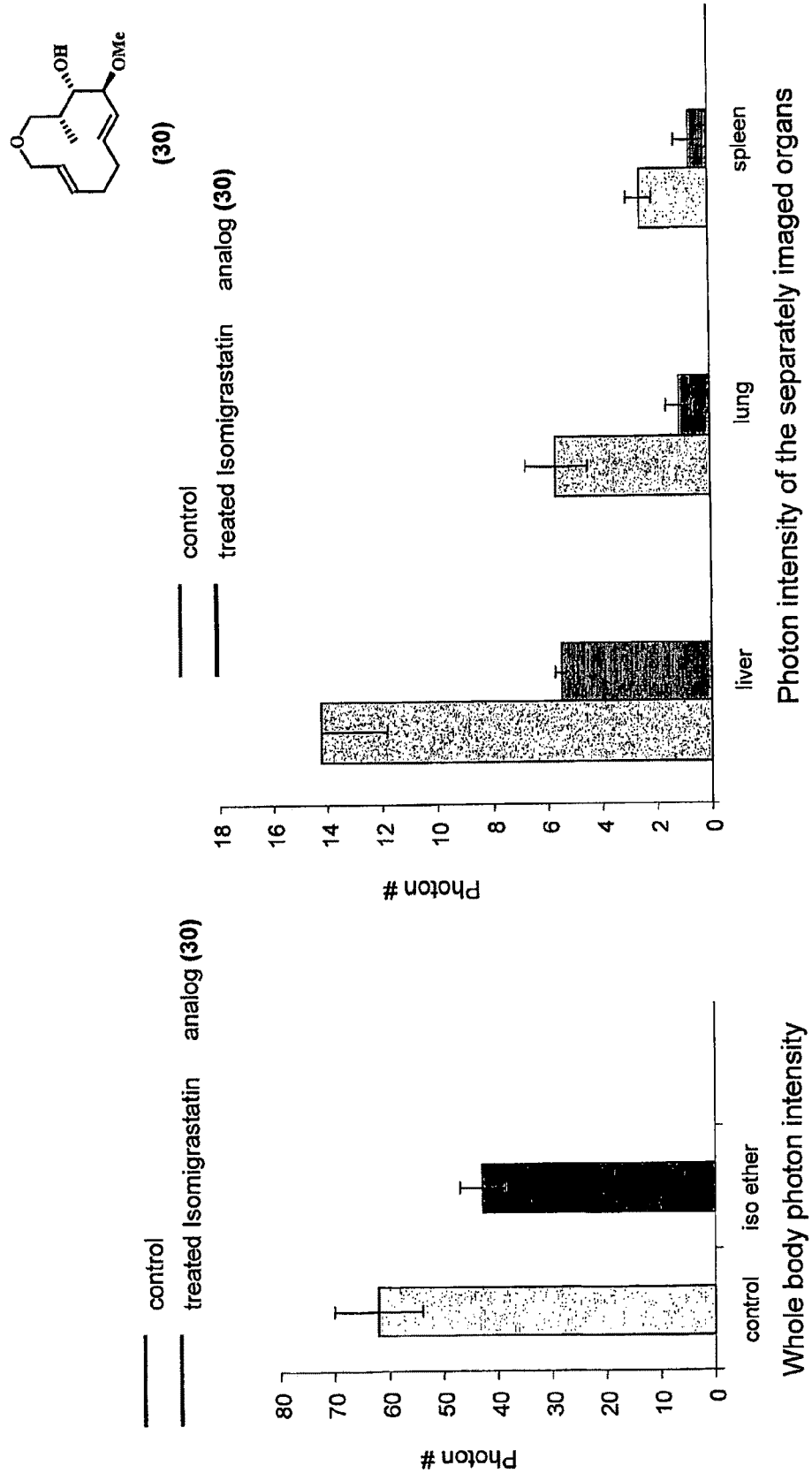
FIG. 8 depicts Luciferase tumor imaging experiments for isomigrastatin analog (30) in an ovarian xenograph model. The experiment shows significant inhibition of tumor metastasis in the treated mice.
Figure 9:
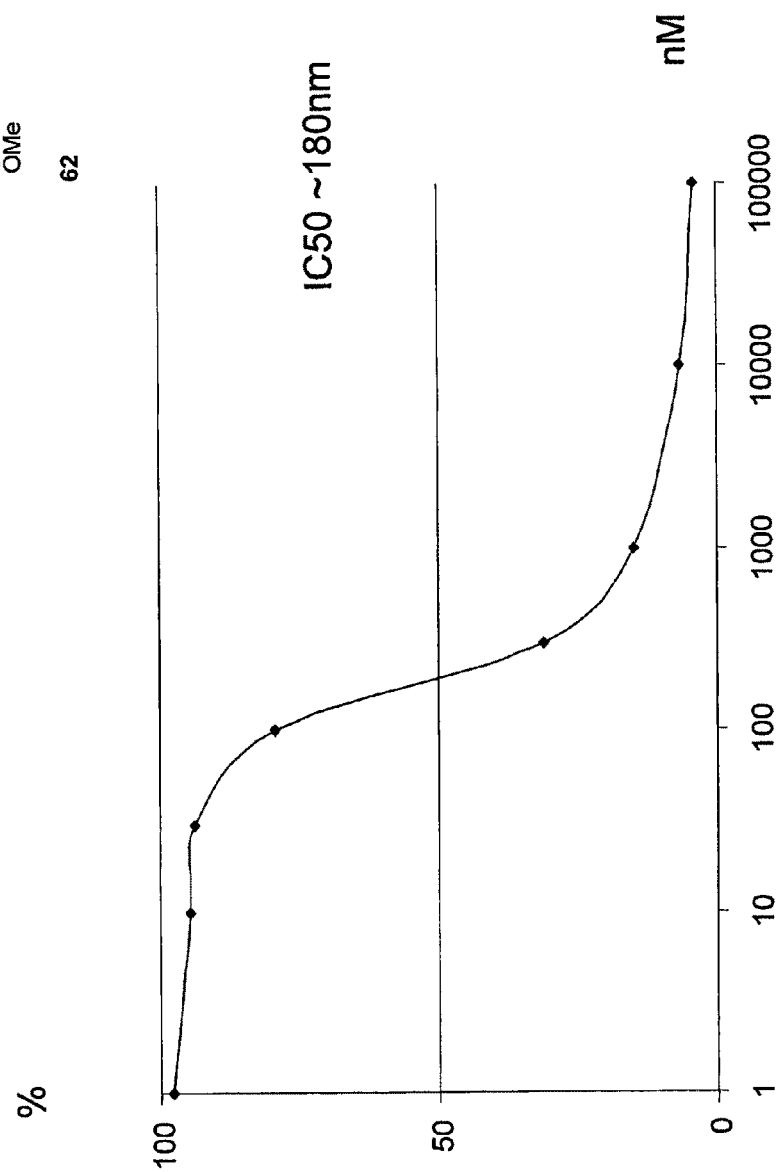
FIG. 9 depicts a transwell assay experiment for inventive migrastatin analog (62).

The present invention demonstrates that isomigrastatin analogs are potent inhibitors of cell migration and cell proliferation in human cancer cells (FIGS. 7, 8, and 9). For example, we identified ovarian cancer cells as a responsive cancer cell line. Accordingly, there is provided a method for treating and/or lessening the severity of cancer in a subject in need thereof comprising administering an effective amount of a compound of formula I. In certain embodiments, the method is for treating and/or lessening the severity of metastatic cancer. In certain embodiments, the subject is a mammal. In certain exemplary embodiments, the subject is human. In certain exemplary embodiments, the cancer is ovarian cancer. In certain exemplary embodiments, the cancer is metastatic ovarian cancer.

In addition, compounds of the invention have unexpectedly been shown to inhibit cell proliferation. Therefore we suggest, that we can utilize the inventive compounds as cytotoxic agents (i.e., agents that inhibit cell division and are potentially useful in cancer chemotherapy).

In summary, compounds of the invention have been shown to have potent activity in human cancer (in vivo and in vitro). Compounds of the invention have been shown to exert their activity, not only as cell migration inhibitors, but also by inhibiting cell proliferation.

REFERENCES

1. G. Fenteany, S. Zhu, Current Topics in Medicinal Chemistry (Sharjah, United Arab Emirates) 2003, 3, 593-616.
2. C. Khosla, P. Licari, J. Carney, in U.S. Pat. Appl. Publ., (Kosan Biosciences, Inc., USA). Us, 2002, p. 7 pp.
3. E. J. Woo, C. M. Starks, J. R. Carney, R. Arslanian, L. Cadapan, S. Zavala, P. Licari, Journal of Antibiotics 2002, 55, 141-146.
4. C. Gaul, J. T. Njardarson, D. Shan, D. C. Dorn, K.-D. Wu, W. P. Tong, X.-Y. Huang, M. A. S. Moore, S. J. Danishefsky, Journal of the Anerican Chemical Society 2004, 126, 11326-11337.
5. J. T. Njardarson, C. Gaul, D. Shan, X.-Y. Huang, S. J. Danishefsky, Journal of the American Chemical Society 2004, 126, 1038-1040.
6. C. Gaul, J. T. Njardarson, S. J. Danishefsky, Journal of the American Chemical Society 2003, 125, 6042-6043.
7. C. Gaul, S. J. Danishefsky, Tetrahedron Letters 2002, 43, 9039-9042.

Migrastatin Ether

To further develop and explore the potential of migrastatin-based analogs as an anti-metastatic we have embarked on the selective preparation of plasma stable derivatives. It is reasonable to hypothesize that the macro-ethers, which lacks the ester functionality would be stable in the mice plasma, and therefore would permit their in vivo studies. We set out first to achieve the chemical synthesis of these ethers. Following the previously developed sequence of reactions the primary alcohol 52 was prepared, which was transformed to corresponding allylic bromide in 68% yield in a straight-forward manner. Alkylation of this bromide 53 was performed using 6-heptenol to obtain the RCM precursor. Ring closure under the influence of Grubbs II followed by TBS removal gave our first macro-ether 61, which was tested stable in mice plasma as we had predicted. This compound has been extensively investigated in vitro and in vivo to evaluate its potential as cancer cell migration inhibitors. To further probe the influence of the free hydroxyl group of 61, in a desire to introduce "CT$_3$" aiming to use it in target identification purpose, it was methylated. The IC$_{50}$ value of 62 is 180 nM (against Ovcar3), suggesting its potential utility in target identification purpose.

As an additional probe into structure-activity relationships, the unsaturated analog of 57 was prepared via an analogous route. Bromide 53 was displaced with the alkoxide derived from 2,6-heptadien-1-ol, to afford RCM precursor 55 in 71% yield. RCM of 55 proceeded smoothly, albeit in somewhat diminished yield compared to the saturated analog, to afford the TBS protected macrocycle 56 in 39% yield. Removal of the TBS group proceeded uneventfully to yield the fully unsaturated macroether core (57) of migrastatin, which gave an $IC_{50}$ value of 180 nM in the same assay.

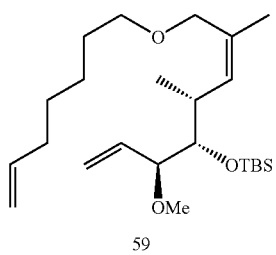

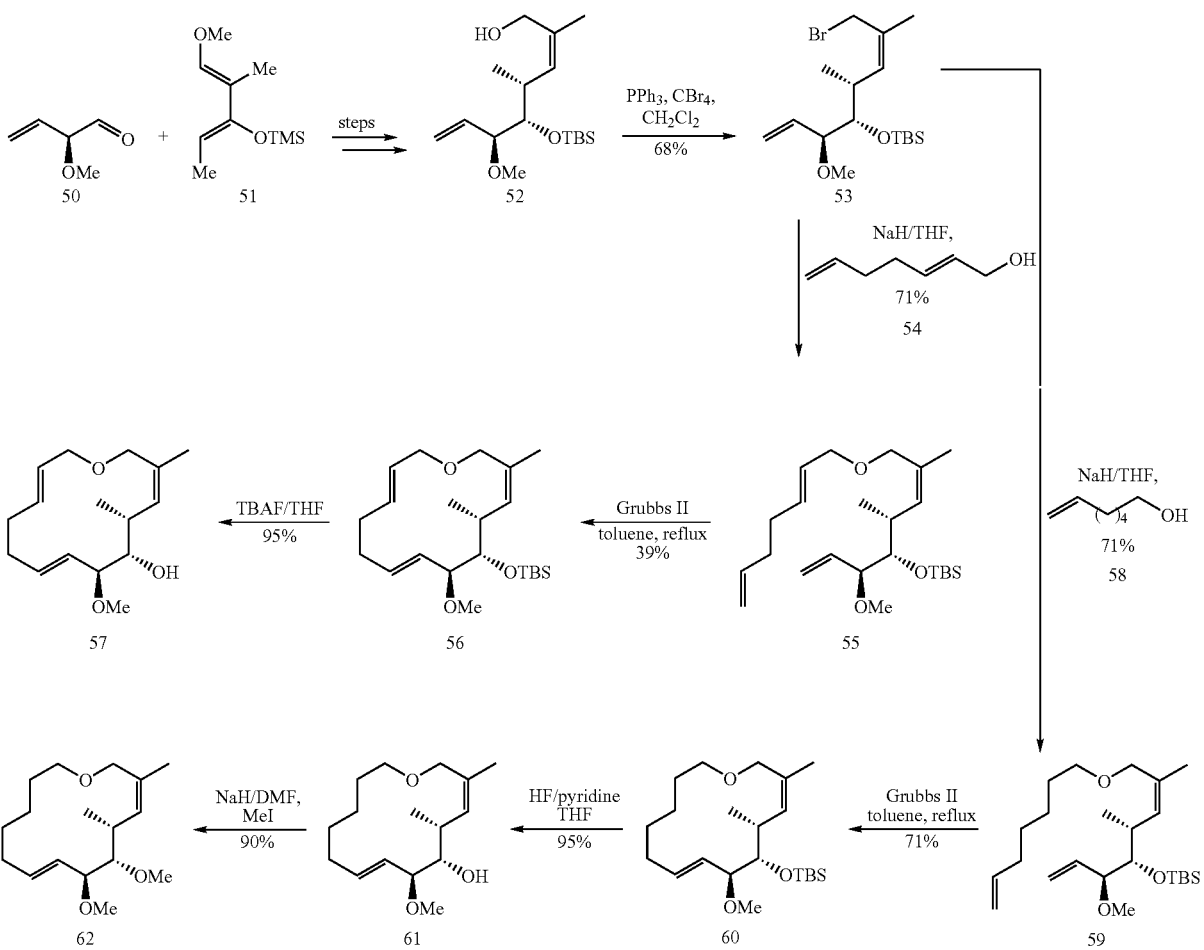

EXPERIMENTAL

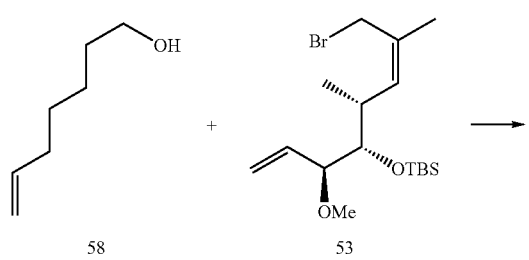

To a suspension of sodium hydride (39 mg, 60% dispersion in mineral oil) in 2 mL THF was added a solution of 6-heptenol (56 mg, 0.494 mmol) in 2 mL THF under argon while cooling at 0° C. and the resulting reaction mixture was stirred for 10 min. Then warmed to rt and stirred for another 10 min. The reaction mixture was then cooled to 0° C. and a solution of allylic bromide 53 (93 mg, 0.247 mmol) in 1.5 mL THF was added. The resulting solution was warmed to rt slowly overnight (12 hr). Saturated $NH_4Cl$ was added, diluted with water, extracted with ethyl acetate three times, and the organic layers were combined, dried with $MgSO_4$ and concentrated to yield crude product, which was purified by flash column chromatography using ethyl acetate in hexanes (2.5% ethyl acetate in hexanes to 5% ethyl acetate in hexanes) to provide the allylated product 59 in 71% yield. $^1$H-NMR (500

MHz, CDCl$_3$) δ 5.77 (m, 1H), 5.66 (m, 1H), 5.34 (d, J=9.73 Hz, 1H), 5.24 (m, 2H), 4.93 (m, 2H), 3.92 (d, J=11.50 Hz, 1H), 3.83 (d, J=10.50 Hz, 1H), 3.40-3.24 (m, 4H), 3.17 (s, 3H), 2.59 (m, 1H), 2.01 (m, 2H), 1.69 (s, 3H), 1.54 (m, 2H), 1.35 (m, 4H), 0.90-0.84 (m, 12H), 0.03 (s, 3H), 0.0 (s, 3H); $^{13}$C-NMR (125 MHz, CDCl$_3$) δ 139.2, 135.6, 134.2, 130.9, 118.7, 114.5, 86.5, 78.8, 70.0, 69.5, 55.4, 34.2, 33.9, 29.8, 29.0, 26.4, 26.0, 21.7, 18.8, 14.3, −3.43, −4.53; MS (ESI) 433.2 [M+Na$^+$].

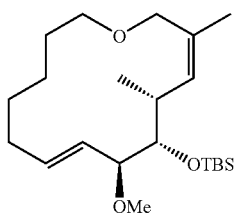

60

To a solution of RCM precursor (100 mg, 0.244 mmol) 59 in 1000 mL refluxing toluene was added Grubbs second generation catalyst (41 mg, 0.048 mmol) and the resulting solution was continued to reflux for 15 minutes. Then the reaction mixture was cooled to 0° C. and filtered through a plug of silica, and the silica was washed with 10% ethyl acetate in hexanes. The combined solution was evaporated to dryness to afford the crude product, which was purified by flash column chromatography using 2% ethyl acetate hexanes to obtain the 66 mg of cyclic ether (71% yield). $^1$H-NMR (500 MHz, CDCl$_3$) δ 5.55 (m, H), 5.49 (d, J=10.0 Hz, 1H), 5.21 (dd, J=15.4 Hz, J=8.51 Hz, 1H), 3.83 (d, J=9.77 Hz, 1H), 3.63 (d, J=9.77 Hz, 1H), 3.52-3.43 (m, 2H), 3.40 (d, J=8.82 Hz, 1H), 3.33 (apt-t, J=8.51 Hz, 1H), 3.17 (s, 3H), 2.88 (m, 1H), 2.22-2.06 (m, 2H), 1.71 (m, 4H), 1.50-1.29 (m, 5H), 0.93-0.78 (m, 12H), 0.032 (s, 3H), 0.00 (s, 3H); $^{13}$C-NMR (125 MHz, CDCl$_3$) δ 135.5, 134.2, 129.8, 118.4, 85.6, 78.7, 69.9, 69.2, 56.2, 34.0, 30.4, 27.0, 26.4, 23.4, 23.3, 18.8, 13.0, −3.5, −4.7; MS (ESI) 405.3 [M+Na$^+$].

61

To a solution of TBS cyclic (66 mg, 0.172 mmol) ether 60 in 2 mL THF was added 0.5 mL HF/pyridine and the resulting reaction mixture was stirred at rt for 10 hr. Then the reaction solution was cooled to 0° C. and 2.5 mL of TMSOMe was added and stirred at rt for 30 min. The reaction mixture was evaporated to dryness and purified by flash column chromatography using 10% ethyl acetate in hexanes to provide 45 mg of ether 61 in 97% yield. $^1$H-NMR (500 MHz, CDCl$_3$) δ 5.65-5.56 (m, 2H), 5.19 (dd, J=15.92 Hz, J=7.52 Hz, 1H), 3.73 (br-s, 2H), 3.56-3.36 (m, 4H), 2.90 (s, 3H), 2.90 (m, 1H), 2.26-2.17 (m, 1H), 2.12-2.01 (m, 1H), 1.73 (br-s, 3H), 1.63 (m, 1H), 1.55-1.30 (m, 5H), 0.91 (d, J=7.08 Hz, 3H); $^{13}$C-NMR (125 MHz, CDCl$_3$) δ 136.2, 134.2, 130.5, 129.2, 84.6, 69.2, 56.5, 32.2, 30.7, 27.1, 26.9, 23.3, 26.2, 12.9; MS (ESI) 291.2 [M+Na$^+$].

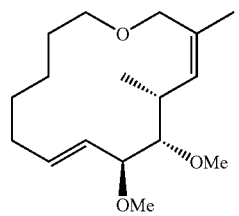

62

To a solution of 61 (5 mg, 0.0186 mmol) in 0.4 mL DMF was added NaH (60% dispersion in mineral oil, 2.2 mg) at 0° C. under argon. Ice bath was removed and the reaction mixture was warmed to rt and stirred for 40 min. Then the solution was cooled to 0° C. and MeI (4.6 μL) was added and the resulting solution was warmed to rt over 1 hr. Then the reaction mixture was quenched 3M NH$_4$OH, diluted with ethyl acetate, washed with water, brine, dried with MgSO$_4$ and concentrated to yield crude product, which was purified by flash column chromatography using 10% ethyl acetate in hexanes to obtained 4.6 mg of corresponding product 62. $^1$H-NMR (500 MHz, CDCl$_3$) δ 5.58 (m, 1H), 5.48 (d, J=10.1 Hz, 1H), 5.24 (dd, J=15.48 Hz, J=7.96 Hz), 3.78 (d, J=9.73 Hz, 1H), 3.71 (d, J=9.73 Hz, 1H), 3.60-3.40 (m, 6H), 3.27 (s, 3H), 2.97 (dd, J=8.85 Hz, J=1.33 Hz), 2.89 (m, 1H), 2.23-2.04 (m, 2H), 1.74 (s, 3H), 1.64 (m, 1H), 1.50-1.29 (m, 5H), 0.87 (d, J=6.63 Hz, 3H); $^{13}$C-NMR (125 MHz, CDCl$_3$) δ 134.8, 134.6, 130.4, 129.9, 87.7, 86.0, 70.0, 69.5, 62.3, 56.8, 33.7, 30.6, 27.3, 27.2, 23.5, 13.6; MS (ESI) 305.3 [M+Na$^+$].

To a 0° C. solution of dienol (379 mg, 3.38 mmol, 3 equiv.) in THF (1.5 mL) was added NaH (65% wt. in mineral oil, 270 mg, 6.76 mmol, 6 equiv.). After 30 minutes at 0° C., mixture was allowed to warm to room temperature for 10 minutes, then cooled back to 0° C. Bromide 53 was then added via cannula (404 mg, 1.13 mmol, 1.0 equiv., solution in 1 mL THF), with 1.5 mL additional THF rinse. The mixture was quenched with saturated aqueous ammonium chloride (5 mL), extracted with 3×10 mL ether, the combined organics were dried over MgSO$_4$, concentrated in vacuo and the residue was purified by silica gel flash chromatography in (2.5% ethyl acetate in hexanes to 5% ethyl acetate in hexanes) to afford 330 mg of product 55 (71% yield). $^1$H-NMR (500 MHz, CDCl$_3$) δ 5.81 (m, 1H), 5.71-5.55 (m, 3H), 5.38 (d, J=9.39 Hz), 5.03 (d, J=17.01 Hz, 1H), 4.97 (d, J=11.44 Hz, 1H), 3.97 (d, J=11.40 Hz, 1H), 3.84 (m, 2H), 3.44 (dd, J=2.83 Hz, J=7.12 Hz, 1H), 3.36 (apparent t, J=16 Hz, 1H) 3.20 (s, 3H), 2.61 (m, 1H), 2.15 (m, 4H), 1.73 (s, 3H), 0.904 (s, 9H), 0.054 (s, 3H), 0.022 (s, 3H); $^{13}$C-NMR (125 MHz, CDCl$_3$) δ 138.37, 135.51, 134.39, 133.76, 130.8, 127.17, 118.80, 114.98, 86.45, 78.79, 70.51, 68.61, 56.34, 34.18, 33.45, 31.88, 26.38, 21.74, 18.77, 14.35, −3.57, −4.57; MS (ESI) 431.3 [M+Na$^+$].

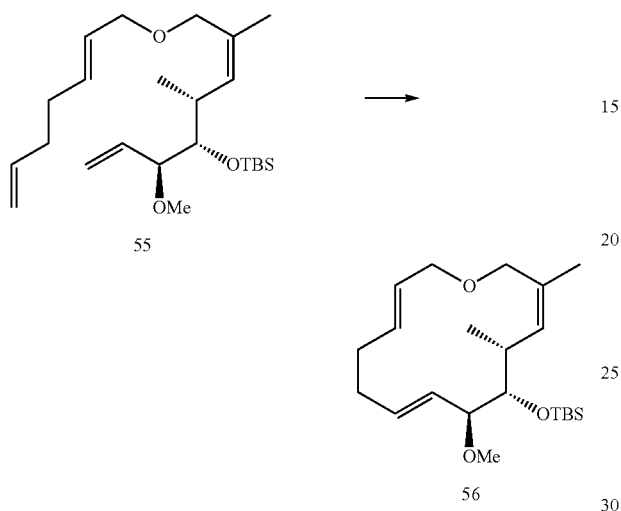

To a solution of RCM precursor 55 (213 mg, 0.521 mmol) in 0.666 mL toluene (7.4 mM), preheated to reflux, was added Grubbs' second-generation catalyst (88 mg, 0.104 mmol, 0.2 equiv.). After 30 min, mixture was cooled, toluene was removed in vacuo, and residue was immediately loaded onto a silica gel column and purified by flash chromatography (2% ethyl acetate in hexanes to 5% ethyl acetate in hexanes) to afford 77 mg of product 56 (39% yield). $^1$H-NMR (500 MHz, CDCl$_3$) δ 5.61-5.51 (m, 2H), 5.45-5.40 (m, 2H), 5.19 (dd, J=7.25 Hz, J=15.63), 4.97 (d, J=11.44 Hz, 1H), 3.97 (d, J=10.26 Hz, 1H), 3.90 (dd, J=5.88, J=13.59 1H), 3.82 (dd, J=6.22 Hz, J=13.48 Hz, 1H), 3.31 (apparent q, J=9 Hz, 2H) 3.19 (s, 3H), 2.71 (m, 1H), 2.37-2.31 (m, 2H), 2.22-2.15 (m, 2H), 1.75 (s, 3H), 0.89 (m, 12H), 0.033 (s, 3H), −0.011 (s, 3H); $^{13}$C-NMR (125 MHz, CDCl$_3$) δ 136.34, 134.45, 133.73, 130.33, 130.211, 127.87, 85.43, 79.64, 69.24, 66.05, 56.37, 33.88, 32.02, 30.69, 26.42, 22.34, 18.88, 13.00, −3.60, −4.77; MS (ESI) 403.3 [M+Na$^+$].

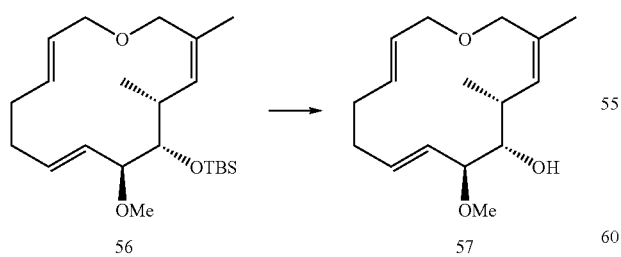

To a 0° C. solution of TBS macroether 56 (77 mg, 0.202 mmol) in 1 mL THF was added 2.0 mL (2.0 mmol) 1.0M TBAF/THF solution. Mixture was then allowed to warm to room temperature. After 24 hours, mixture was diluted with water (5 mL), extracted with 3×10 mL ether, organics were combined and dried over MgSO$_4$, then concentrated in vacuo. Residue was purified by flash chromatography on silica gel (10% ethyl acetate in hexanes) to give 51 mg of product 57 (95% yield). $^1$H-NMR (400 MHz, CDCl$_3$) δ 5.64-5.86 (m, 1H), 5.55-5.50 (m, 2H), 5.45-5.36 (m, 1H), 5.16 (dd, J=8.39 Hz, J=15.74), 3.96 (m, 1H), 3.92 (m, 1H), 3.78 (dd, J=6.68 Hz, J=13.46 Hz, 1H), 3.38 (apparent t, J=9 Hz, 2H) 3.28 (s, 3H), 2.75 (s, 1H), 2.67 (m, 1H), 2.40-2.32 (m, 2H), 2.25-2.19 (m, 2H), 1.77 (s, 3H), 0.92 (d, J=6.79 3H); $^{13}$C-NMR (125 MHz, CDCl$_3$) δ136.06, 135.09, 134.27, 131.12, 129.37, 127.89, 84.38, 77.79, 69.35, 65.96, 56.53, 32.09, 32.01, 30.77, 22.35, 12.80; MS (ESI) 289.2 [M+Na$^+$].

We claim:

1. An isolated compound having the structure:

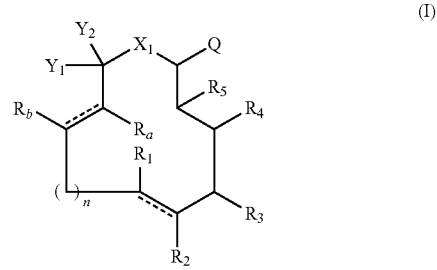

(I)

or pharmaceutically acceptable salt, amide, or ester thereof;

wherein n is an integer from 1 to 4;

$R_1$ and $R_2$ are each independently hydrogen, an aliphatic moiety, or an aromatic moiety;

$R_3$ is hydrogen, halogen, aliphatic, heteroaliphatic, alicyclic, heterocyclic, aryl or heteroaryl moiety, or —WR$^{3A}$; wherein W is independently —O—, —S—, —NR$^{3B}$— or —C(=O)—, wherein R$^{3A}$ is hydrogen, an aliphatic, heteroaliphatic, alicyclic, heterocyclic, aryl or heteroaryl moiety; —C(=O)R$^{3C}$, —Si(R$^{3C}$)$_3$, —C(=S) R$^{3C}$, —C(=NR$^{3C}$)R$^{3C}$, —SO$_2$R$^{3C}$, or —ZR$^{3C}$, wherein Z is —O—, —S—, —NR$^{3D}$, wherein each occurrence of R$^{3B}$, R$^{3C}$ and R$^{3D}$ is independently hydrogen, or an aliphatic, heteroaliphatic, alicyclic, heterocyclic, aryl or heteroaryl moiety;

$R_4$ is halogen, —OR$^{4A}$, —OC(=O)R$^{4A}$ or —NR$^{4A}$R$^{4B}$; wherein R$^{4A}$ and R$^{4B}$ are independently hydrogen, an aliphatic, heteroaliphatic, alicyclic, heteroalicyclic, aromatic or heteroaromatic moiety; a nitrogen protecting group or an oxygen protecting group; or R$^{4A}$ and R$^{4B}$, taken together with the nitrogen atom to which they are attached, form a heterocyclic or heteroaryl moiety; or $R_4$, taken together with the carbon atom to which it is attached forms a moiety having the structure:

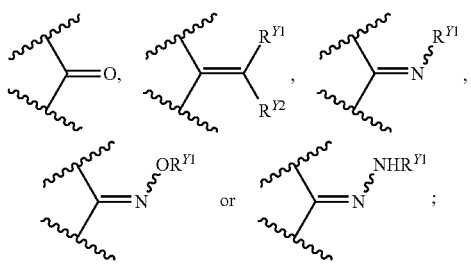

$R_5$ is hydrogen, an aliphatic, heteroaliphatic, alicyclic, heteroalicyclic, aromatic or heteroaromatic moiety;

$R_a$ is independently hydrogen, —CN, —S(O)$_{1-2}$R$^{a1}$, —NO$_2$, —COR$^{a1}$, —CO$_2$R$^{a1}$, —NR$^{a1}$C(=O)R$^{a2}$, NR$^{a1}$C(=O)OR$^{a2}$, —CONR$^{a1}$R$^{a2}$, or an aliphatic moiety, wherein each occurrence of R$^{a1}$ and R$^{a2}$ is independently hydrogen, or an aliphatic, heteroaliphatic, alicyclic, heteroalicyclic, aromatic or heteroaromatic moiety;

$R_b$ is independently hydrogen, an aliphatic moiety, or an aromatic moiety;

$X_1$ is O, or S;

Q is hydrogen, halogen, —CN, $C_{1-6}$ aliphatic optionally substituted with halogen, $C_{1-6}$ heteroaliphatic, or —WR$^{Q1}$; wherein W is independently —O—, —S— or —NR$^{Q3}$—, wherein each occurrence of R$^{Q1}$ and R$^{Q3}$ is independently hydrogen or $C_{1-6}$ alkyl;

$Y_1$ and $Y_2$ are independently hydrogen, an aliphatic, heteroaliphatic, alicyclic, heteroalicyclic, aromatic or heteroaromatic moiety; or —WR$^{Y1}$, wherein W is independently —O—, —S— or —NR$^{Y2}$—, and each occurrence of R$^{Y1}$ and R$^{Y2}$ is independently hydrogen, or an aliphatic, heteroaliphatic, alicyclic, heteroalicyclic, aromatic or heteroaromatic moiety; or $Y_1$ and $Y_2$ together with the carbon atom to which they are attached form a moiety having the structure:

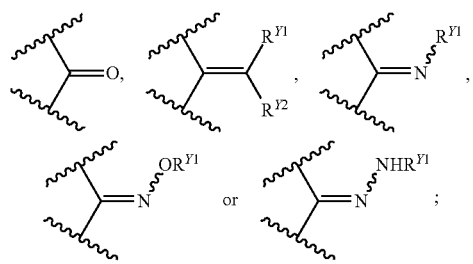

2. The compound of claim 1, wherein:

$R_1$ and $R_2$ are each independently hydrogen or substituted or unsubstituted lower alkyl;

$R_3$ is hydrogen, halogen, alkyl, heteroalkyl, cycloalkyl, heterocycloalkyl, aryl or heteroaryl moiety, or —WR$^{3A}$; wherein W is independently —O—, —S—, —NR$^{3B}$— or —C(=O)—, wherein R$^{3A}$ is hydrogen, an alkyl, heteroalkyl, cycloalkyl, heterocycloalkyl, aryl or heteroaryl moiety; —C(=O)R$^{3C}$, —Si(R$^{3C}$)$_3$, —C(=S)R$^{3C}$, —C(=NR$^{3C}$)R$^{3C}$, —SO$_2$R$^{3C}$, or —ZR$^{3C}$, wherein Z is —O—, —S—, —NR$^{3D}$, wherein each occurrence of R$^{3B}$, R$^{3C}$ and R$^{3D}$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heteroalicyclic, aryl or heteroaryl moiety;

$R_4$ is halogen, —OR$^{4A}$, —OC(=O)R$^{4A}$ or —NR$^{4A}$R$^{4B}$; wherein R$^{4A}$ and R$^{4B}$ are independently hydrogen, or substituted or unsubstituted lower alkyl; a nitrogen protecting group or an oxygen protecting group; or R$^{4A}$ and R$^{4B}$B, taken together with the nitrogen atom to which they are attached, form a heterocyclic or heteroaryl moiety; or $R_4$, taken together with the carbon atom to which it is attached forms a moiety having the structure:

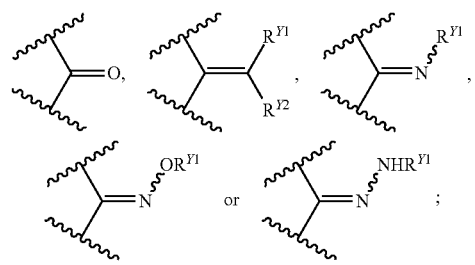

$R_5$ is hydrogen or substituted or unsubstituted lower alkyl;

$R_a$ is independently a hydrogen or an alkyl moiety;

$R_b$ is independently hydrogen, alkyl, an aryl moiety or a heteroaryl moiety;

$X_1$ is O, or S;

$Y_1$ and $Y_2$ are independently hydrogen, an alkyl, heteroalkyl, cycloalkyl, heterocycloalkyl, aryl or heteroaryl moiety; or —WR$^{Y1}$, wherein W is independently —O—, —S— or —NR$^{Y2}$—, and each occurrence of R$^{Y1}$ and R$^{Y2}$ is independently hydrogen, or an alkyl, heteroalkyl, cycloalkyl, heterocycloalkyl, aryl or heteroaryl moiety; or $Y_1$ and $Y_2$ together with the carbon atom to which they are attached form a moiety having the structure:

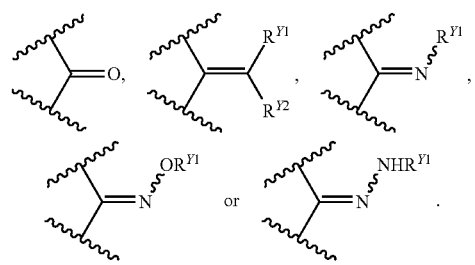

3. The compound of claim 2, wherein the compound has one of the following structures:

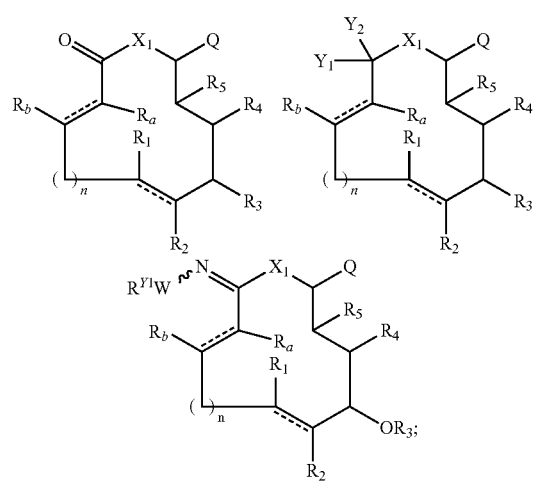

wherein W is O or NH; and R$^{Y1}$ is independently an aryl or heteroaryl moiety.

4. The compound of claim 3, wherein Q is hydrogen.

5. The compound of claim 2, wherein $R_a$ and $R_b$ are each hydrogen, Q is hydrogen and the compound has the following structure:

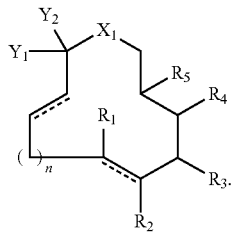

6. The compound of claim 2, wherein $Y_1$, $Y_2$, $R_a$ and $R_b$ are each hydrogen, Q is hydrogen, and the compound has the following structure:

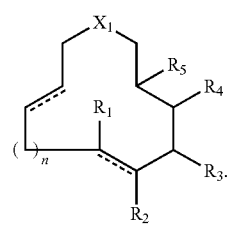

7. The compound of claim 2, having the following structure:

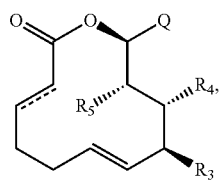

wherein $R^{3A}$ is hydrogen, lower alkyl or lower acyl.

8. The compound of claim 2, having the following structure:

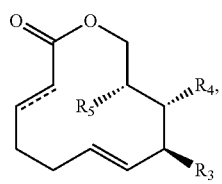

9. The compound of claim 2, having the structure:

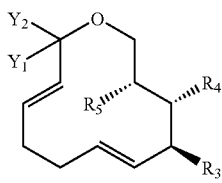

wherein $Y_1$ and $Y_2$ are independently hydrogen or alkyl.

10. The compound of claim 2, having the structure:

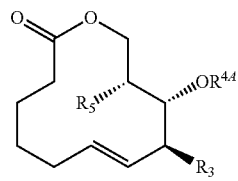

wherein $R^{4A}$ is hydrogen or lower alkyl.

11. The compound of claim 1, wherein $R_1$ and $R_2$ are each hydrogen.

12. The compound of claim 1, wherein $R_5$ is methyl.

13. The compound of claim 1, wherein $R_3$ is lower alkoxy.

14. The compound of claim 13, wherein $R_3$ is methoxy.

15. The compound of claim 1, wherein $R_4$ is OH, OAc, $NH_2$ or halogen, or $R_4$ taken together with the carbon atom to which it is attached forms a moiety having the structure:

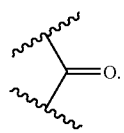

16. The compound of claim 1, wherein the stereocenter

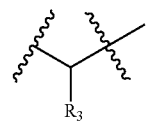

has the following stereochemistry

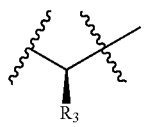

17. The compound of any one of claim 1, wherein the stereocenter

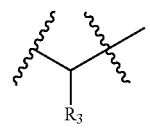

has the following stereochemistry

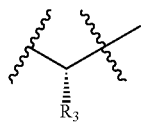

18. The compound of claim 1 having the structure:

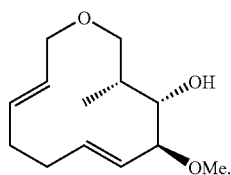

19. The compound of claim 1 having the structure:

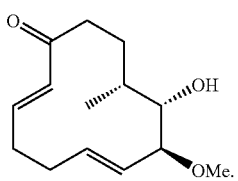

20. A pharmaceutical composition comprising:
a pharmaceutically acceptable carrier, adjuvant or vehicle; and
a compound of claim 1.

21. The pharmaceutical composition of claim 20 wherein the compound is present in an amount effective to inhibit the metastasis of tumor cells.

22. The pharmaceutical composition of claim 20 wherein the compound is present in an amount effective to inhibit angiogenesis.

23. The composition of claim 20, further comprising a cytotoxic agent.

24. The composition of claim 23, wherein the cytotoxic agent is an anticancer agent.

25. The composition of claim 24, wherein the anticancer agent is 12,13-desoxyepothilone B, (E)-9,10-dehydro-12,13-desoxyEpoB, 26-CF3-(E)-9,10-dehydro-12,13-desoxyEpoB, taxol, radicicol or TMC-95A/B.

26. The composition of claim 20, further comprising a palliative agent.

27. A method for treating or lessening the severity of metastasis of tumor cells in a subject comprising:
administering to a subject in need thereof a therapeutically effective amount of a compound according to claim 1 or a composition according to claim 20;
wherein the compound of claim 1 or composition of claim 20 inhibits metastasis of ovarian or colon tumor cells; and
wherein said method optionally further comprises a cytotoxic agent.

28. The method of claim 27, wherein the cancer is a solid tumor.

29. The method of claim 27, wherein the cytotoxic agent is an anticancer agent.

30. The method of claim 29, wherein the anticancer agent is 12,13-desoxyepothilone B, (E)-9,10-dehydro-12,13-desoxyEpoB, 26-CF3-(E)-9,10-dehydro-12,13-desoxyEpoB, taxol, radicicol or TMC-95A/B.

31. The method of claim 27, further comprising administering a palliative agent.

32. A method for treating or lessening the severity of cancer in a subject comprising administering to a subject in need thereof a therapeutically effective amount of a compound according to claim 1 or a composition according to claim 20 wherein the cancer is ovarian or colon.

33. The method of claim 32, wherein the dosage is between about 0.1 mg/kg to about 50 mg/kg of body weight.

34. The method of claim 32, wherein the dosage is between about 0.1 mg/kg to about 40 mg/kg of body weight.

35. The method of claim 32, wherein the dosage is between about 0.1 mg/kg to about 30 mg/kg of body weight.

36. The method of claim 32, wherein the dosage is between about 0.1 mg/kg to about 20 mg/kg of body weight.

37. The method of claim 32, wherein the dosage is between about 1 mg/kg to about 50 mg/kg of body weight.

38. The method of claim 32, wherein the dosage is between about 1 mg/kg to about 40 mg/kg of body weight.

39. The method of claim 32, wherein the dosage is between about 1 mg/kg to about 30 mg/kg of body weight.

40. The method of claim 32, wherein the dosage is between about 1 mg/kg to about 20 mg/kg of body weight.

41. The method of claim 32, wherein the dosage is between about 5 mg/kg to about 50 mg/kg of body weight.

42. The method of claim 32, wherein the dosage is between about 5 mg/kg to about 40 mg/kg of body weight.

43. The method of claim 32, wherein the dosage is between about 5 mg/kg to about 30 mg/kg of body weight.

44. The method of claim 32, wherein the dosage is between about 5 mg/kg to about 25 mg/kg of body weight.

45. The method of claim 32, wherein the dosage is between about 10 mg/kg to about 50 mg/kg of body weight.

46. The method of claim 32, wherein the dosage is between about 10 mg/kg to about 40 mg/kg of body weight.

47. The method of claim 32, wherein the dosage is between about 10 mg/kg to about 30 mg/kg of body weight.

48. The method of claim 32, wherein the dosage is between about 10 mg/kg to about 20 mg/kg of body weight.

49. The method of claim 32, wherein the dosage is 10 mg/kg or greater of body weight.

50. The method of claim 32, wherein the cancer is ovarian cancer.

51. The method of claim 50, wherein the compound is present in an amount effective to inhibit metastasis of ovarian tumor cells.

52. The method of claim 32, further comprising a cytotoxic agent.

53. The method of claim 52, wherein the cytotoxic agent is an anticancer agent.

54. The method of claim 32, further comprising a palliative agent.

55. The method of claim 32, wherein the composition is administered at a dosage between about 10 mg/kg to about 20 mg/kg of body weight.

56. The method of claim 51, further comprising administering a cytotoxic agent.

57. The method of claim 56, wherein the cytotoxic agent is an anticancer agent.

58. The method of claim 51, further comprising administering a palliative agent.

59. A compound having the structure:

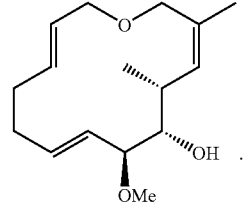

* * * * *